(12) United States Patent
Ortyn et al.

(10) Patent No.: US 6,778,263 B2
(45) Date of Patent: Aug. 17, 2004

(54) METHODS OF CALIBRATING AN IMAGING SYSTEM USING CALIBRATION BEADS

(75) Inventors: William E. Ortyn, Bainbridge Island, WA (US); David A. Basiji, Seattle, WA (US); Keith L. Frost, Seattle, WA (US); Brian E. Hall, Seattle, WA (US); Michael J. Seo, Mercer Island, WA (US)

(73) Assignee: Amnis Corporation, Seattle, MA (US)

( * ) Notice: Subject to any disclaimer, the term of this patent is extended or adjusted under 35 U.S.C. 154(b) by 0 days.

(21) Appl. No.: 10/348,193

(22) Filed: Jan. 16, 2003

(65) Prior Publication Data

US 2003/0142289 A1 Jul. 31, 2003

Related U.S. Application Data

(63) Continuation-in-part of application No. 09/939,292, filed on Aug. 24, 2001, now Pat. No. 6,532,061.
(60) Provisional application No. 60/228,076, filed on Aug. 25, 2000, now abandoned.

(51) Int. Cl.[7] ................................................ G01P 3/36
(52) U.S. Cl. ........................................ 356/28; 356/28.5
(58) Field of Search .................................. 356/28, 28.5

(56) References Cited

U.S. PATENT DOCUMENTS

| | | | |
|---|---|---|---|
| 3,922,069 A | 11/1975 | Kishikawa et al. ......... 359/633 |
| 4,770,992 A | 9/1988 | Van den Engh et al. ........ 435/6 |
| 5,096,807 A | 3/1992 | Leaback ....................... 435/6 |
| 5,141,609 A | 8/1992 | Sweedler et al. .......... 356/344 |
| 5,491,642 A | * 2/1996 | Wormell et al. |
| 5,695,934 A | 12/1997 | Brenner ......................... 435/6 |
| 5,848,123 A | 12/1998 | Strommer .................. 378/98.8 |
| 5,855,753 A | 1/1999 | Trau et al. ................... 204/484 |
| 5,929,986 A | 7/1999 | Slater et al. ................ 356/326 |
| 5,959,953 A | 9/1999 | Alon ....................... 369/44.41 |
| 5,982,478 A | * 11/1999 | Ainsworth et al. |
| 6,007,994 A | 12/1999 | Ward et al. ..................... 435/6 |
| 6,014,468 A | 1/2000 | McCarthy et al. .......... 382/254 |
| 6,066,459 A | 5/2000 | Garini et al. ................... 435/6 |
| 6,116,739 A | 9/2000 | Ishihara et al. .............. 353/31 |
| 6,156,465 A | 12/2000 | Cao et al. ...................... 430/30 |
| 6,210,973 B1 | 4/2001 | Pettit ......................... 436/172 |
| 6,211,955 B1 | 4/2001 | Basiji et al. ................ 356/326 |
| 6,249,341 B1 | 6/2001 | Basiji et al. .................. 356/73 |
| 6,330,081 B1 | 12/2001 | Scholten ..................... 358/463 |
| 6,381,363 B1 | 4/2002 | Murching et al. .......... 382/164 |
| 6,522,781 B1 | 2/2003 | Norikane et al. ........... 382/203 |
| 2001/0006416 A1 | 7/2001 | Johnson ....................... 356/73 |
| 2002/0126275 A1 | 9/2002 | Johnson ...................... 356/317 |

* cited by examiner

*Primary Examiner*—Stephen C. Buczinski
(74) *Attorney, Agent, or Firm*—Ronald M. Anderson

(57) ABSTRACT

When utilized in a flow imaging instrument, calibration beads provide a known data source that can be employed in various self-diagnostic, calibration and quality metric applications for the both the optical system of the flow imaging instrument, as well as the flow cell of the flow imaging instrument. Such data can be used to determine point spread functions associated with an imaging system, to determine a sensitivity of an imaging system, and to determine a focal point of the imaging system. Imagery collected from calibration beads can be used to determine core size and stability and TDI/flow speed synchronization. Calibration beads can be beneficially employed to enable stable system operation, even when very low sample concentration, or very small sample sizes are to be analyzed.

59 Claims, 51 Drawing Sheets

FLOW CYTOMETER WITH CELL SORTING

PROCESSING A SIGNAL SEGMENT

FIG. 48 PROCESSING A SIGNAL SEGMENT

METHODS OF CALIBRATING AN IMAGING SYSTEM USING CALIBRATION BEADS

RELATED APPLICATIONS

This application is a continuation in part of a prior application Ser. No. 09/939,292, filed on Aug. 24, 2001, now U.S. Pat. No. 6,532,061 which itself is based on a prior provisional application Serial No. 60/228,076, filed on Aug. 25, 2000 now abandoned, the benefits of the filing dates of which are hereby claimed under 35 U.S.C. § 119(e) and 35 U.S.C. § 120.

FIELD OF THE INVENTION

The present invention generally relates to a method for using calibration beads to enhance the performance of a flow imaging system, and more specifically, to using calibration beads to facilitate the reliable collection of velocity data used by the flow imaging system.

BACKGROUND OF THE INVENTION

Cells and cell groupings are three-dimensional objects containing rich spatial information. The distribution of a tremendous variety of bio-molecules can be identified within a cell using an ever-increasing number of probes. In the post-genome era, there is mounting interest in understanding the cell, not only as a static structure, but as a dynamic combination of numerous interacting feedback control systems. This understanding can lead to new drugs, better diagnostics, more effective therapies, and better health care management strategies. However, this understanding will require the ability to extract a far greater amount of information from cells than is currently possible.

The principal technologies for cellular analysis are automated microscopy and flow cytometry. The information generated by these mature technologies, although useful, is often not as detailed as desired. Automated microscopy allows two-dimensional (2D) imaging of from one to three colors of cells on slides. Typical video frame rates limit kinetic studies to time intervals of 30 ms.

Instruments known as flow cytometers currently provide vital information for clinical medicine and biomedical research by performing optical measurements on cells in liquid suspension. Whole blood, fractionated components of blood, suspensions of cells from biopsy specimens and from cell cultures, and suspensions of proteins and nucleic acid chains are some of the candidates suitable for analysis by flow cytometry. In flow cytometers specialized for routine blood sample analysis, cell type classification is performed by measuring the angular distribution of light scattered by the cells and the absorption of light by specially treated and stained cells. The approximate numbers of red blood cells, white blood cells of several types, and platelets are reported as the differential blood count. Some blood-related disorders can be detected as shifts in optical characteristics, as compared to baseline optical characteristics, such shifts being indicative of morphological and histochemical cell abnormalities. Flow cytometers have been adapted for use with fluorescent antibody probes, which attach themselves to specific protein targets, and for use with fluorescent nucleic acid probes, which bind to specific DNA and RNA base sequences by hybridization. Such probes find application in medicine for the detection and categorization of leukemia, for example, in biomedical research, and drug discovery. By employing such prior art techniques, flow cytometry can measure four to ten colors from living cells. However, such prior art flow cytometry offers little spatial resolution, and no ability to study a cell over time. There is clearly a motivation to address the limitations of existing cell analysis technologies with a novel platform for high speed, high sensitivity cell imaging.

A key issue that arises in cell analysis carried out with imaging systems is the measurement of the velocity of a cell or other object through the imaging system. In a conventional time-domain methodology, cell velocity is measured using time-of-flight (TOF). Two detectors are spaced a known distance apart and a clock measures the time it takes a cell to traverse the two detectors. The accuracy of a TOF measurement is enhanced by increasing detector spacing. However, this increases the likelihood that multiple cells will occupy the measurement region, requiring multiple timers to simultaneously track all cells in view. Initially, the region between the detectors is cleared before starting sample flow. As cells enter the measurement region, each entry signal is timed separately. The system is synchronized with the sample by noting the number of entry signals that occur before the first exit signal.

TOF velocity measurement systems are prone to desynchronization when the entry and exit signals are near threshold, noise is present, or expected waveform characteristics change due to the presence of different cell types and orientations. Desynchronization causes errors in velocity measurement that can lead to degraded signals and misdiagnosed cells until the desynchronized condition is detected and corrected. Resynchronization may require that all cells be cleared from the region between the detectors before restarting sample flow, causing the loss of sample.

Significant advancements in the art of flow cytometry are described in commonly assigned U.S. Pat. No. 6,249,341, issued on Jun. 19, 2001, and entitled IMAGING AND ANALYZING PARAMETERS OF SMALL MOVING OBJECTS SUCH AS CELLS, as well as in commonly assigned U.S. Pat. No. 6,211,955, issued on Apr. 3, 2001, also entitled IMAGING AND ANALYZING PARAMETERS OF SMALL MOVING OBJECTS SUCH AS CELLS. The specifications and drawings of each of these patents are hereby specifically incorporated herein by reference.

The inventions disclosed in the above noted patents perform high resolution, high-sensitivity two-dimensional (2D) and three-dimensional (3D) imaging using time-delay-integration (TDI) electronic image acquisition with cells in flow. These instruments are designed to expand the analysis of biological specimens in fluid suspensions beyond the limits of conventional flow cytometers. TDI sensors utilize solid-state photon detectors such as charge-coupled device (CCD) arrays and shift lines of photon-induced charge in synchronization with the flow of the specimen. The method allows a long exposure time to increase a signal-to-noise ratio (SNR) in the image while avoiding blurring. However, precise synchronization of the TDI detector timing with the motion of the moving targets is required. For example, if a target is to traverse 100 lines of a TDI sensor to build an image, and the blurring is expected to be less than a single line width, then the velocity of the target must be known to less than one percent of its actual value. It would thus be desirable to provide method and apparatus capable of producing highly accurate flow velocity for such moving targets.

Several methods for determining velocity for use in such flow imaging instruments are described in commonly assigned, copending application entitled MEASURING THE VELOCITY OF SMALL MOVING OBJECTS SUCH AS CELLS, Ser. No. 09/939,292, filed on Aug. 24, 2001, the specification and drawings of which are hereby specifically incorporated by reference.

Proper functioning of flow imaging systems that require the synchronization of a TDI detector with objects in flow requires consistent and reliable velocity information. This can be particularly difficult to achieve when the fluid flow contains only a small number of particles, when only a small volume of sample fluid is available, when only limited amounts of light from target cells are available, and when a distribution of target cells in a sample is uneven. It would be desirable to provide a method for determining reliable velocity data under such conditions. It would further be desirable to provide methods to facilitate diagnostic and calibration procedures for flow imaging systems.

SUMMARY OF THE INVENTION

The present invention is a method for utilizing calibration beads to enhance the performance of a flow imaging system. Related applications have described preferred flow imaging systems and preferred methods of measuring the velocity of objects in flow passing through such systems. Such imaging systems are beneficially employed to produce images of objects of interest, such as biological cells.

Non sample particles, referred to as calibration beads, can be introduced into a flow of fluid in such a flow imaging system for the purpose of establishing a velocity. Such calibration beads are preferably polymer micro spheres, but it should be understood that substantially any object capable of being suspended in a fluid, and whose dimensions are compatible with the imaging system being employed, can be utilized as a calibration bead. With respect to the dimensions, such calibration beads must be small enough to pass through the flow cell of the imaging system without obstruction, and yet large enough to be readily detectable by the imaging systems optics and sensors. An optimal size calibration bead for a first imaging system may not represent an optimal size for a second imaging system. Examples of particles that can be beneficially employed as calibration beads include cells, cell clusters, labeled and unlabelled micro spheres (polymer, copolymer, tetra polymer and silica beads).

The use of such calibration beads is particularly helpful when the fluid flow contains only a small number of particles, when only a small volume of sample fluid is available, when only limited amounts of light from target cells are available, when a distribution of target cells in a sample is uneven, and to facilitate diagnostic and calibration procedures.

When the fluid flow contains only a small number of particles it is useful to employ a relatively high concentration of calibration beads, to enable the continuous detection of flow speed velocity. The continuous velocity measurement enables continuous TDI detector/flow speed synchronization, enhancing the stability and performance of flow imaging systems. When a sample particle is imaged, the stable TDI detector/flow speed synchronization facilitates the collection of more precise sample data than can be achieved in an imaging system with poor TDI detector/flow speed synchronization. A preferred concentration of calibration beads will be selected based on parameters of the flow imaging system being employed, to ensure that sufficient calibration beads are provided so that the velocity of the fluid in the flow cell is continually monitored.

Another circumstance in which the use of calibration beads can facilitate accurate velocity measurements is when the actual volume of the sample is small. A fluid flow of calibration beads (i.e. no sample) can be employed to initialize a flow imaging system, and to establish a stable hydrodynamically focused fluid flow in the flow cell of such an imaging system. The calibration beads enable the TDI Camera/Velocity synchronization to be established. When the imaging system and fluid flow is stable, the sample containing the objects of imaging interest can be introduced into the flow cell for analysis of the sample objects.

The amount of light from an object corresponds to the precision of the velocity measurement. Lower levels of light provide less precise velocity data. Often objects of interest (i.e.) samples are so small that while they do provide sufficient light to generate an image, the velocity data obtainable is less precise than desired, thereby making accurate TDI synchronization with the fluid flow difficult. As the signal strength of the light from the objects is generally proportional the size of the object, calibration beads that are larger than the anticipated size of the objects of interests can be employed to increase velocity detection resolution.

In a related problem, samples can include several different types of objects of interest, each of which are of different sizes or properties, and each of which provide different levels of light from which images and velocity data can be obtained. Different levels of light correspond to different levels of precision in determining velocity, which in turn means that the TDI synchronization with the fluid flow can undesirably vary. Adding calibration beads to such a sample volume provides a consistent velocity signal, enabling TDI synchronization to be more reliably maintained.

When utilized in a flow imaging instrument, calibration beads can also provides a known data source that can be employed in various self-diagnostic, calibration and quality metric applications for the both the optical system of the flow imaging instrument, as well as the flow cell of the flow imaging instrument. Such data can be used to determine point spread functions associated with an imaging system, to determine a sensitivity of an imaging system, and to determine a focal point of the imaging system. Imagery collected from calibration beads can be used to determine core size and stability and TDI/flow speed synchronization.

Preferred calibration beads are polymeric beads, including but not limited to following types: polystyrene, styrene/divinylbenzene copolymer (S/DVB), polymethylmethacrylate (PMMA), polyvinyltoluene (PVT), styrene/butadiene (S/B), styrene/vinyltoluene (S/VT). Mixtures of different types of calibration beads may be used. Preferable calibration beads will have densities in the range of 0.9–2.3 grams per cubic centimeter, and diameters that range from 20 nanometers to 50 microns. Calibration beads may incorporate surface functional groups enabling the covalent coupling of ligands. Such surface functional groups preferably include: sulfate based groups ($-SO_4$), aldehyde based groups ($-CHO$), aliphatic amine based groups ($-CH_2-NH_2$), amide based groups ($-CONH_2$), aromatic amine based groups ($-NH_2$), carboxylic acid based groups ($-COOH$), chloromethyl based groups ($-CH_2-Cl$), hydrazide based groups ($CONH-NH_2$), hydroxyl based groups ($-OH$), and sulfonate based groups ($-SO_3$). Calibration beads can be beneficially incorporate a coating of protein A or streptavidin. Further, calibration beads can include dyed microspheres of different colors, fluorescent labeled microspheres, magnetic microspheres, and molecularly imprinted micro spheres.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 26:
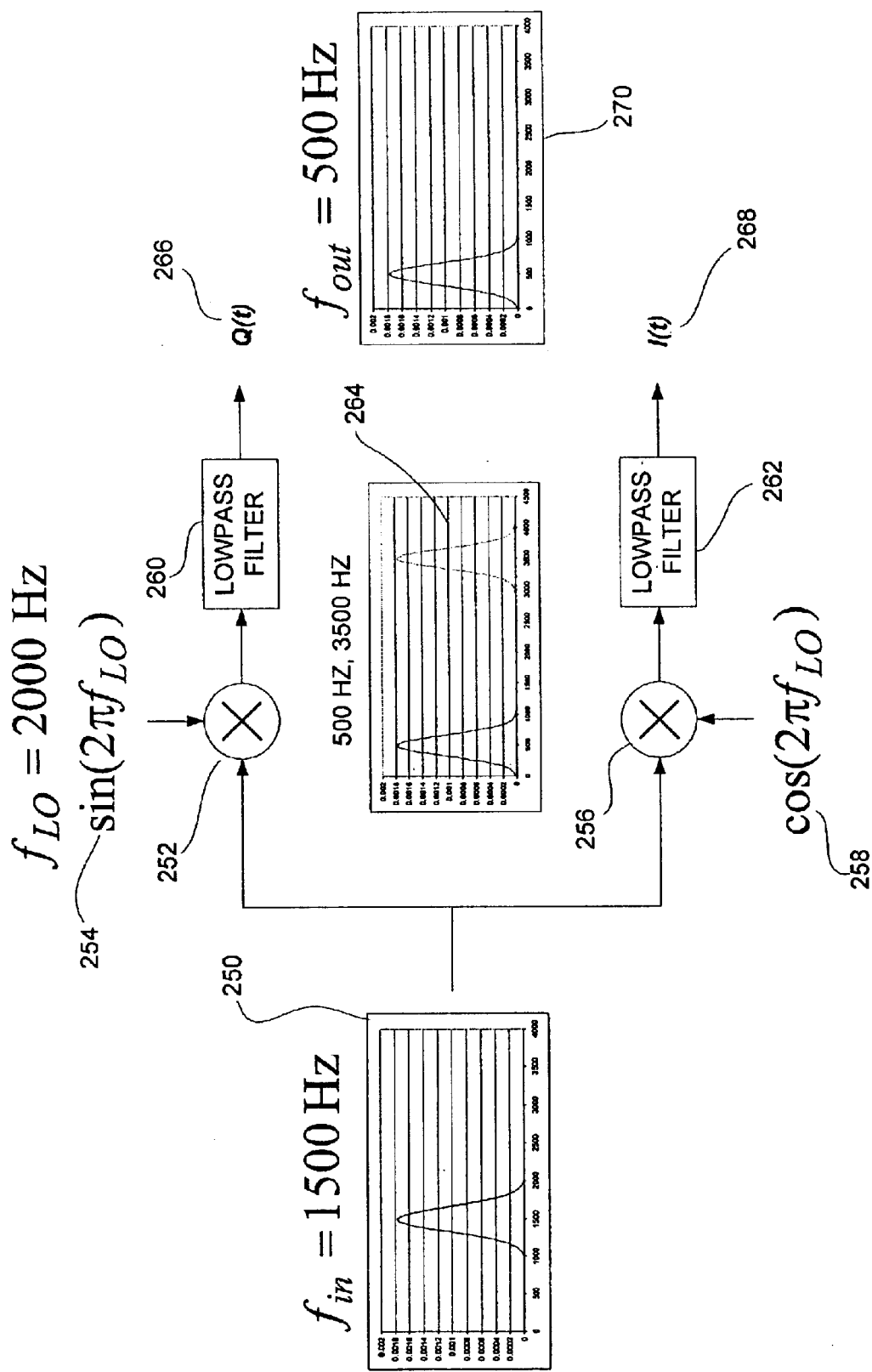
Figure 27:
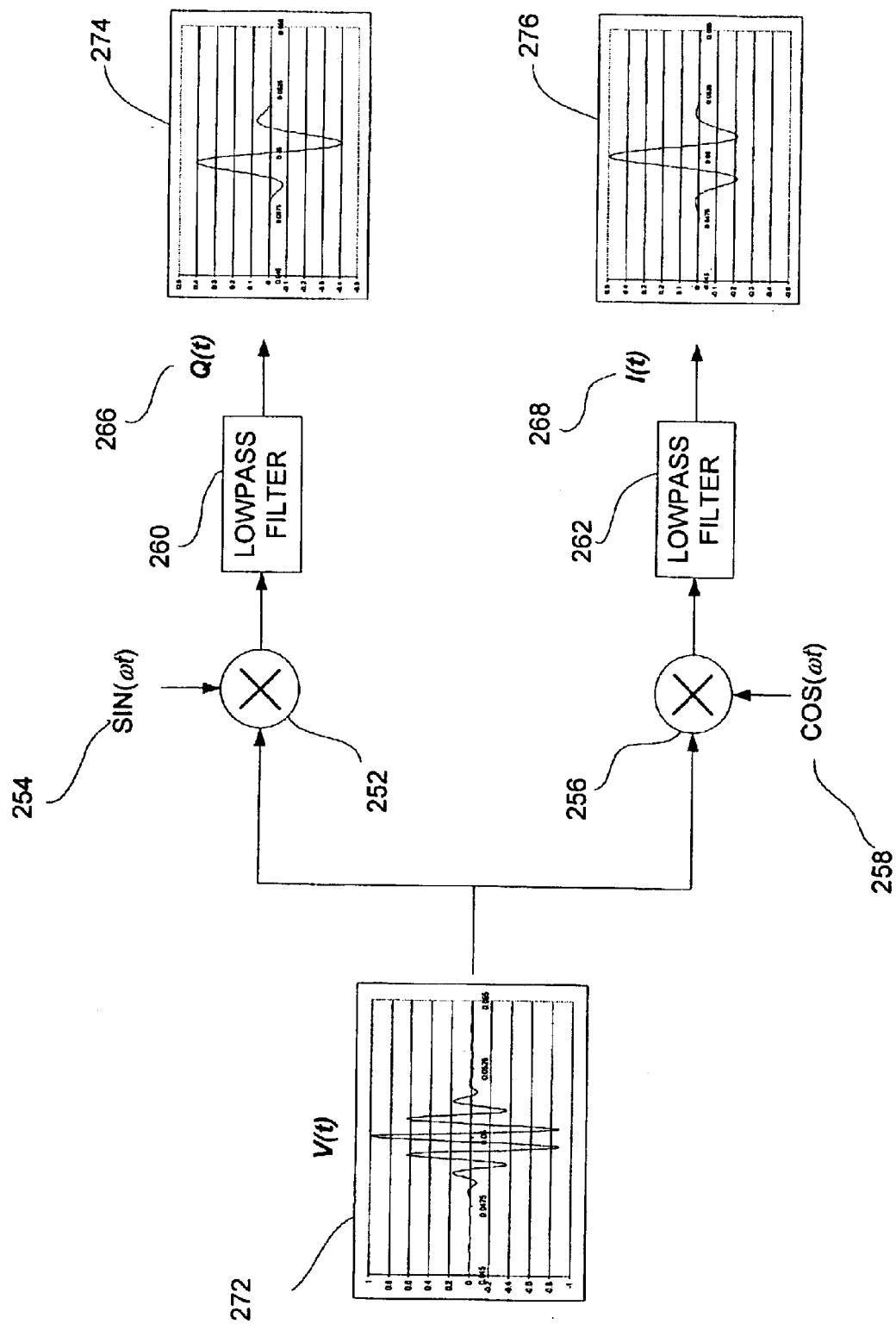
Figure 28:
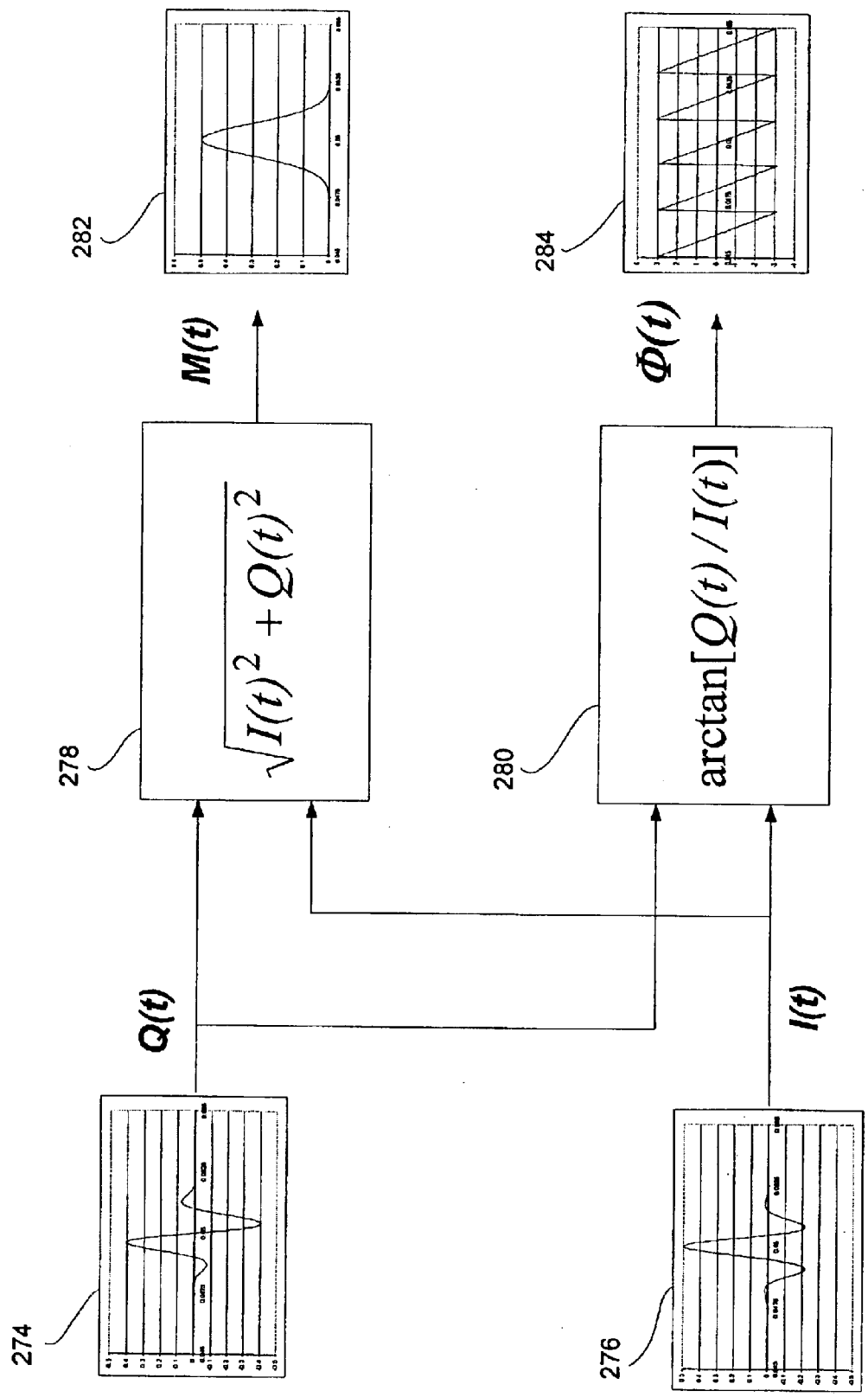
Figure 29:
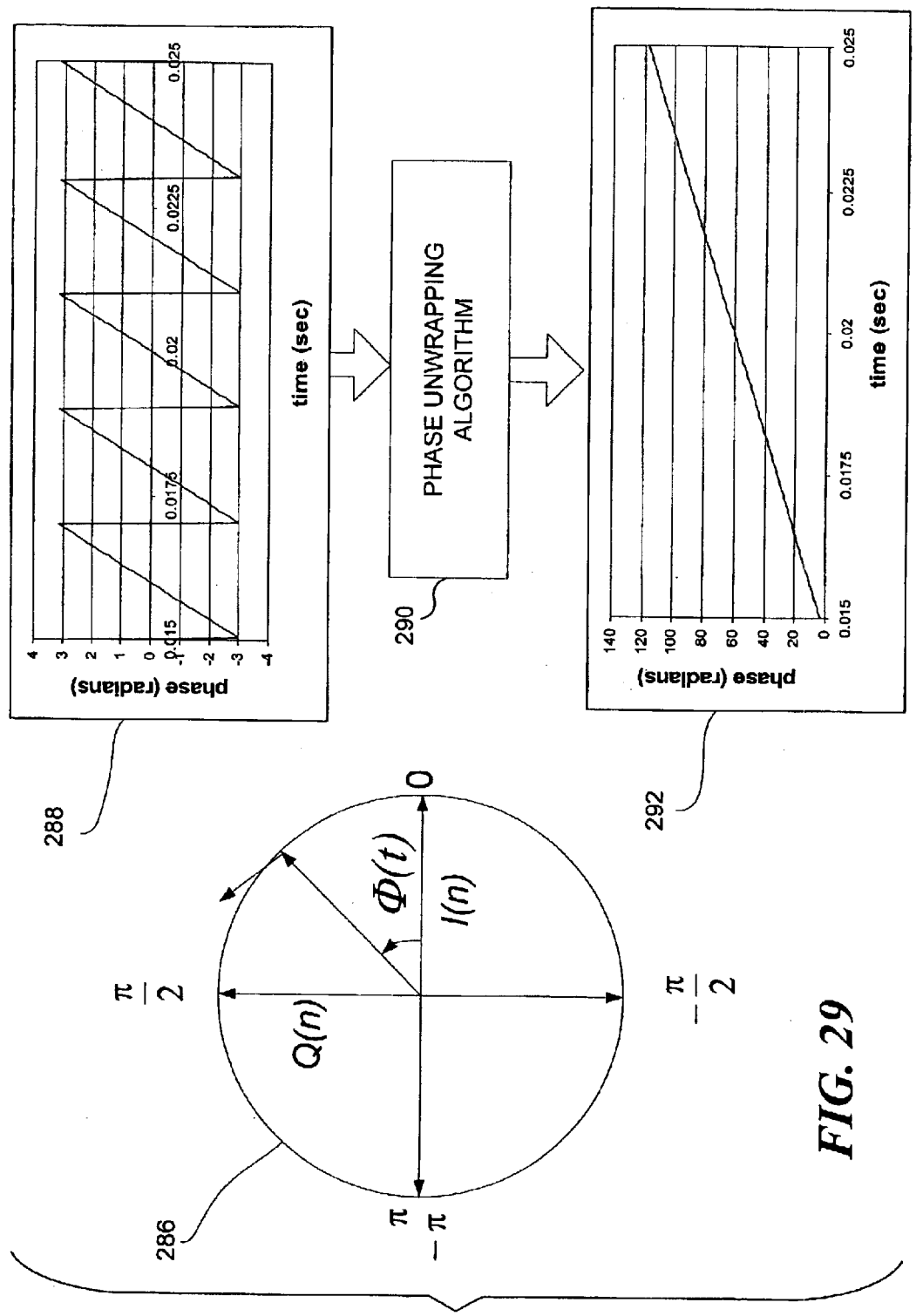
Figure 30:
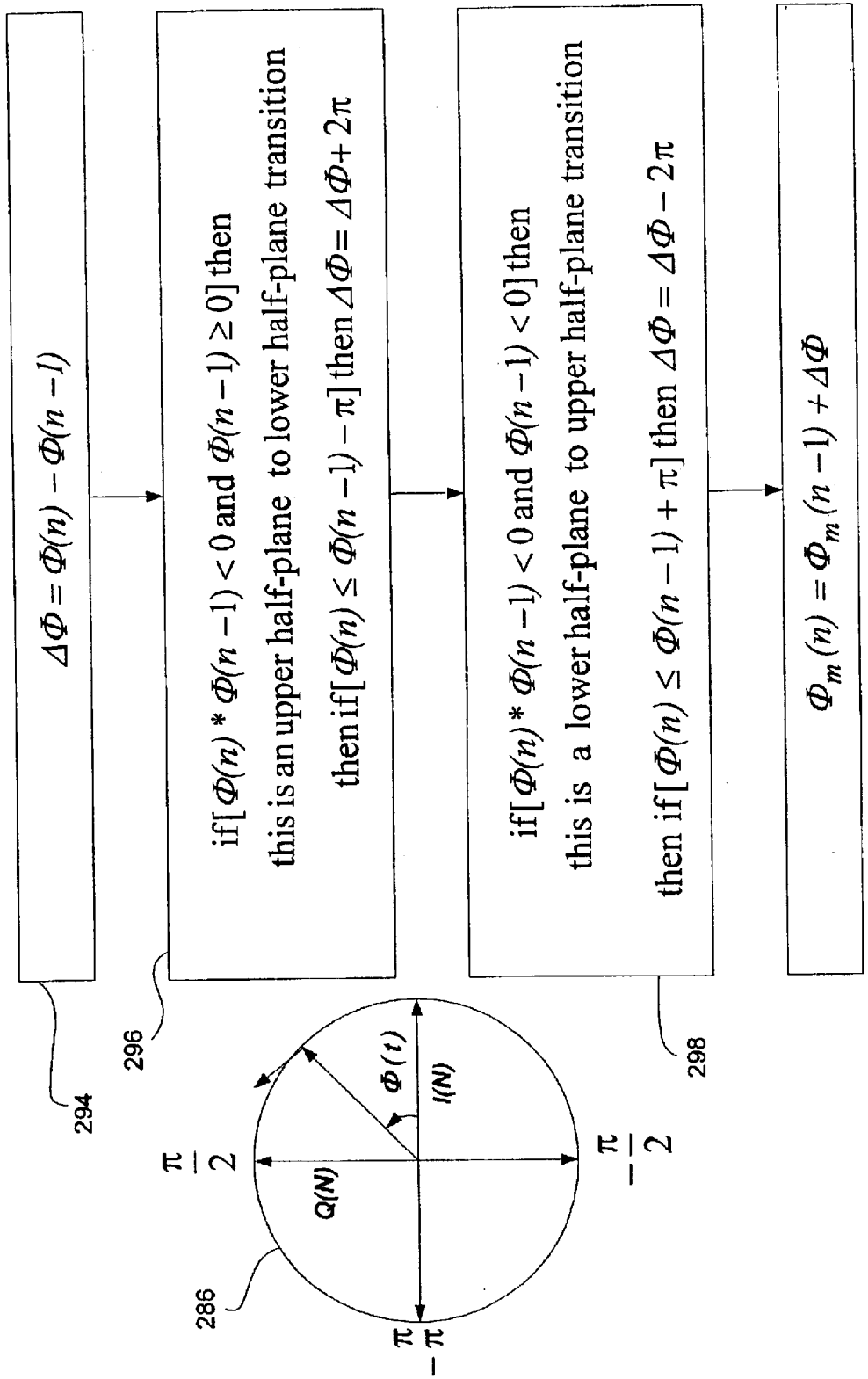
Figure 31A:
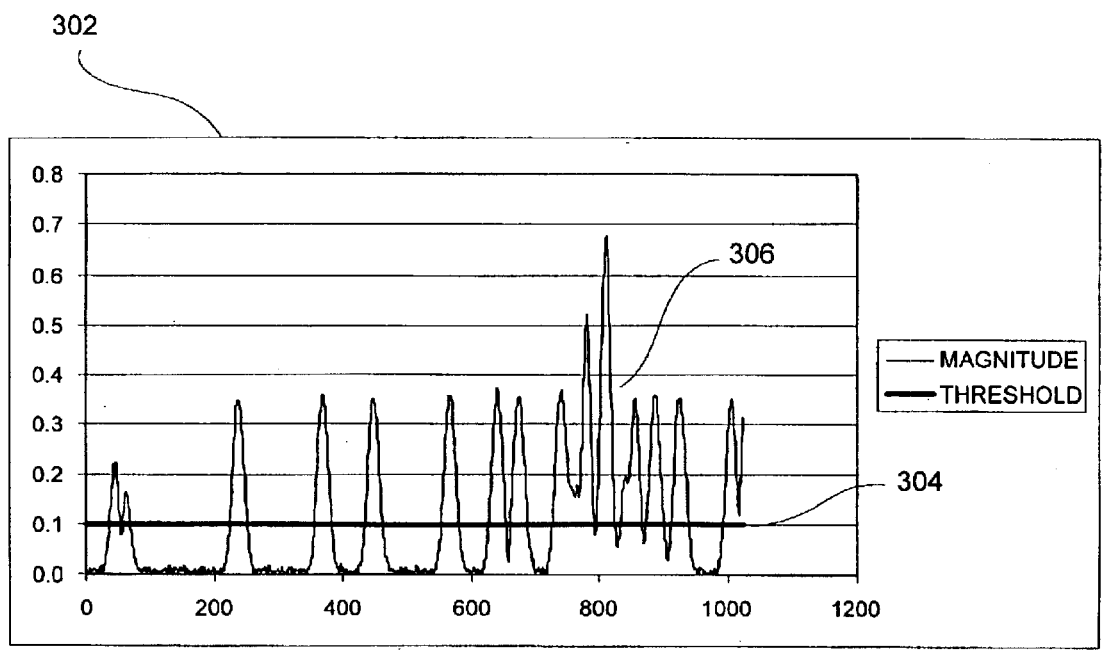
Figure 31B:
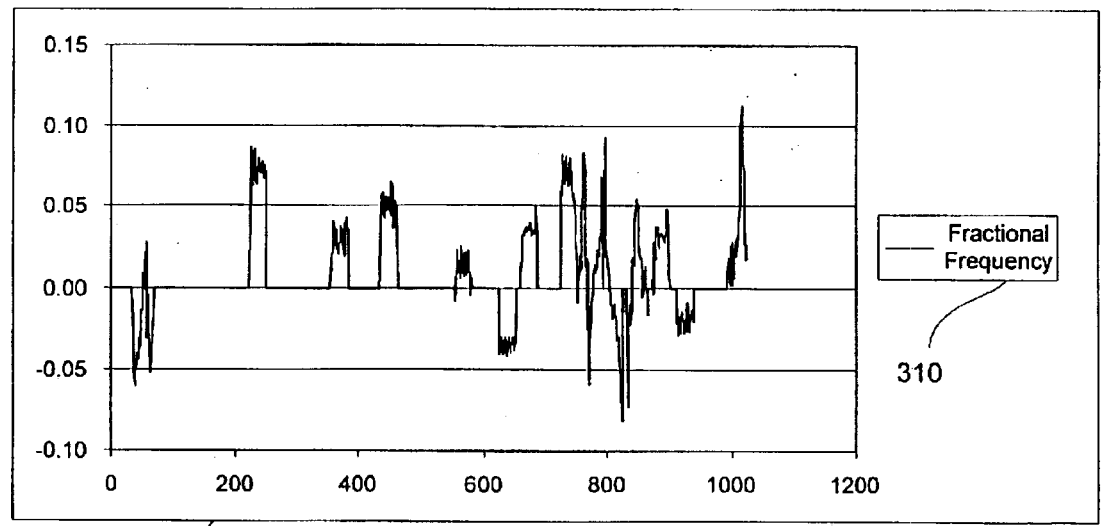
Figure 32:
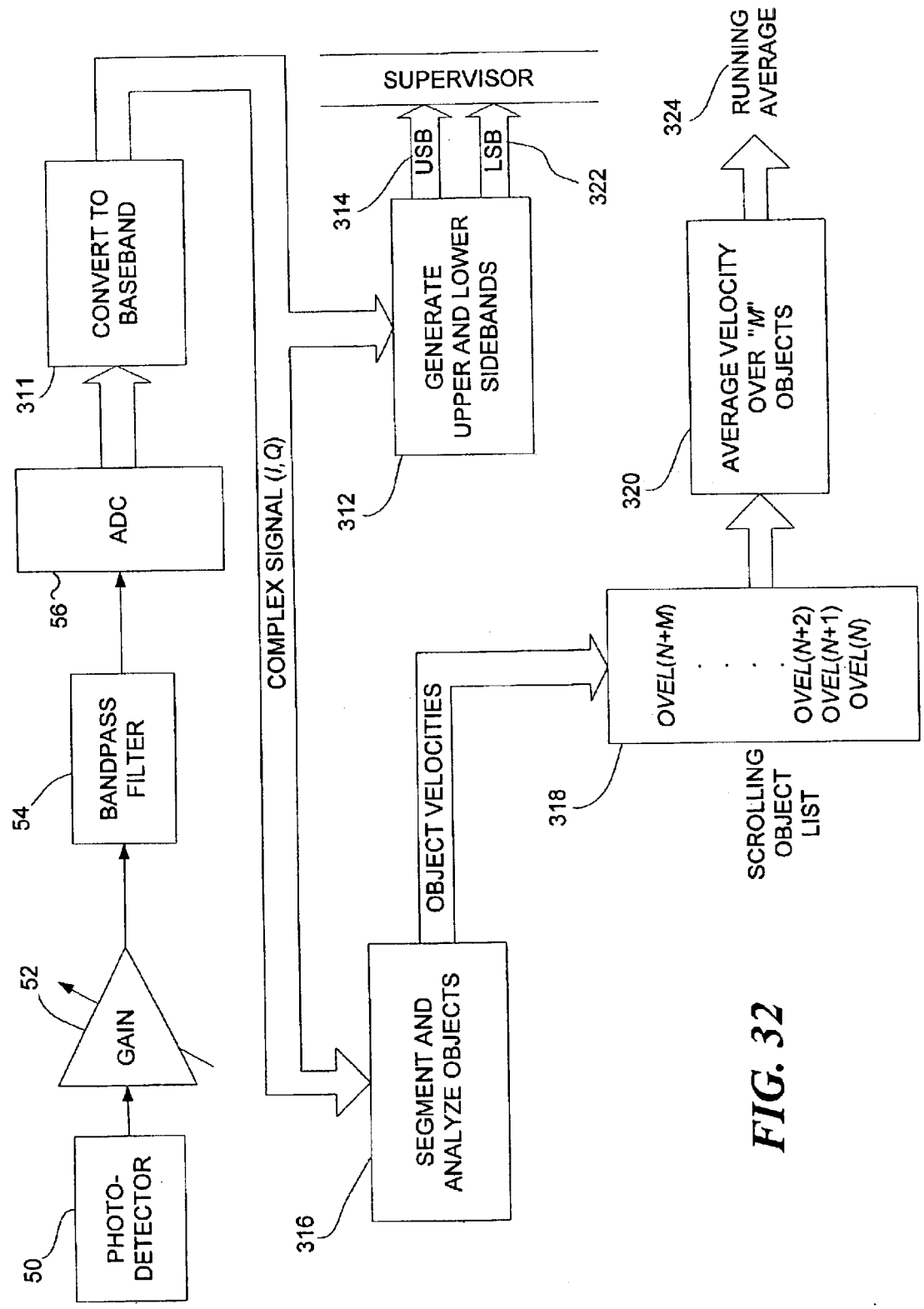
Figure 33:
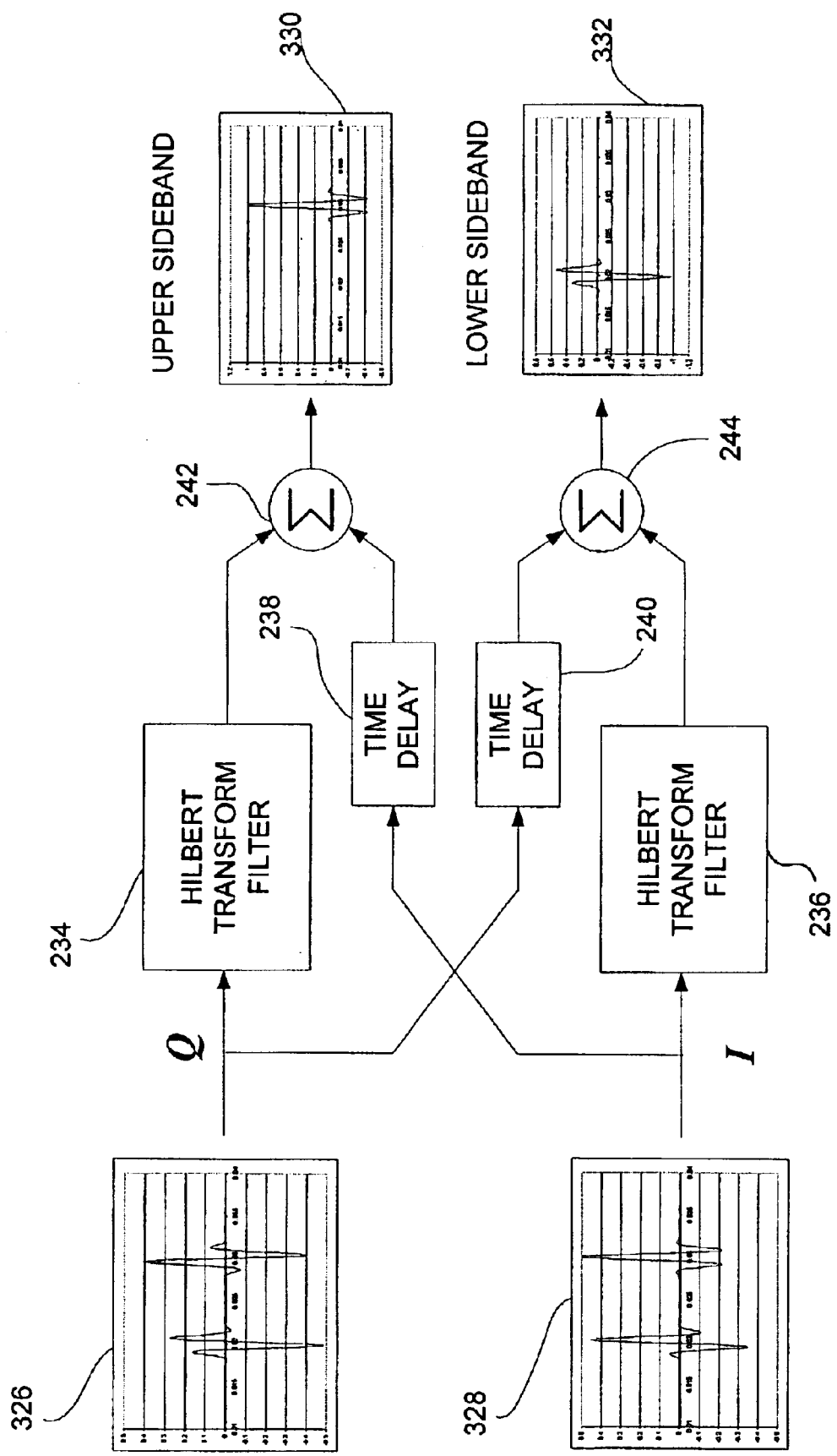
Figure 34:
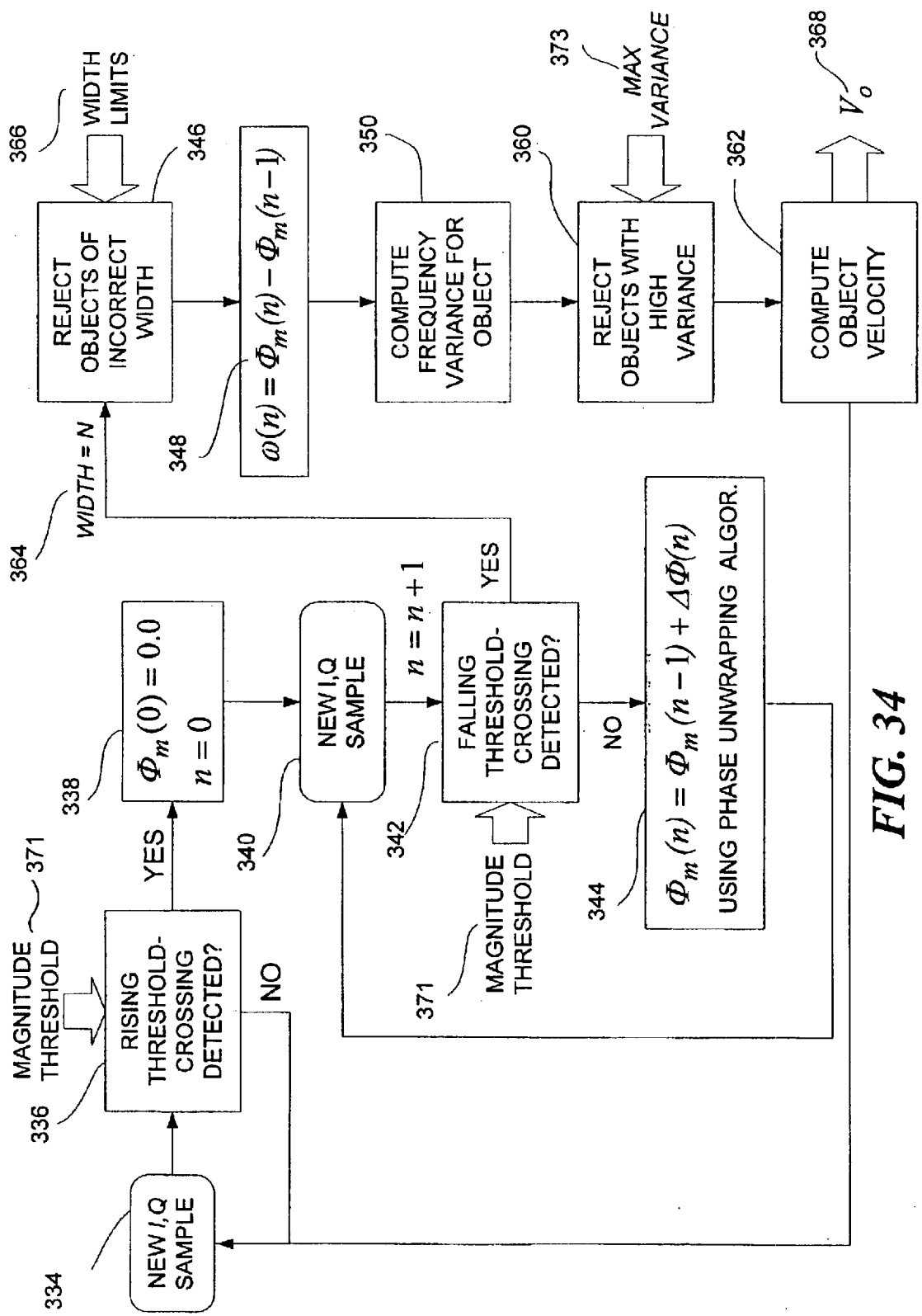
Figure 35A:
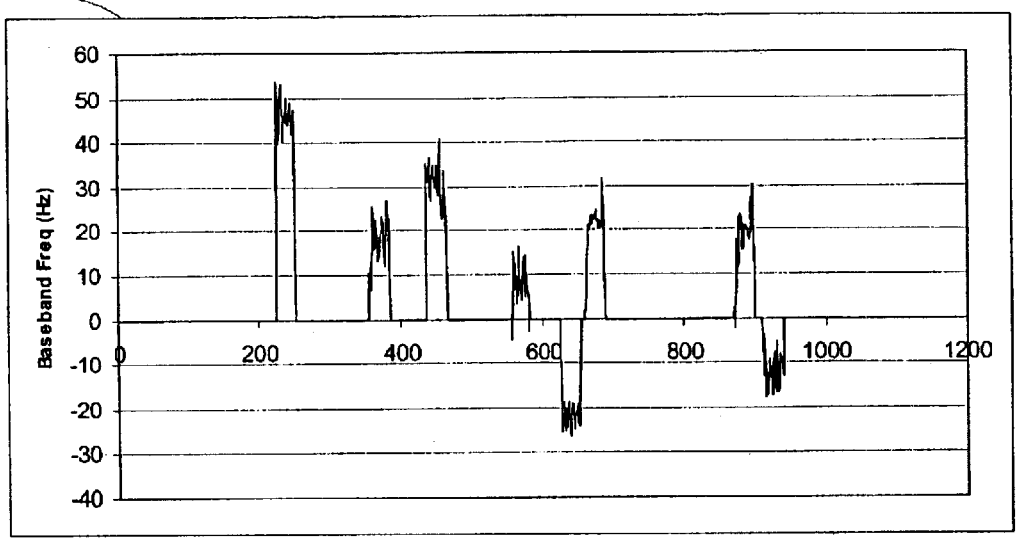
Figure 35B:
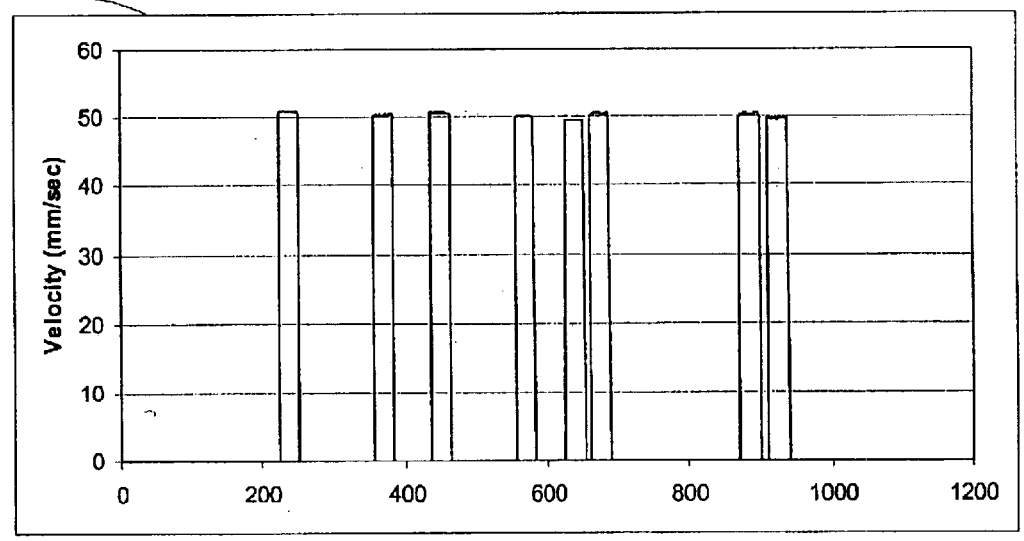
Figure 36:
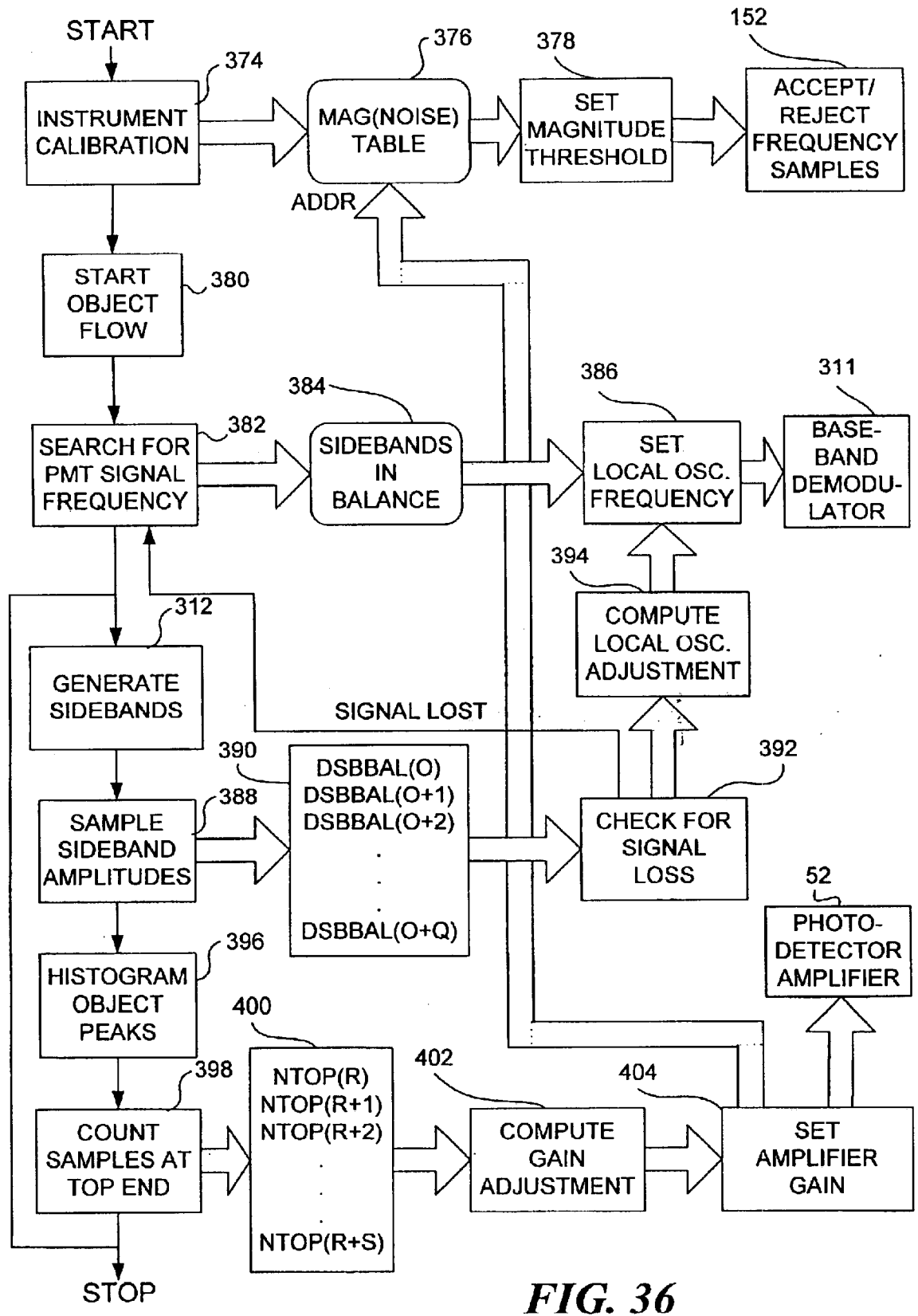
Figure 37:
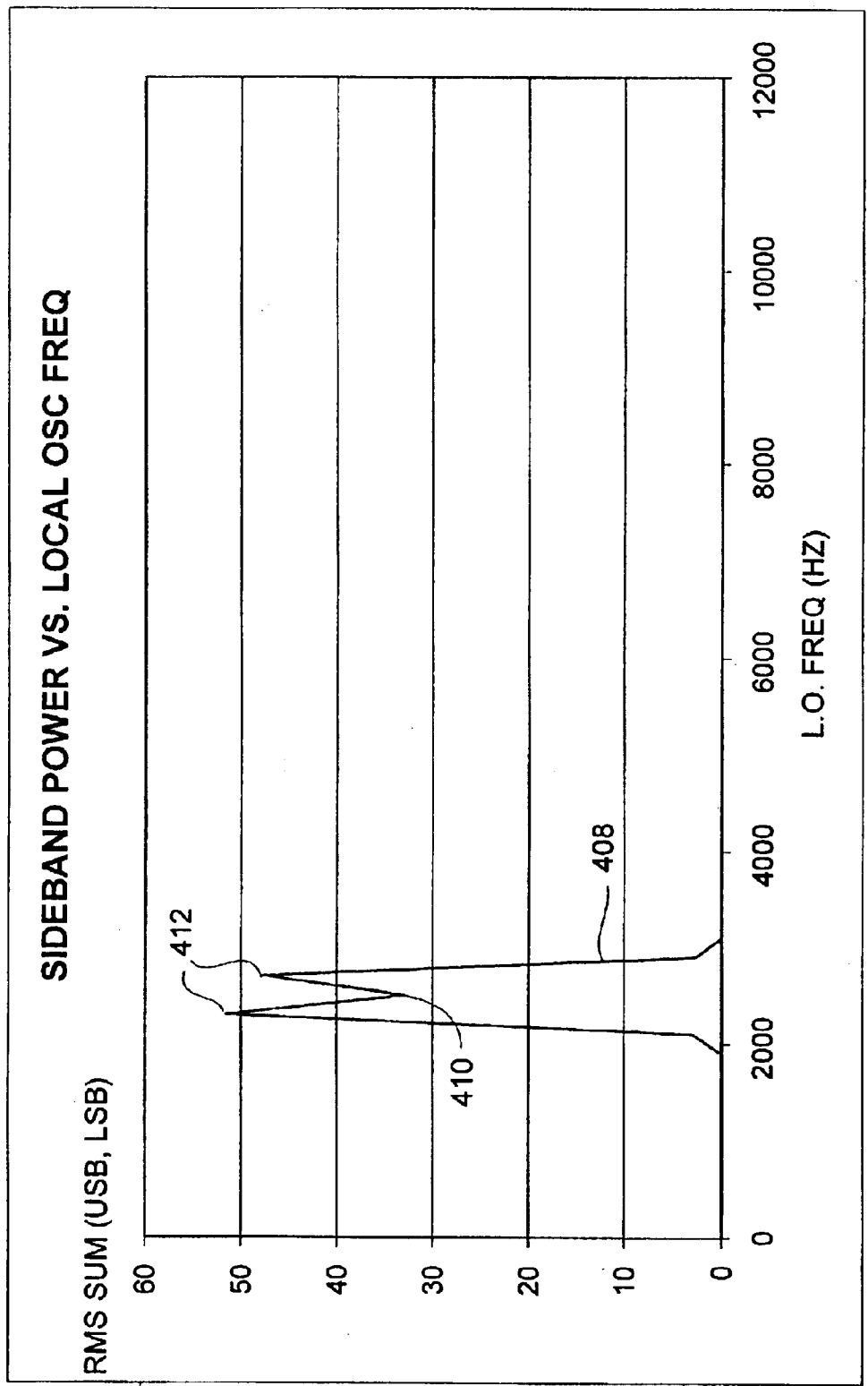
Figure 38:
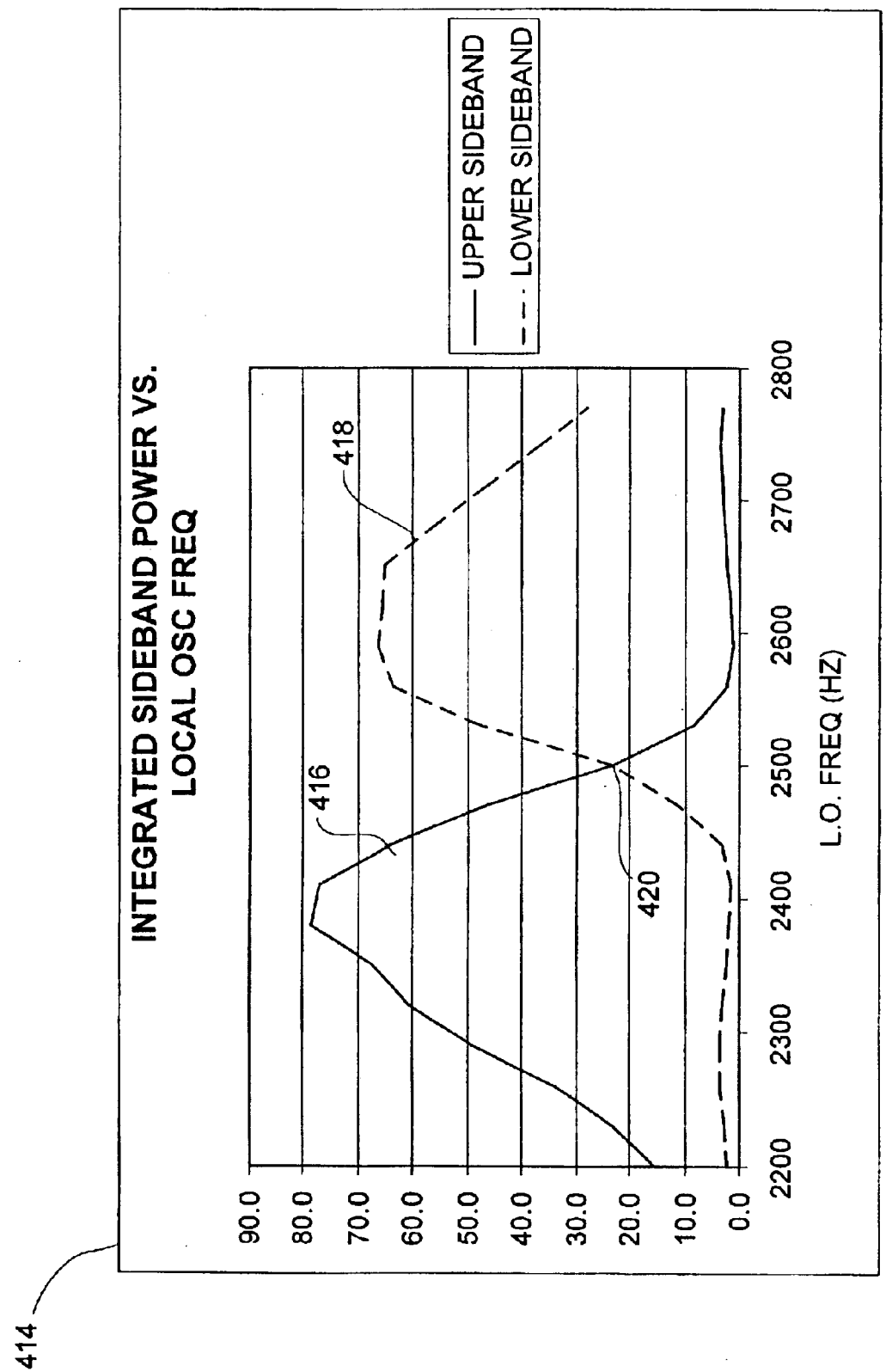
Figure 39:
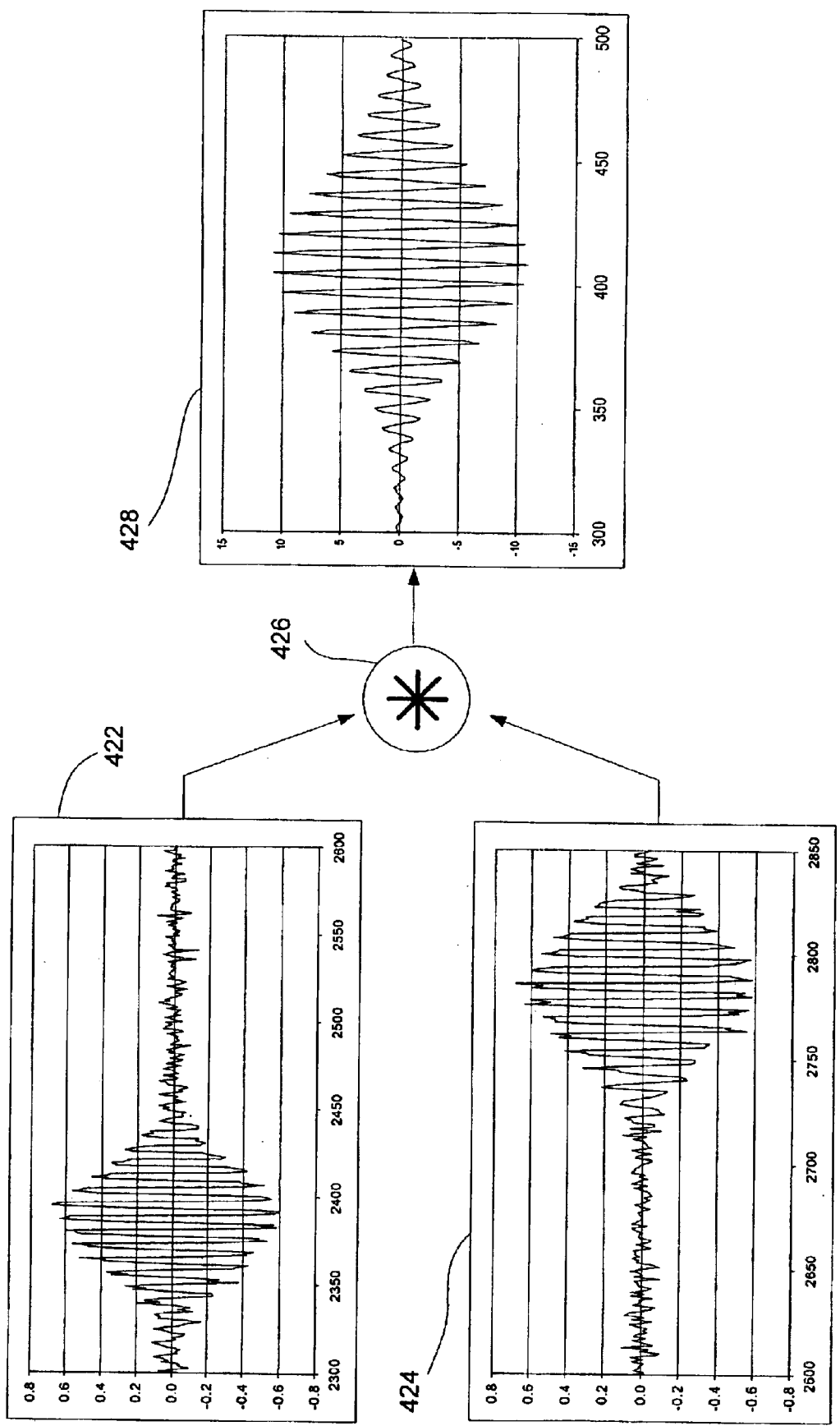
Figure 40:
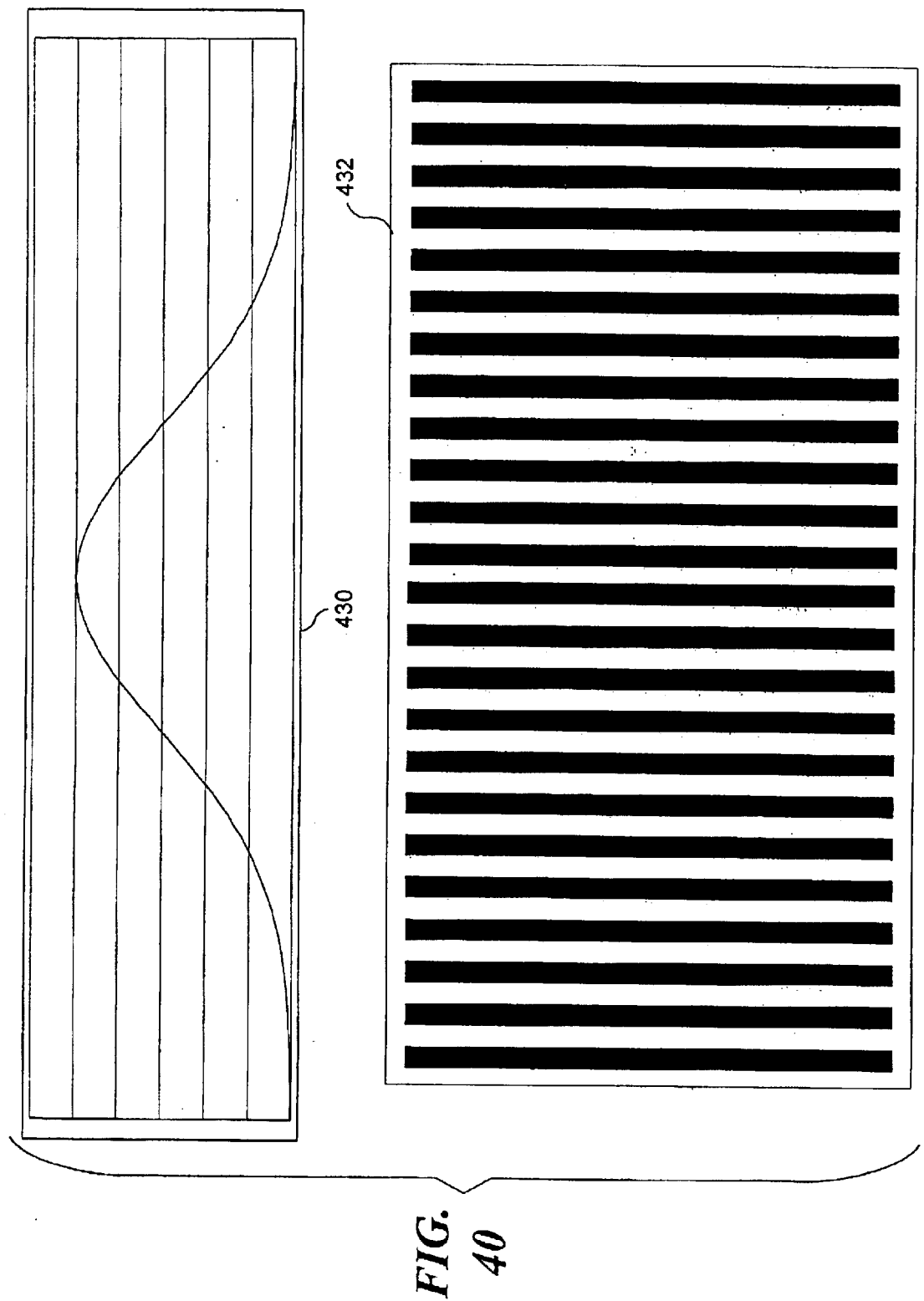
Figure 41:
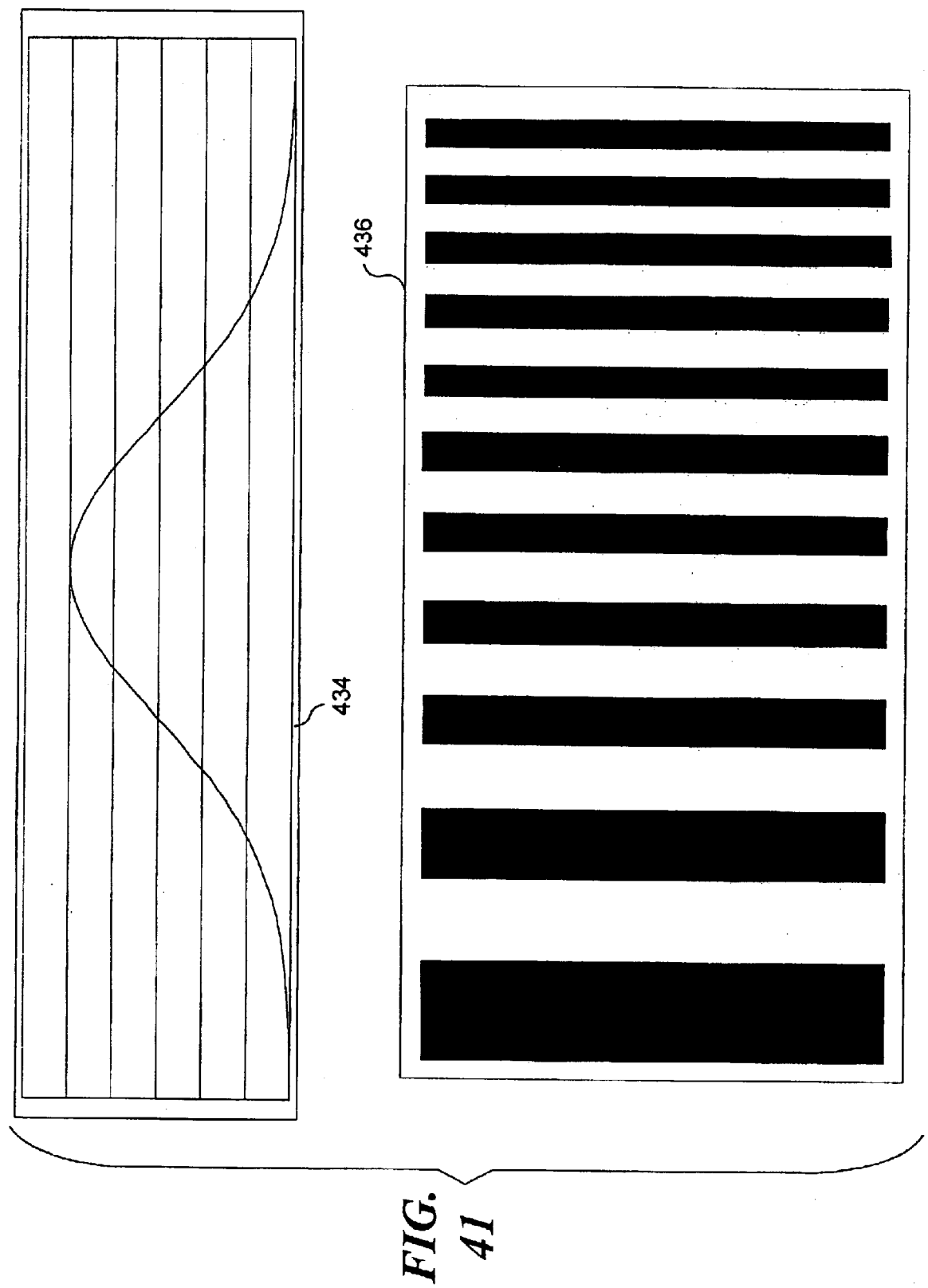
Figure 42:
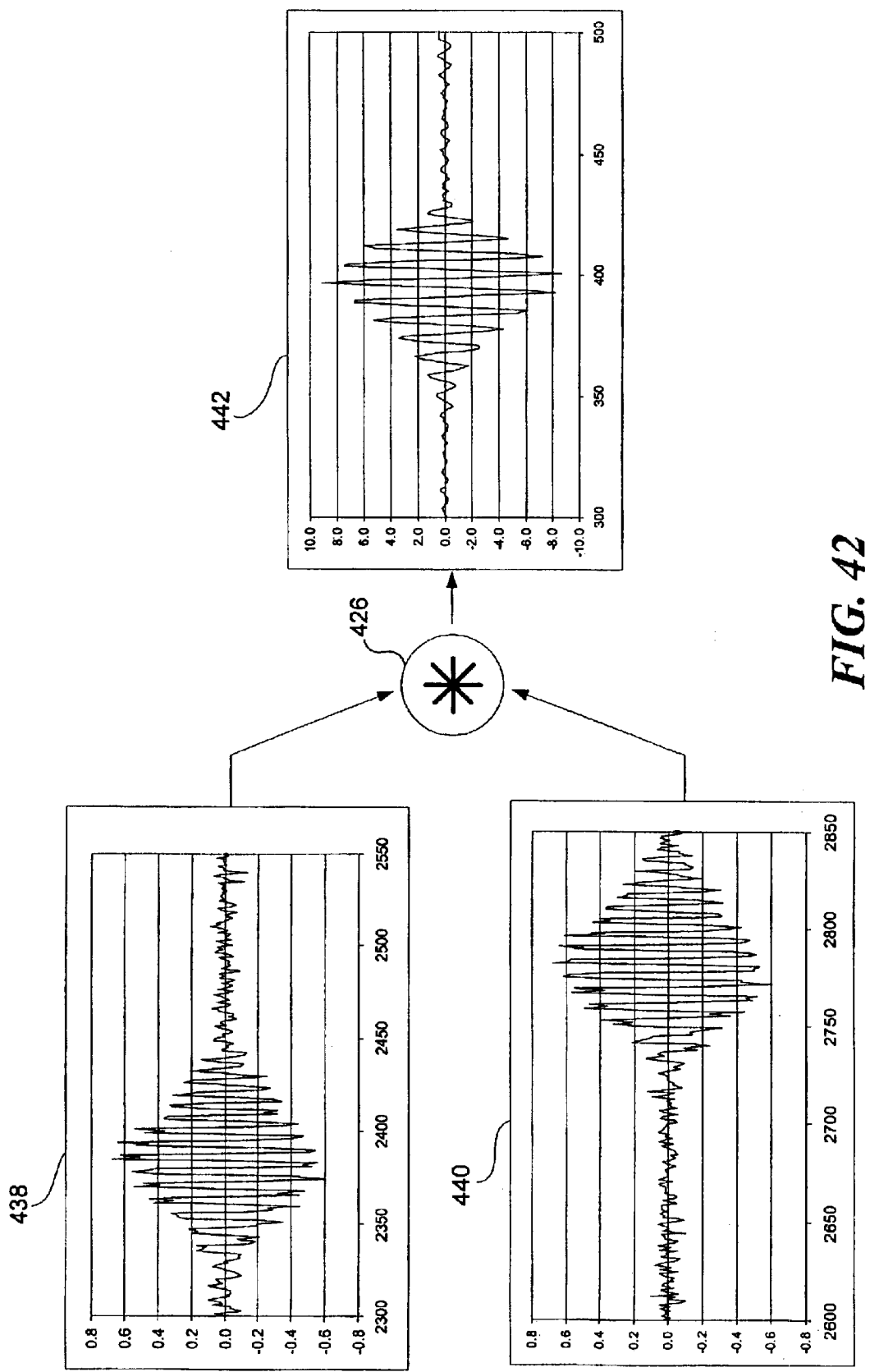
Figure 43:
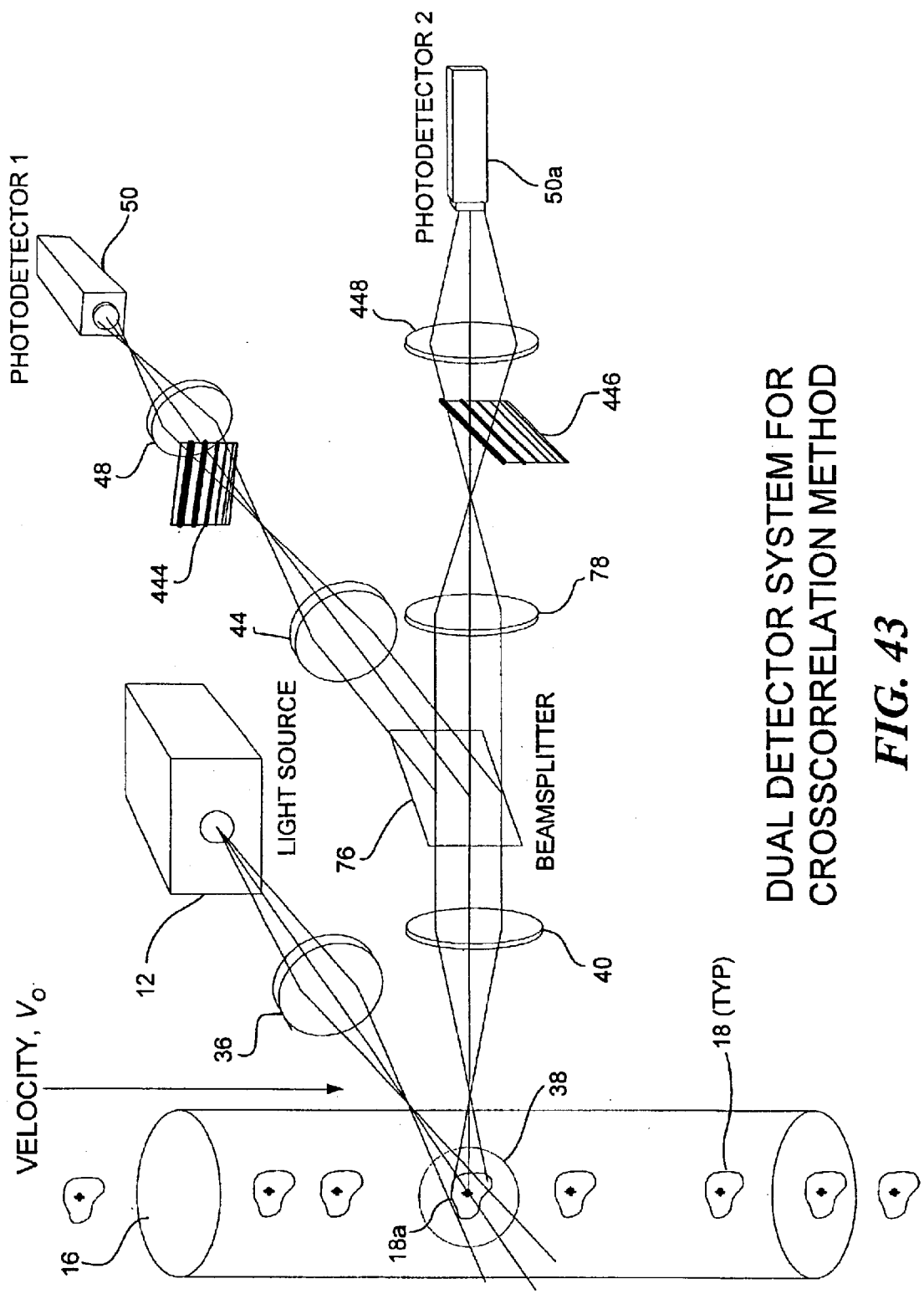
Figure 44:
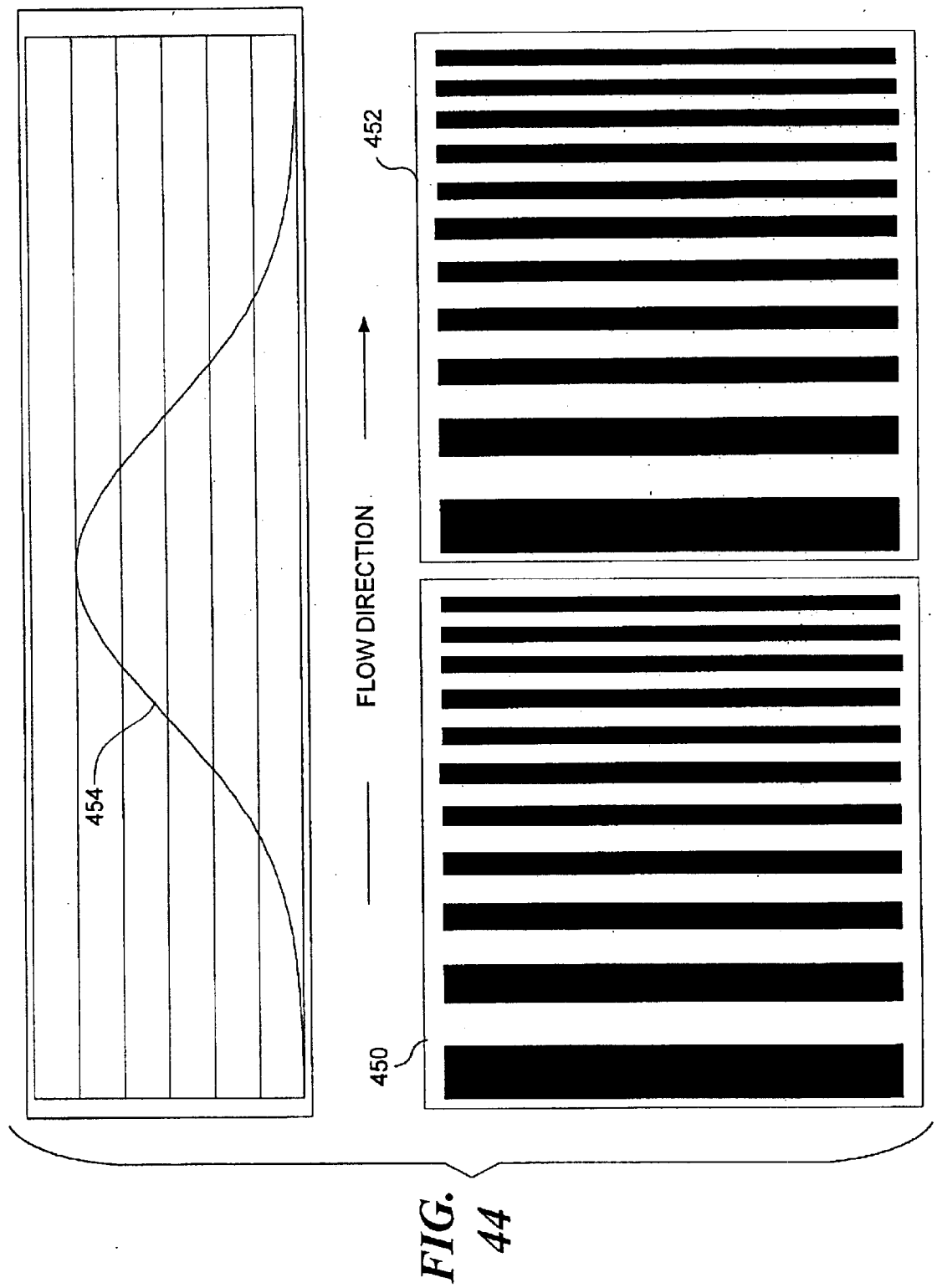
Figure 45:
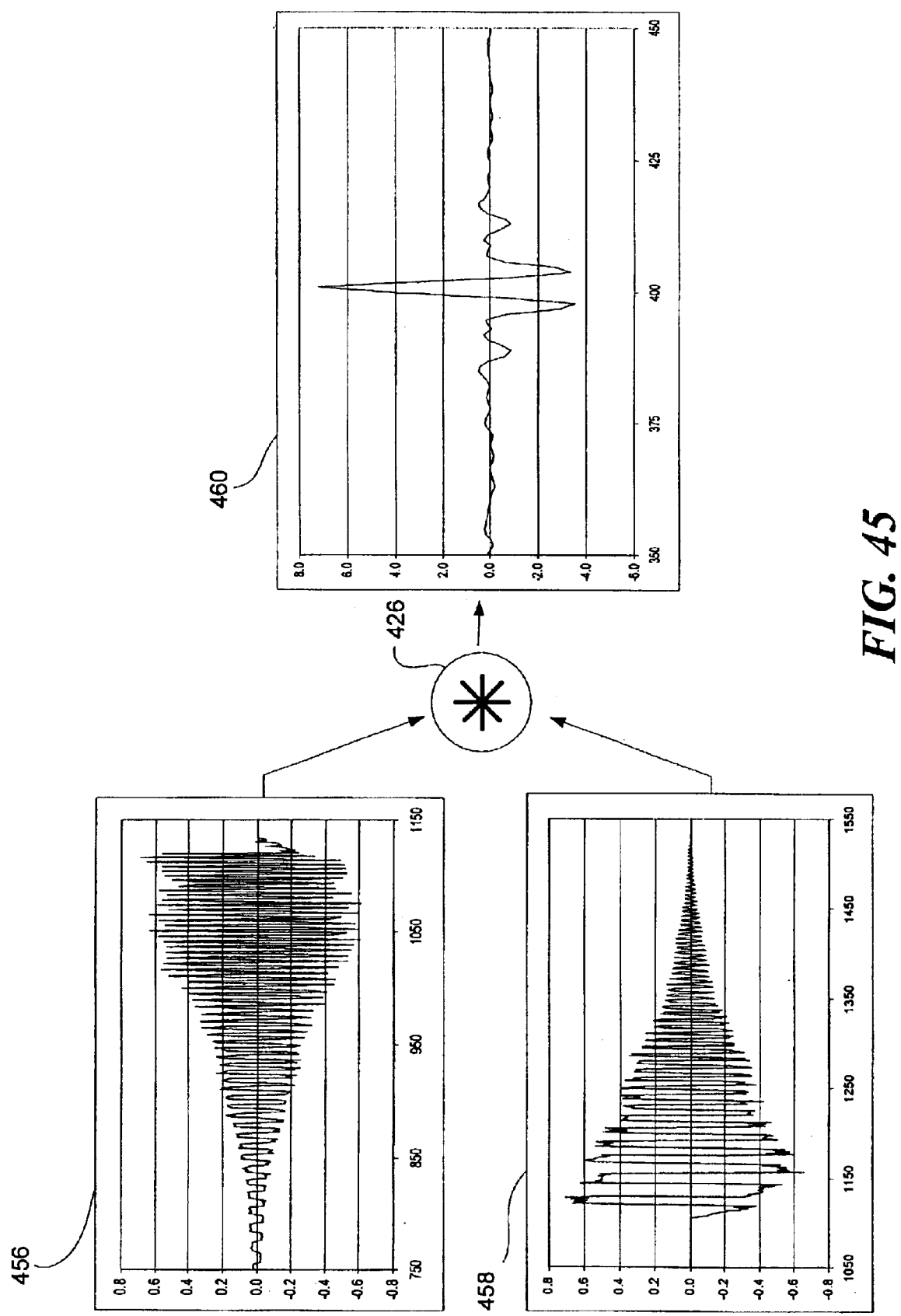
Figure 46:
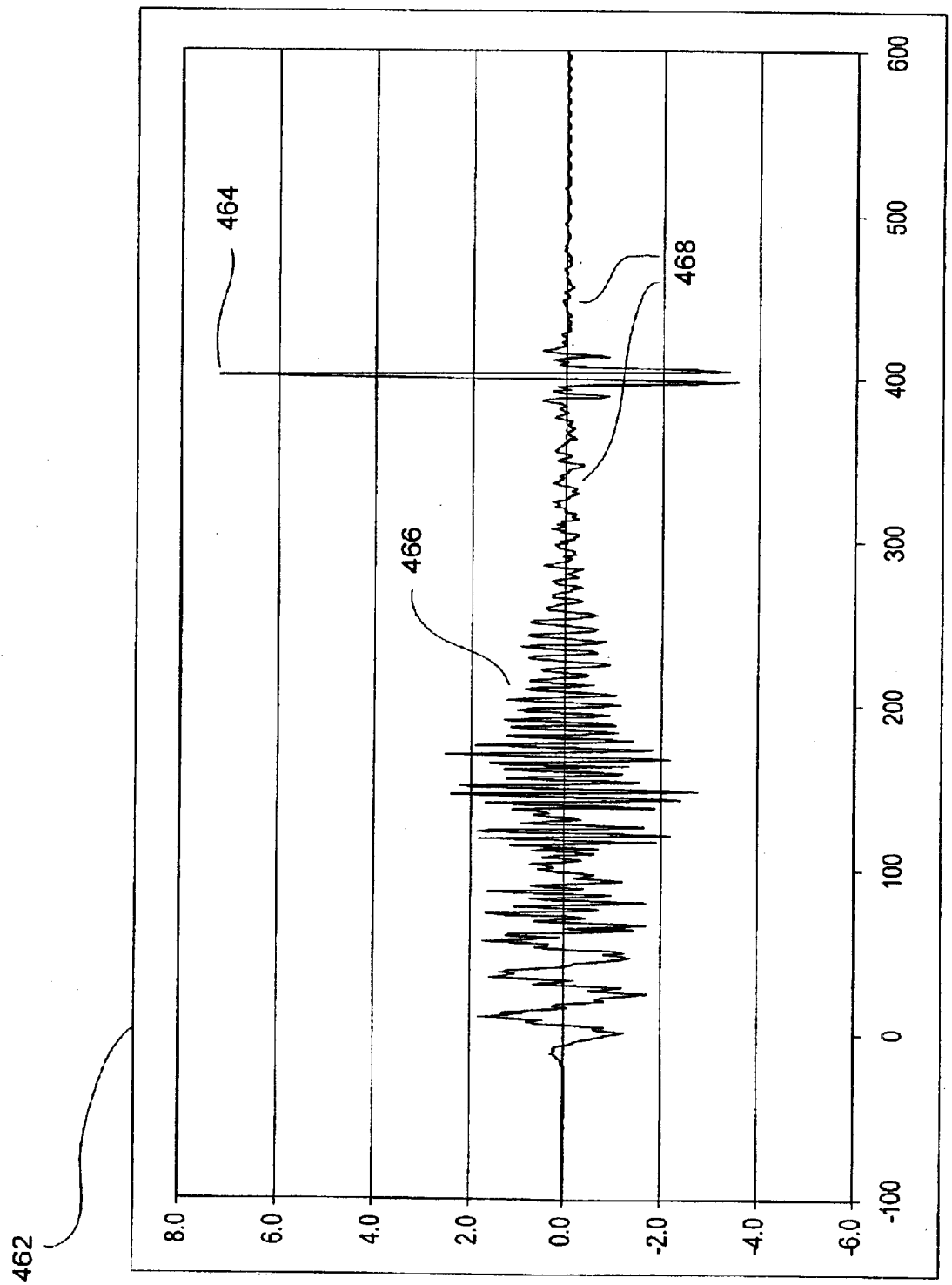
Figure 47:
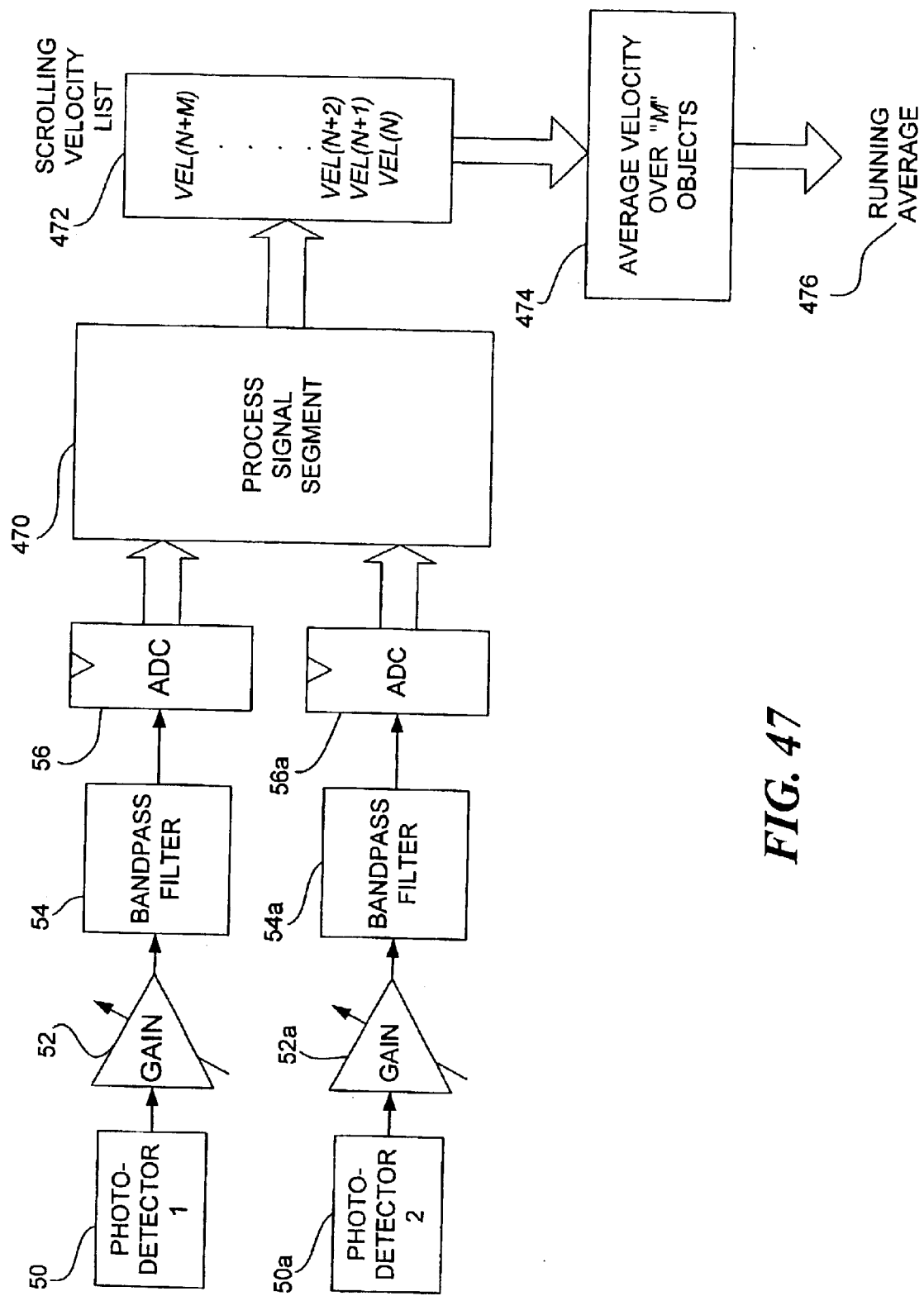
Figure 48:
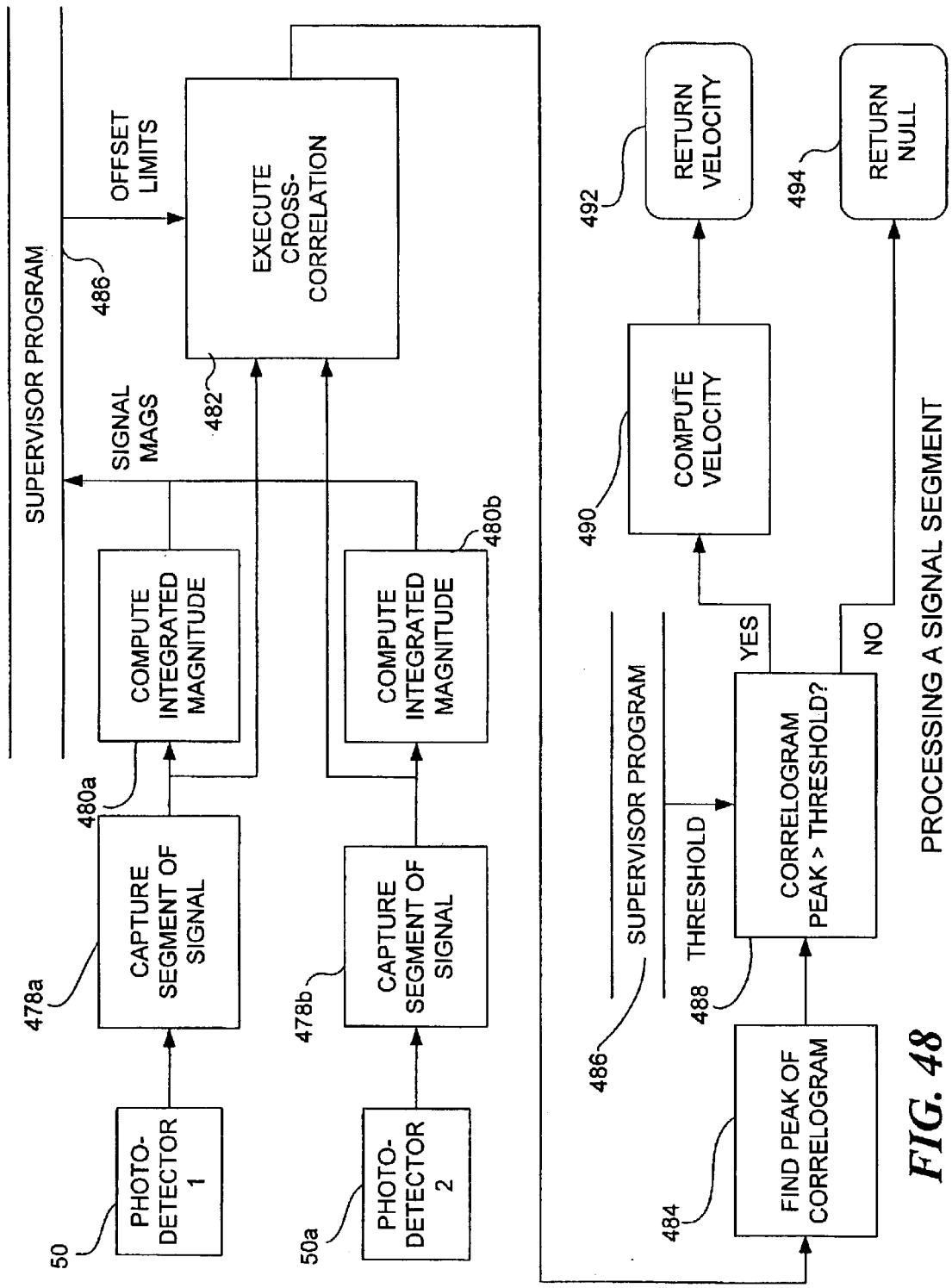
Figure 49:
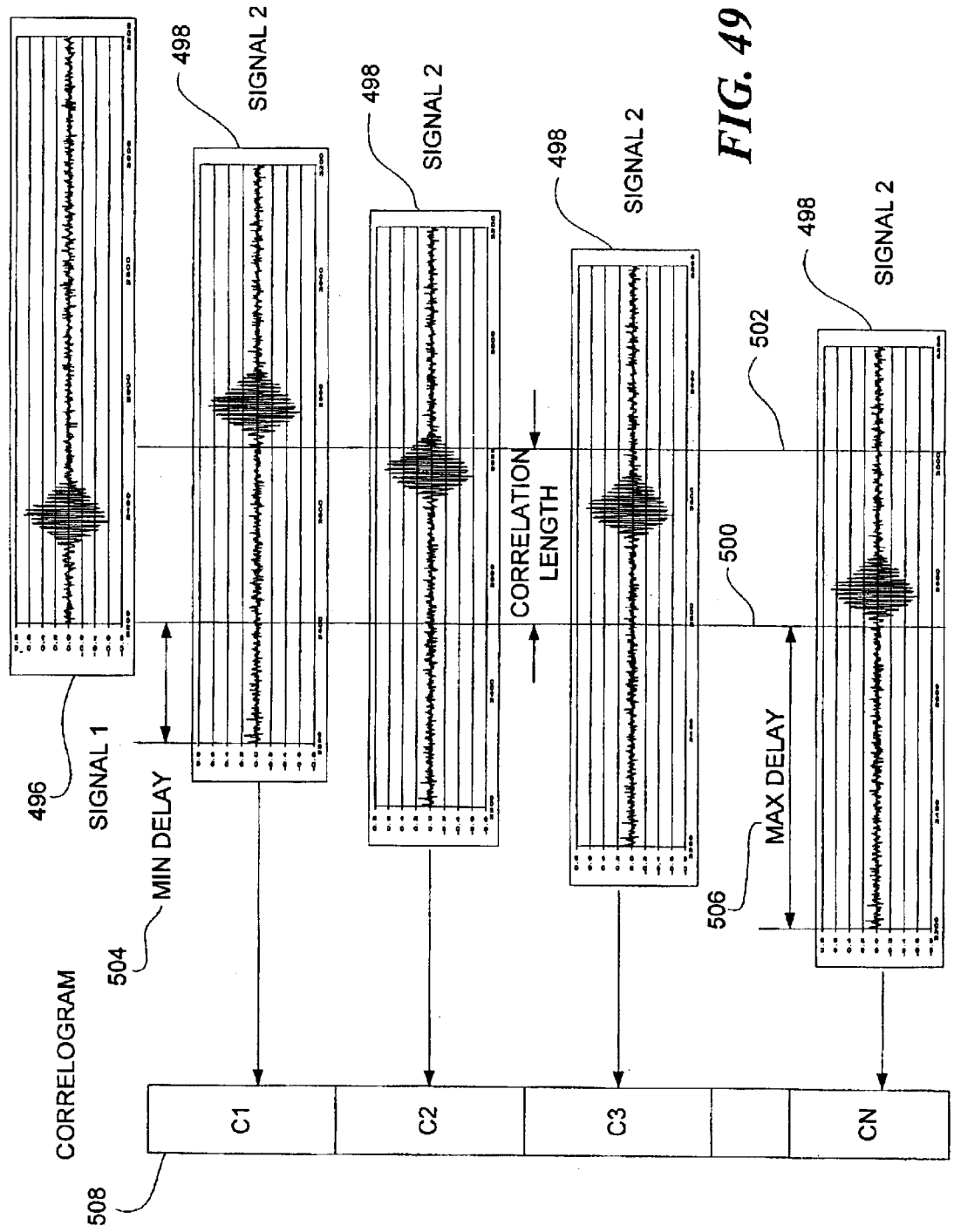
Figure 50:
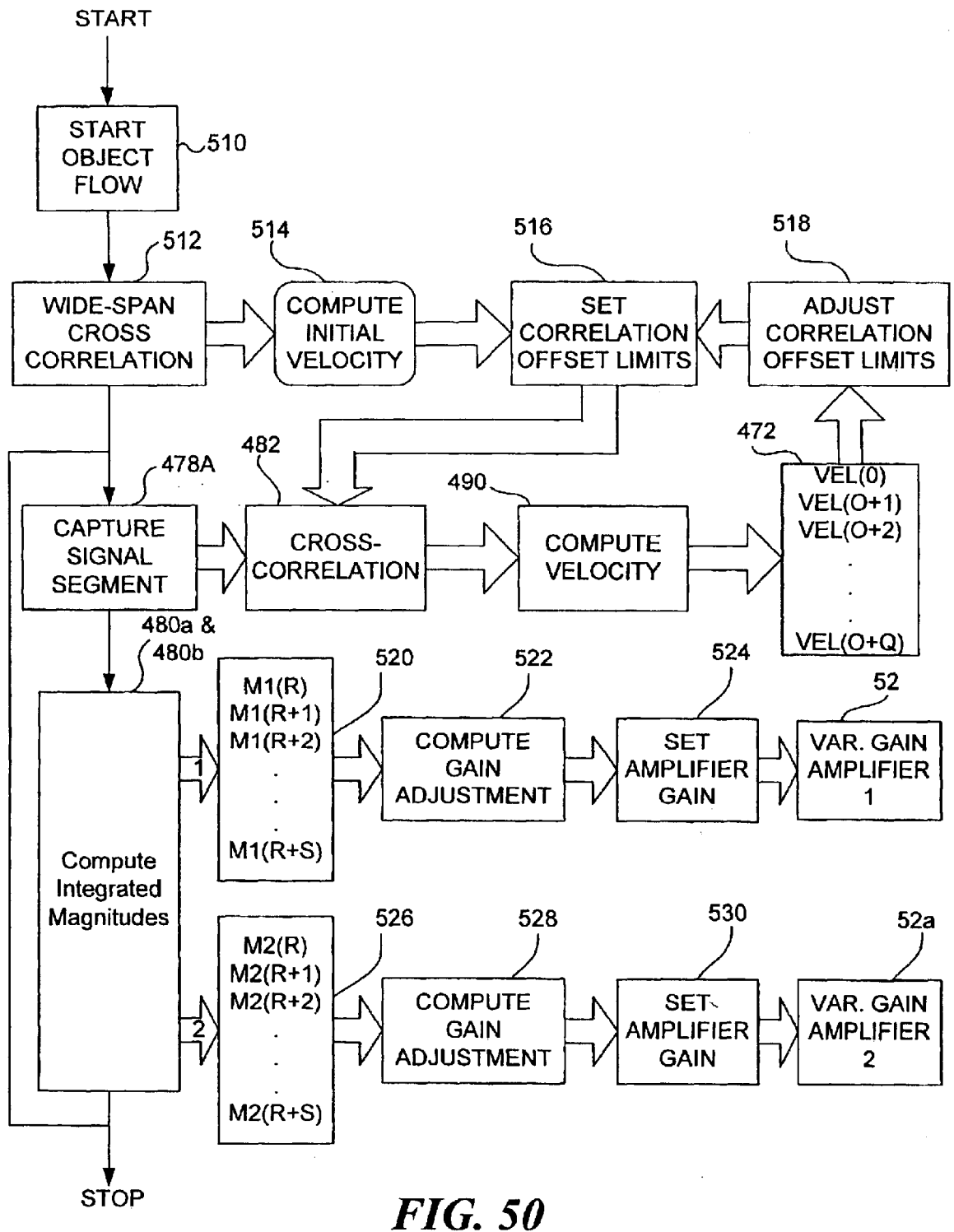
Figure 51:
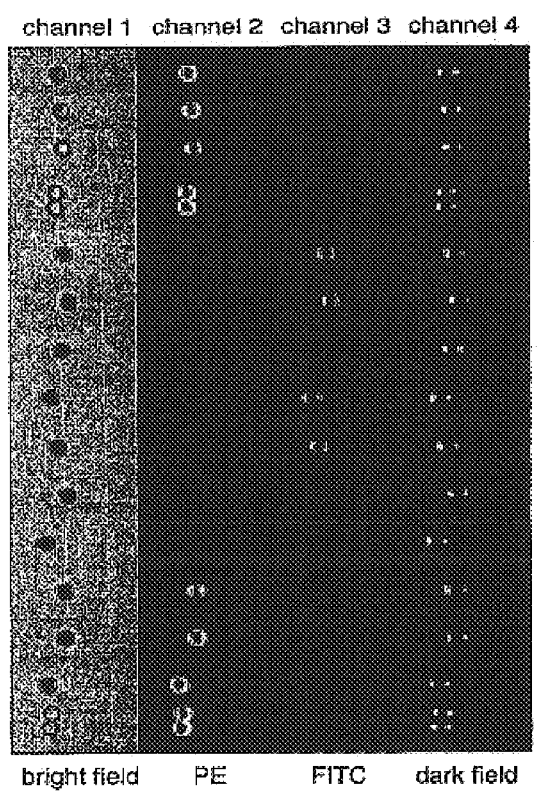
Figure 52:
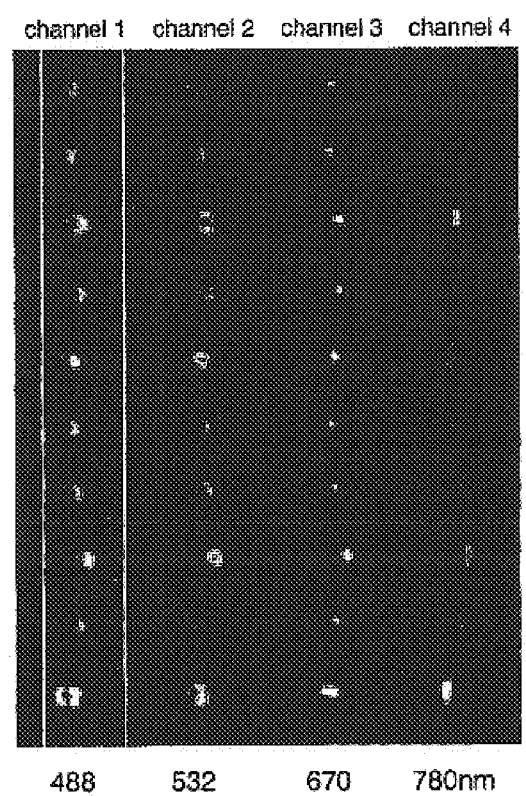
Figure 53:
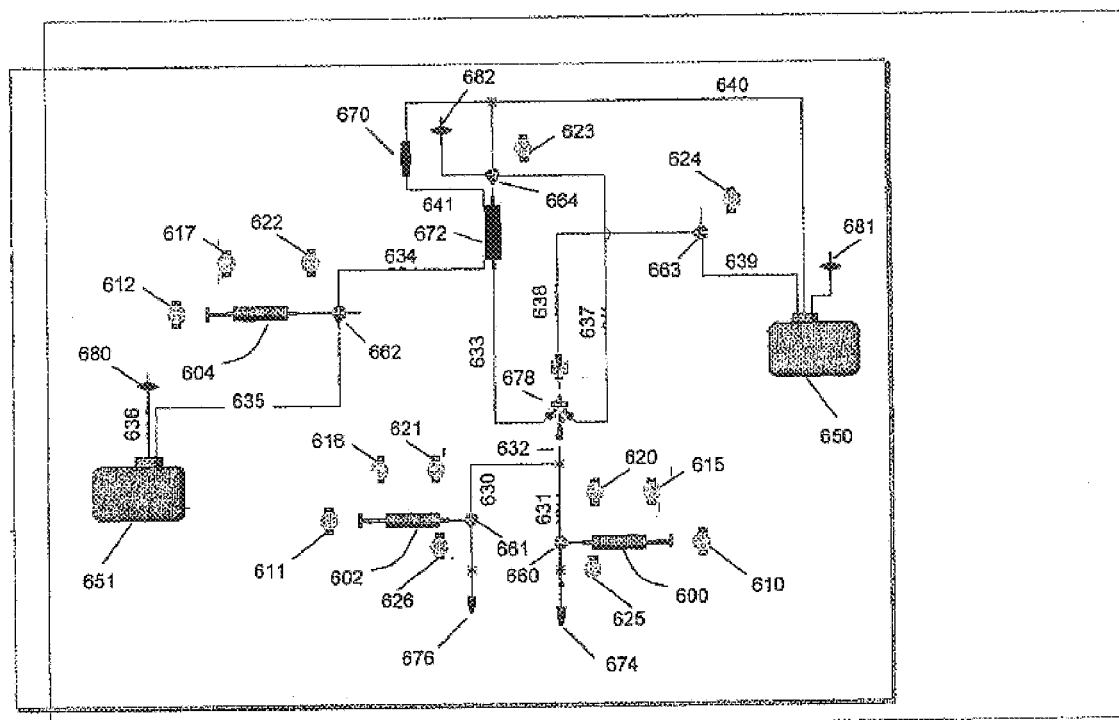
Figure 54:
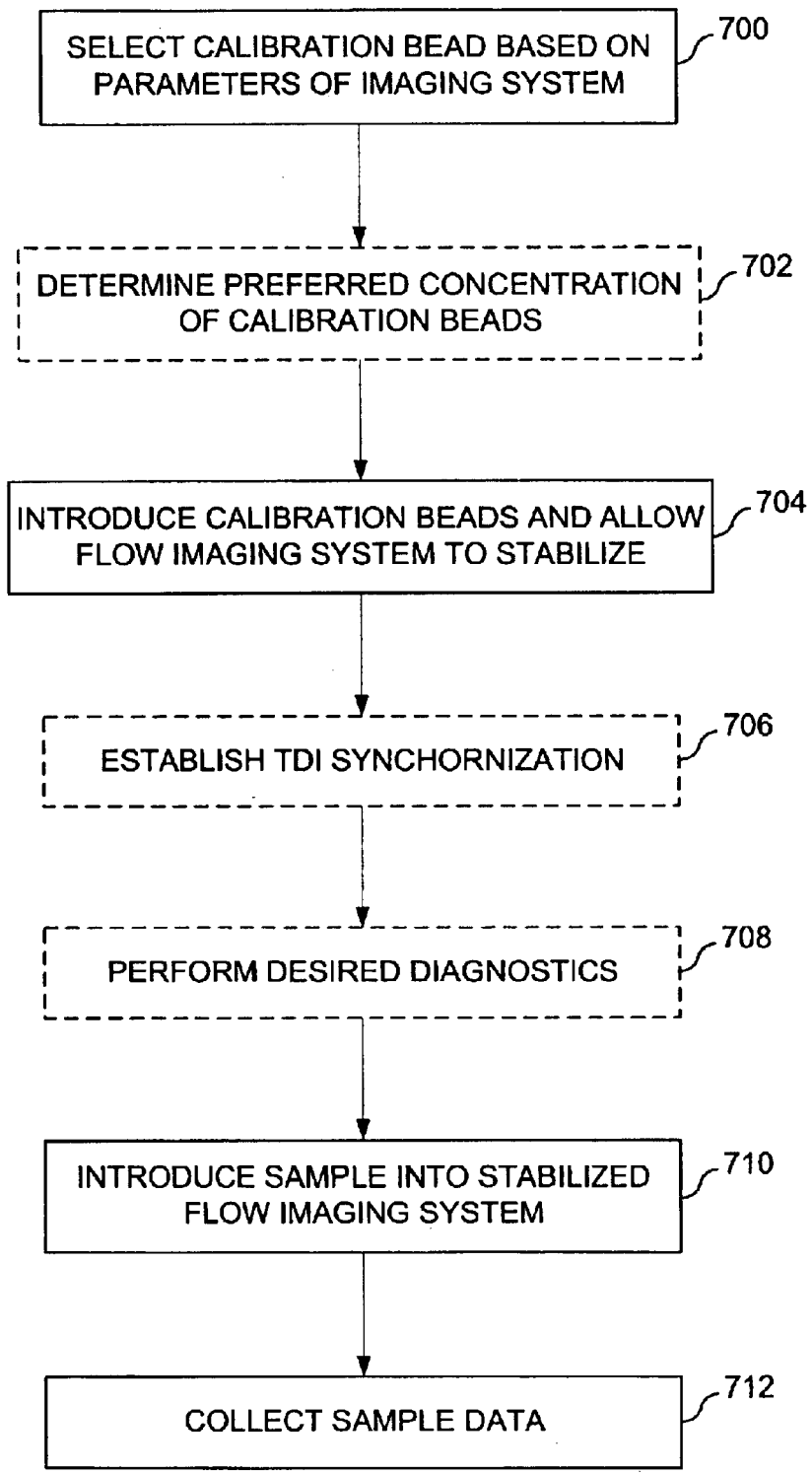

FIG. 26 schematically illustrates a modification of the spectrum of an exemplary photosensor signal by a baseband converter;

FIG. 27 schematically illustrates a modification of the spectrum of the exemplary photosensor signal of FIG. 26 by a baseband converter;

FIG. 28 schematically illustrates an analysis of the magnitude and phase series of the exemplary photosensor signal of FIG. 26 by computations on the I and Q baseband signals;

FIG. 29 schematically illustrates an application of a phase unwrapping algorithm to the phase series of the exemplary photosensor signal of FIG. 26, to provide a monotonic phase series;

FIG. 30 is a block diagram illustrating the steps employed in the phase unwrapping algorithm;

FIG. 31A is a graph showing a magnitude threshold being applied to a signal representing the monotonic phase series of FIG. 29, to reduce the effects of random noise;

FIG. 31B is a graph showing the result of employing the magnitude threshold of FIG. 31A before computing the fractional frequency from the monotonic phase series of FIG. 29;

FIG. 32 is a block diagram of the signal processing and velocity computation steps for the third embodiment of the present invention;

FIG. 33 schematically illustrates a computational modification of the spectrum of I and Q baseband signals to provide upper and lower sideband signals;

FIG. 34 is a block diagram illustrating the steps comprising segmentation and analysis of objects for the third embodiment of the present invention;

FIG. 35A is a graph illustrating the summation of the baseband frequency and the local oscillator frequency;

FIG. 35B is a graph illustrating the conversion of the sum of FIG. 35A to a velocity;

FIG. 36 is a block diagram illustrating the steps employed by a supervisory program for controlling the third embodiment of the present invention;

FIG. 37 is a graph of the sum of the upper sideband power and the lower sideband power for a broad sweep of the local oscillator frequency;

FIG. 38 is a graph showing the transition of power from the upper sideband to the lower sideband for a narrow sweep of the local oscillator;

FIG. 39 schematically illustrates the convolution of two signals generated by a conventional optical grating of uniform pitch;

FIG. 40 schematically illustrates the design of a conventional optical grating and its alignment to the Gaussian profile of the illumination beam;

FIG. 41 schematically illustrates the design of an optical grating with linearly swept pitch and its alignment to the Gaussian profile of the illumination beam;

FIG. 42 schematically illustrates the convolution of two signals generated by an optical grating having a linearly swept pitch;

FIG. 43 is a schematic diagram of a velocity measurement system using stacked gratings of nonuniform pitch, in accord with a fourth embodiment of the present invention;

FIG. 44 schematically illustrates the alignment of images of two gratings of nonuniform pitch relative to the Gaussian beam profile of the illumination beam;

FIG. 45 schematically illustrates the convolution of signals from two photosensors using the stacked nonuniform gratings of the fourth embodiment of the present invention;

FIG. 46 is a graph of an expanded correlogram for the signals generated by the stacked nonuniform gratings;

FIG. 47 is a block diagram broadly illustrating the steps required for signal processing and velocity computation in accord with the fourth embodiment of the present invention;

FIG. 48 is a block diagram illustrating detailed steps for the processing of a signal segment of the fourth embodiment of the present invention;

FIG. 49 schematically illustrates the concept of the convolution of a first signal by a second similar but delayed signal;

FIG. 50 is a block diagram illustrating the logical steps implemented by a supervisory program for controlling the fourth embodiment of the present invention;

FIG. 51 illustrates differently labeled calibration beads imaged by a preferred flow imaging system;

FIG. 52 illustrates calibration beads imaged by a preferred flow imaging system;

FIG. 53 is a schematic diagram illustrating a preferred fluidic system employed to introduce calibration into a flow imaging system in accord with the present invention; and FIG. 54 is a block diagram illustrating overall steps for using calibration beads to enhance the performance of a flow imaging system, in accord with the present invention.

DESCRIPTION OF THE PREFERRED EMBODIMENT

Overview of the Present Invention

It should be understood that the present invention relates to the use of calibration beads to enhance the performance and reliability of flow imaging systems, particularly flow imaging systems that employ TDI detectors and which require the synchronization of the TDI detectors to objects in flow. Details of the use of calibration beads can be found below in a section entitled "The use of calibration beads in flow imaging systems." In order to provide an understanding of preferred imaging systems, and preferred methods of determining the velocity of objects in flow in such imaging systems, the following descriptive text, relating to FIGS. 1–50, is provided. If the reader desires, he may proceed to the descriptive text relating to FIGS. 51–53, which relate specifically to the use of calibration beads.

Preferred Flow Imaging Systems and Preferred Velocity Determination

In the present invention, moving objects are illuminated and light from the objects is imaged onto a detector after passing though an optical grating. The optical grating comprises a plurality of transparent and opaque bars that modulate the light received from the object, producing modulated light having a frequency of modulation that corresponds to the velocity of the object from which the light was received. Preferably, the optical magnification and the ruling pitch of the optical grating are chosen such that the bars are approximately the size of the objects being illuminated. Thus, the light collected from cells or other objects is alternately blocked and transmitted through the ruling of the optical grating as the object traverses the interrogation region, i.e., the FOV. The modulated light is directed toward a light sensitive detector, producing a signal that can be analyzed by a processor to determine the velocity of the object.

The present invention has been developed as four distinct preferred embodiments. First and second embodiments employ a first optical grating and a frequency domain velocity measurement based signal processing technique. A third embodiment also employs the first optical grating, but uses a time domain velocity measurement (TDVM) based signal processing technique. A fourth embodiment employs the first and also includes a second optical grating to determine velocity using the time domain based signal processing technique. The differences in the first and second embodiments are that the first embodiment is specifically directed to analyzing objects that are deposited on a support that is moved through a FOV, while the second embodiment applies the same general processing technique to determine the velocity of objects that are entrained in a fluid flow through the FOV. Details of these specific embodiments are provided below, after a brief discussion of the concepts generally applicable to all of the embodiments.

Figure 1:
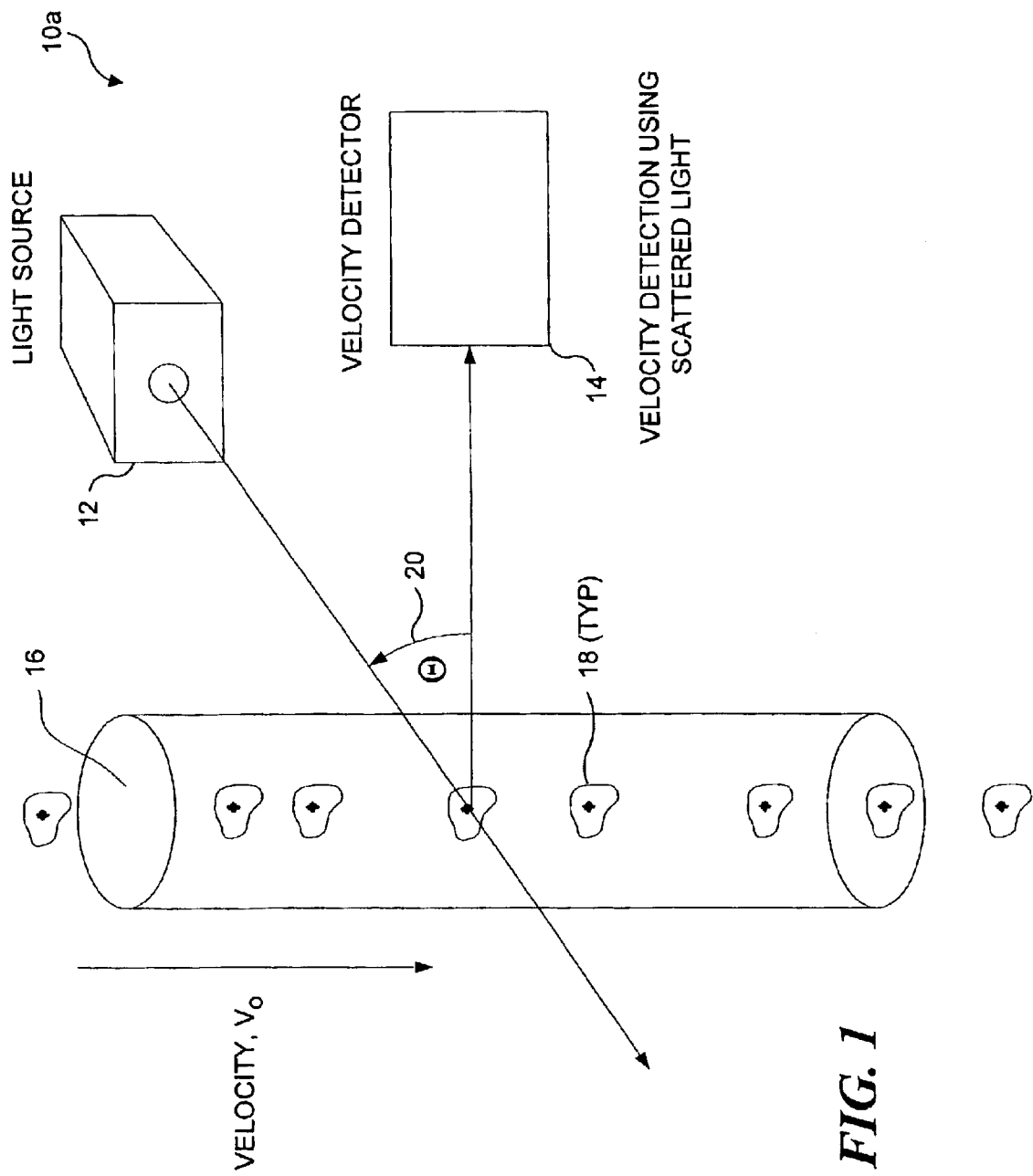
FIG. 1 is a schematic diagram of a system for measuring the velocity of objects in a flow stream by detecting light scattered by the objects.
Figure 2:
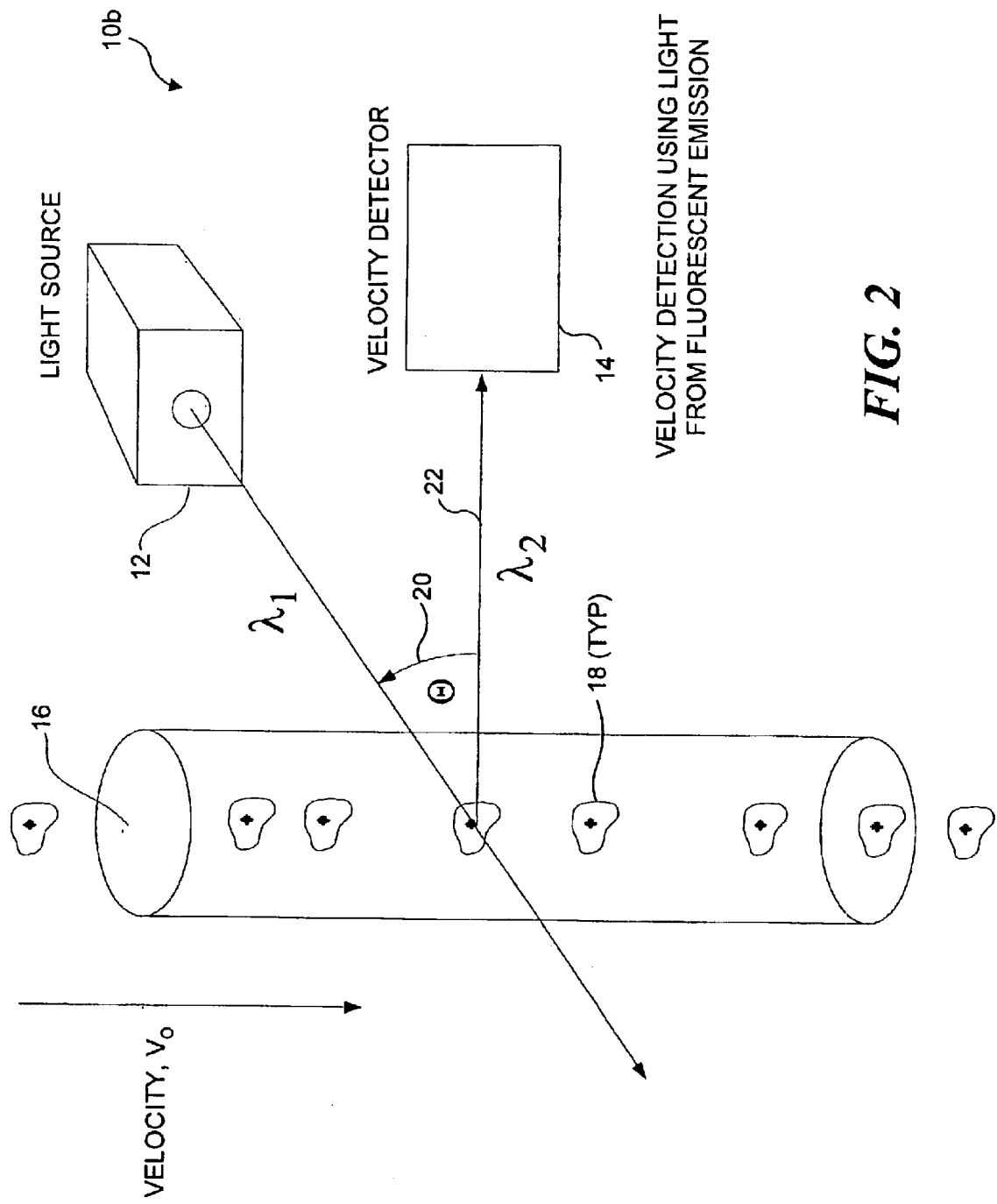
FIG. 2 is a schematic diagram of a system for measuring the velocity of objects in a flow stream by detecting light emitted by fluorescence by the objects.
Figure 3:
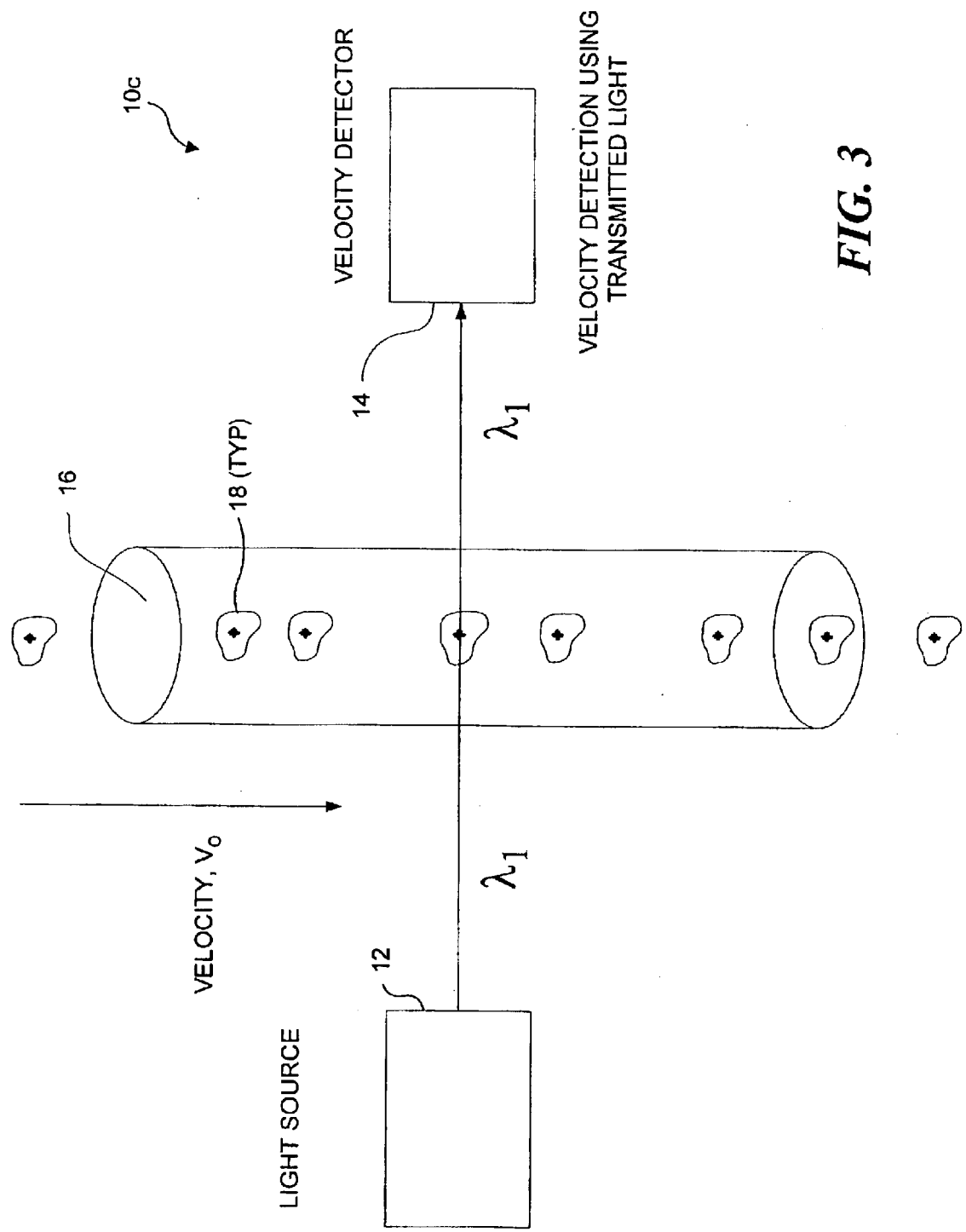
FIG. 3 is a schematic diagram of a system for measuring the velocity of objects in a flow stream by detecting the absorption of light by the objects.

The present invention can be used with any of the various illumination and light collection configurations illustrated in FIGS. 1, 2, and 3. However, those configurations should not be considered limiting on the scope of the invention, and are provided merely as exemplary configurations. Each Figure shows a light source, objects in motion (preferably objects entrained in a flow of fluid) illuminated by the light source, and a velocity detector for receiving light from the objects. The light source may be a laser, a light emitting diode, a filament lamp, or a gas discharge arc lamp, and the system may include optical conditioning elements such as lenses, apertures, and filters that are employed to deliver one or more desired wavelengths of light to the object with an intensity required for detection of the velocity (and optionally, one or more other characteristics of the object). The velocity detector includes a light sensitive detector (not separately shown in these figures) comprising, for example, a photomultiplier tube or a solid-state photodetector, and one or more other optical conditioning elements such as a lens, aperture, and/or filter, to deliver the modulated light to the light sensitive detector (also not separately shown in these figures).

FIG. 1 illustrates the configuration of a system 10a that employs light scattered by objects 18 traveling through a flow tube 16. An angle 20 (designated as angle θ) between the beam axis of an illuminator 12 and an acceptance axis of a velocity detector 14 may be adjusted so that light scattered from the objects is delivered to the velocity detector, for a particular scatter angle. The intensity profile of the scattered light is a function of the ratio of the size of the scattering elements to the wavelength of the incident light. A relatively large number of scattering elements may be present in/on the object, and angle θ may be adjusted for the detection of scattered light from elements within a desired size range for the elements.

FIG. 2 illustrates the configuration of a system 10b that uses light emitted by objects 18 traveling in flow tube 16, in response to the absorption by the objects of light from illuminator 12. In this case, the detection axis will typically be orthogonal to the illumination axis in order to minimize the amount of incident light reaching velocity detector 14. Typically, a filter or a set of filters (not separately shown) will be included in the velocity detector to deliver to the light sensitive detector only a narrow band of wavelengths of the light traveling along a detection path 22 corresponding, for example, to the wavelengths emitted by the fluorescent or phosphorescent molecules in the object, so that light in the wavelength(s) provided by the illuminator 12 is substantially eliminated.

FIG. 3 illustrates the configuration of a system 10c utilizing light from illuminator 12 that continues to propagate towards velocity detector 14 along the axis of illumination; this light is modified by objects 18 traveling in flow tube 16 by absorption, diffraction, or refraction. Note that system 10c is not well adapted for the detection of light emitted by fluorescence or phosphorescence, due to the high intensity of light emitted by illuminator 12 relative to the intensity of light emitted from objects 18, and that both types of light follow the same path to velocity detector 14. Modification of the light by the objects caused by absorption can be detected by measuring the intensity of the light incident on the velocity detector. A system of lenses may be used to restrict the origin of the collected light to a desired field in the path of the stream of objects. Modification of the light by the objects caused by diffraction or refraction may be detected through the use of a phase contrast method, in which only light subjected to phase modification by an object is visible, any unmodified light having been canceled by interference with a reference beam (not separately shown).

In each of the above-noted configurations, the light received by the velocity detector is modified by objects passing through a FOV. Because this FOV is bounded by the profile of the illumination field and by the acceptance window of the velocity detector, it would seem to be possible to estimate object velocity from the time it takes for the object to pass through the FOV. However, the FOV is bounded by gradients rather than distinct edges, and it will likely be impractical to maintain the dimensions of the FOV with a high degree of accuracy. This limitation is particularly true when the objects being illuminated or emitting the light that is detected are small in size, such as biological cells.

Figure 4:
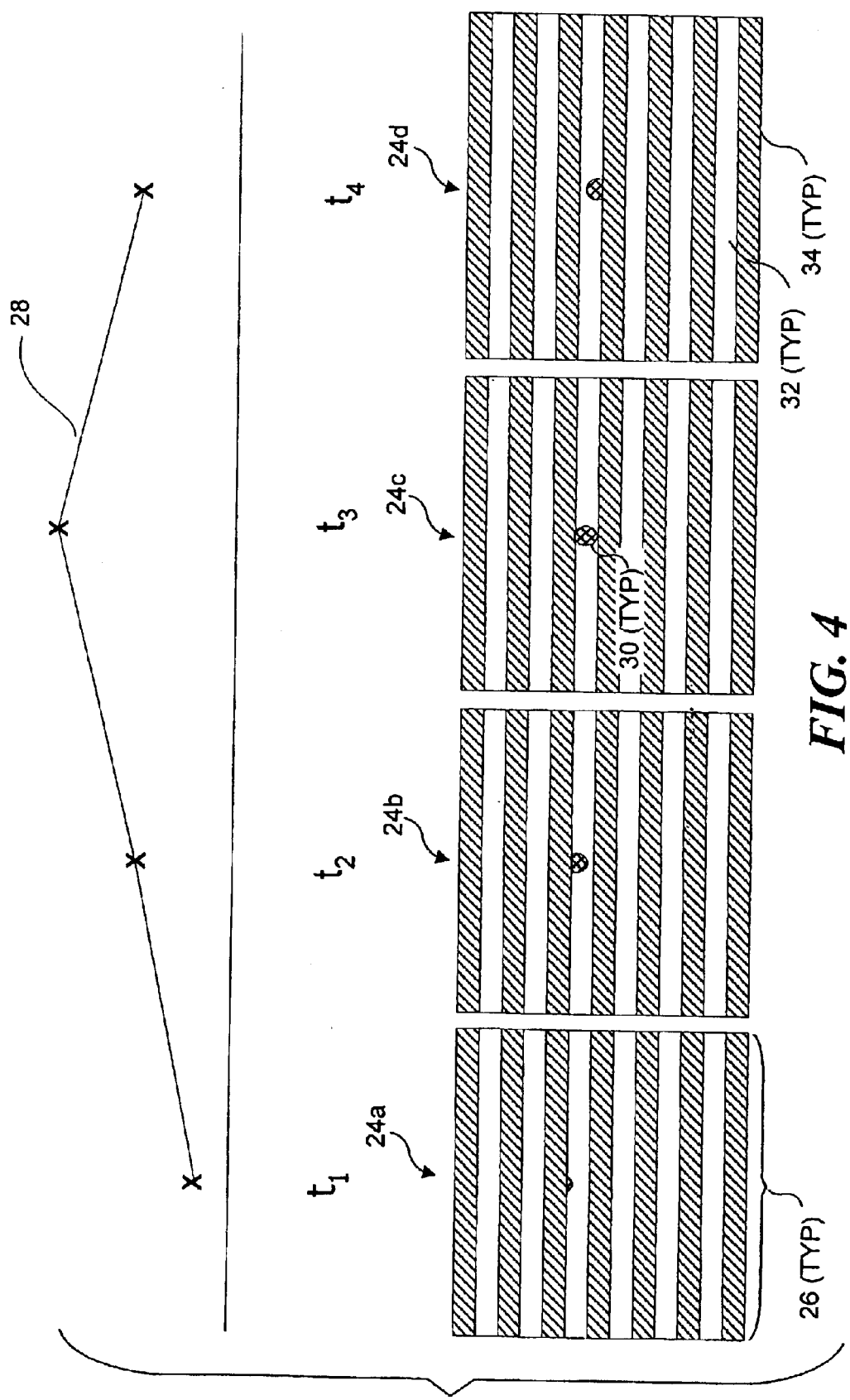
FIG. 4 is a schematic illustration of the concept of building a signal from the passage of the image of a bright object across a grating.

Placing an optical grating in the path of light incident on the velocity detector establishes a highly precise distance scale for measuring object velocity. The optical grating concept is illustrated in FIG. 4. This figure shows the positive contrast of the object relative to a background, which occurs if the light being detected is emitted from the object by fluorescence or phosphorescence, or is light that is scattered by the object. Preferably, in the optical grating shown, the opaque and transparent bar widths are substantially equal and substantially equal to an average diameter of the objects whose velocity is to be measured. This matching of the optical grating to the object size increases the light modulation amplitude, but it should be noted that the optical grating will provide the desired modulating function over a wide range of object size relative to the optical grating pitch.

FIG. 4 includes shows four snapshots 24a–24d of an optical grating 26, at equally spaced sample times, $t_1$–$t_4$, and a signal amplitude 28 incident on the light sensitive detector at those times. Note that each grating 26 includes alternating opaque zones 34 and transparent zones 32 of uniform pitch. The passage of the light emitting object 30 across one of the transparent zones 32 in the optical grating causes the amplitude to increase as the exposed area of the object increases, and then to decrease as the object moves behind one of the opaque zones 34. In the ideal case, only direct light from objects would reach the detector. Typically, however, some scattered light or light from stray fluorescence will continuously pass through the transparent zones, creating a constant bias or offset in the light sensitive detector output signal.

Figure 5:
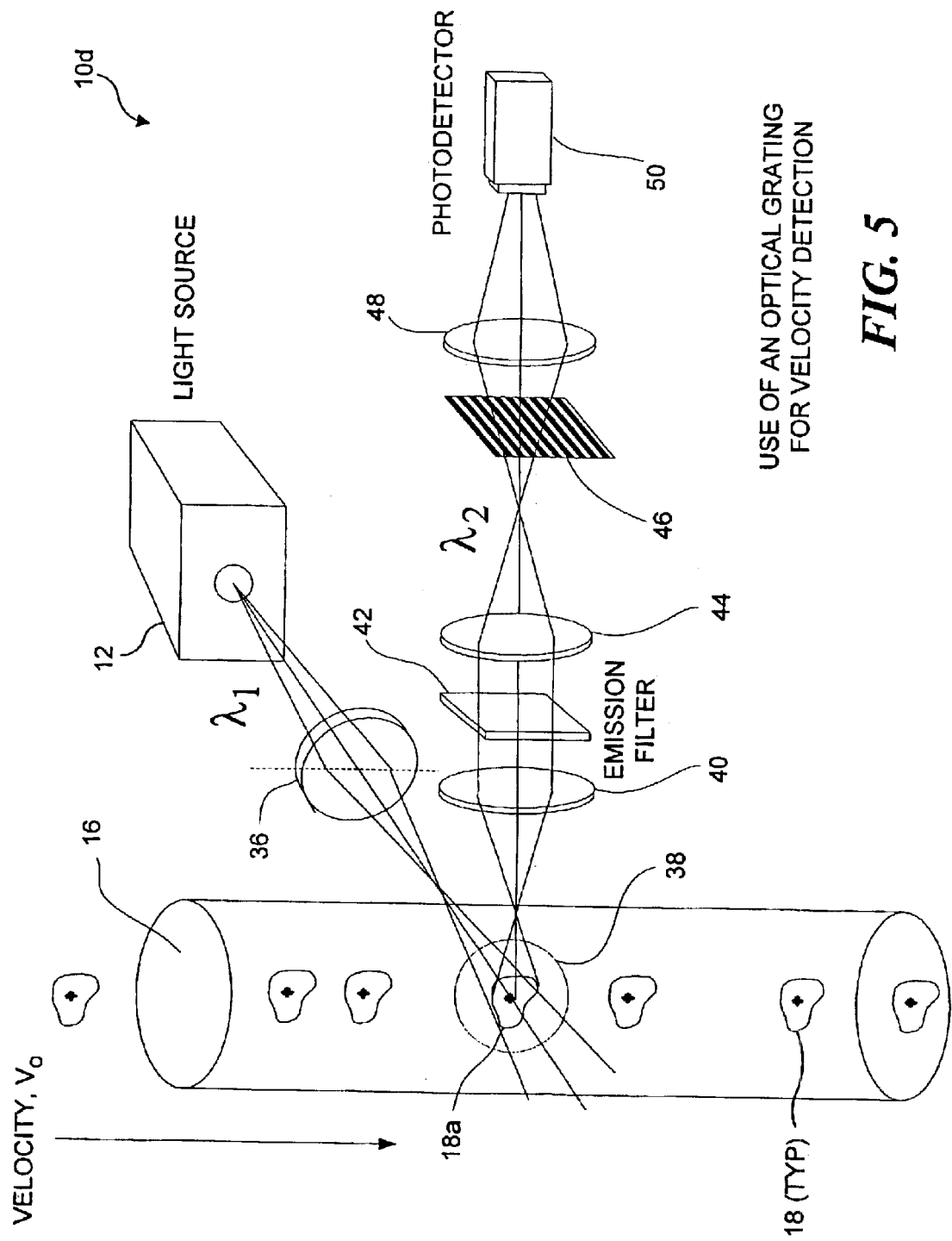
FIG. 5 is a schematic diagram showing the integration of an optical grating into a flow velocity measurement system.

FIG. 5 shows an optical system 10d that illustrates how the optical grating-based detection system might be implemented for the case in which the objects emit photons through the process of fluorescence. A lens 36 creates a focused illumination field at a wavelength $\lambda_1$ in a FOV 38. Fluorescence in an object 18a caused by this illumination results in photons being emitted by the object omnidirectionally at a longer wavelength, $\lambda_2$. Some of these emitted photons are collected by lens 40 on the detector axis. An emission filter 42 is used to reject light at wavelengths other than $\lambda_2$. Lens 40 and a lens 44 create a focused image of the object on an optical grating 46. It would be possible to generate a conjugate image of the object and the optical grating at a camera, in which case the camera would produce well-focused images of objects passing across the sharp boundaries of the optical grating, as shown in FIG. 4. However, accurate periodic sampling of the modulated light produced as light from the moving object passes through the optical grating is sufficient for making the velocity measurement, and the extra complications of capturing and analyzing images is eliminated. In the preferred approach, a lens 48 is used to collect the light transmitted by the optical grating and deliver it to a photodetector 50. It should be noted that other optical elements, such as concave mirrors, can be used in place of the lenses discussed above.

In a preferred application, objects 18 are preferably biological cells entrained in a fluid. The fluid is confined to a narrow column passing through FOV 38 of the optical system by hydrodynamic focusing with a flow sheath. The cells are kept within the depth of field of lenses 40 and 44, assuring good focusing and, therefore, a modulation amplitude sufficient for the determination of the velocity of the object.

Light from a single object moving through the FOV at a uniform velocity will, when modulated by the optical grating, have a frequency directly proportional to the velocity, as defined by the following relation:

$$f = \frac{v}{s}$$

where:
 f=frequency (Hz)
 s=grating pitch (microns)
 v=velocity (microns/sec).

The amplitude of the signal generated at the photodetector by light from a single object will follow the contour of the illumination field. If the illumination field profile has a Gaussian shape, for example, the signal is described by the equation:

$$x(t) = A_O e^{-(t-t_{pk})^2/\tau^2} e^{j2\pi f(t-t_0)} + A_L$$

where:
 $A_O$=peak amplitude
 $A_L$=leakage amplitude from stray light
 $t_{pk}$=time of arrival at peak of illumination field
 $\tau$=envelope decay constant
 $t_0$=time of arrival at edge of grating image.

Figure 6:
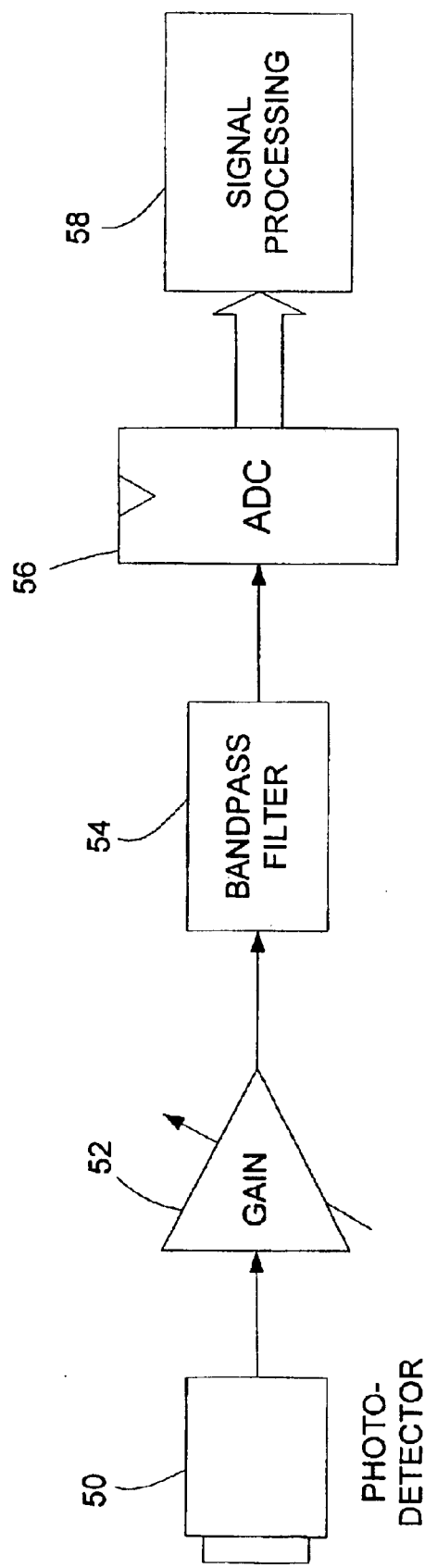
FIG. 6 is a block diagram illustrating the stages of processing the signal from a light sensitive detector for the purpose of object velocity measurement.
Figure 7A:
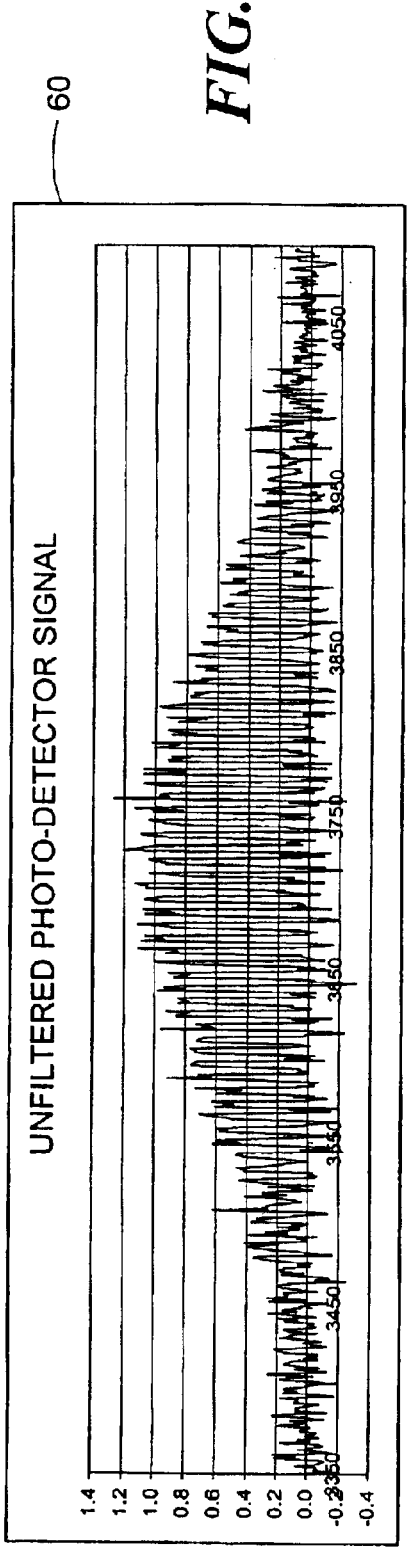
FIG. 7A illustrates a graph of a typical photodetector signal before bandpass filtering.
Figure 7B:
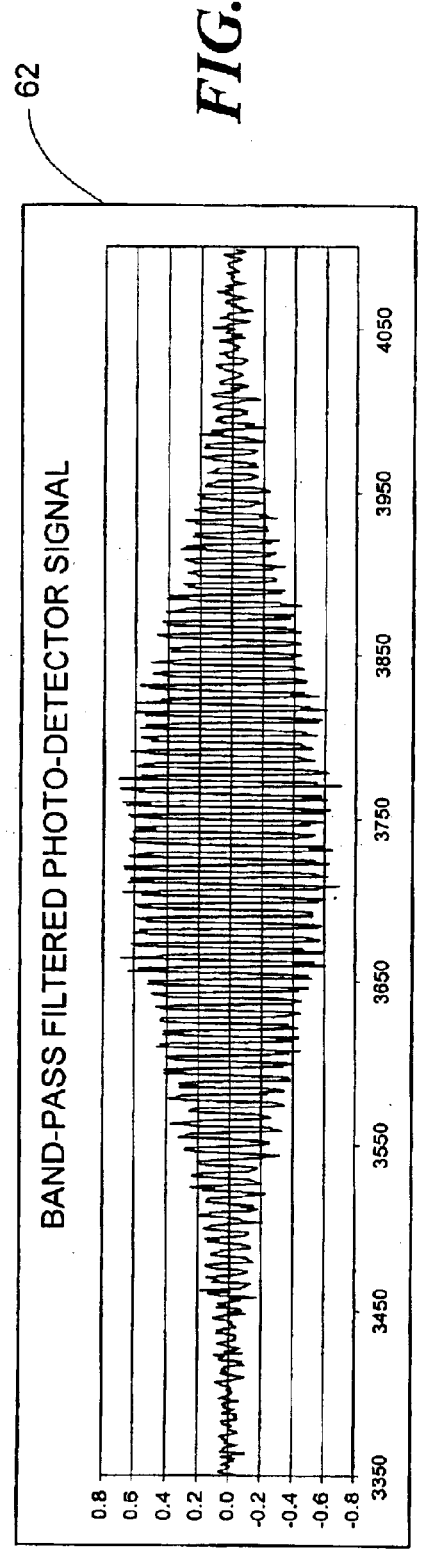
FIG. 7B illustrates a graph of a typical photodetector after bandpass filtering.

FIG. 6 shows a typical embodiment of a photodetector signal conditioning and capture system. A central feature of this system is the use of a bandpass filter 54 to filter the signal from the photodetector 50 (after the signal is amplified). The purpose of this bandpass filter is to reject a direct current (DC) component, $A_L$, and to eliminate any frequencies above a Nyquist limit, $f_{samp}/2$, of an analog-to-digital converter (ADC) 56, where $f_{samp}$ is the highest light modulation frequency of interest. A variable-gain amplifier 52 is used to adjust the amplitude of the signal to match the dynamic range of ADC 56. The digitized signal is delivered to a digital signal processor 58 for analysis. Digital signal processor 58 can comprise a programmed computing device (e.g., a microprocessor and memory in which machine instructions are stored that cause the microprocessor to appropriately process the signal), or an application specific integrated circuit (ASIC) chip that carries out the processing, or a digital oscilloscope that includes such signal processing capability. FIG. 7A shows an exemplary unfiltered photodetector signal 60 generated by light from a single object passing through the optical grating field, while FIG. 7B shows an exemplary filtered photodetector signal 62, after application of bandpass filter 54 (see FIG. 6) to the signal.

As noted above, the present invention includes four distinct preferred embodiments. Those four preferred embodiments employ three different techniques for analyzing the signal from the photodetector, to deliver accurate velocity estimates for the objects. The different signal processing methods are described in detail below.

As noted above, one preferred use of the velocity measurement in the present invention is to provide timing signals to optical systems that determine characteristics of small moving objects, such as a flow cytometer. In non-imaging photomultiplier tube (PMT) instruments commonly known as flow cytometers, estimates of flow velocity are used for correcting measurements that depend on signal integration time and to accurately delay the sorting of a cell after its analysis. The optical grating-based velocity detection methods can be used to improve the accuracy and reliability of such flow cytometric measurements and the purity of sorted cell samples by providing a more accurate flow velocity estimate.

The flow imaging systems disclosed in commonly assigned U.S. Pat. No. 6,249,341, issued on Jun. 19, 2001, and entitled IMAGING AND ANALYZING PARAMETERS OF SMALL MOVING OBJECTS SUCH AS CELLS, as well as in commonly assigned U.S. Pat. No. 6,211,955, issued on Apr. 3, 2001, also entitled IMAGING AND ANALYZING PARAMETERS OF SMALL MOVING OBJECTS SUCH AS CELLS, demand very accurate measurements of flow velocity for clocking the TDI detector. The transfer of charge from one row to the next in the TDI detector must be synchronized with the passage of objects through the flow cell. Note that the specification and drawings of each of these two patents have been specifically incorporated herein by reference.

Figure 8:
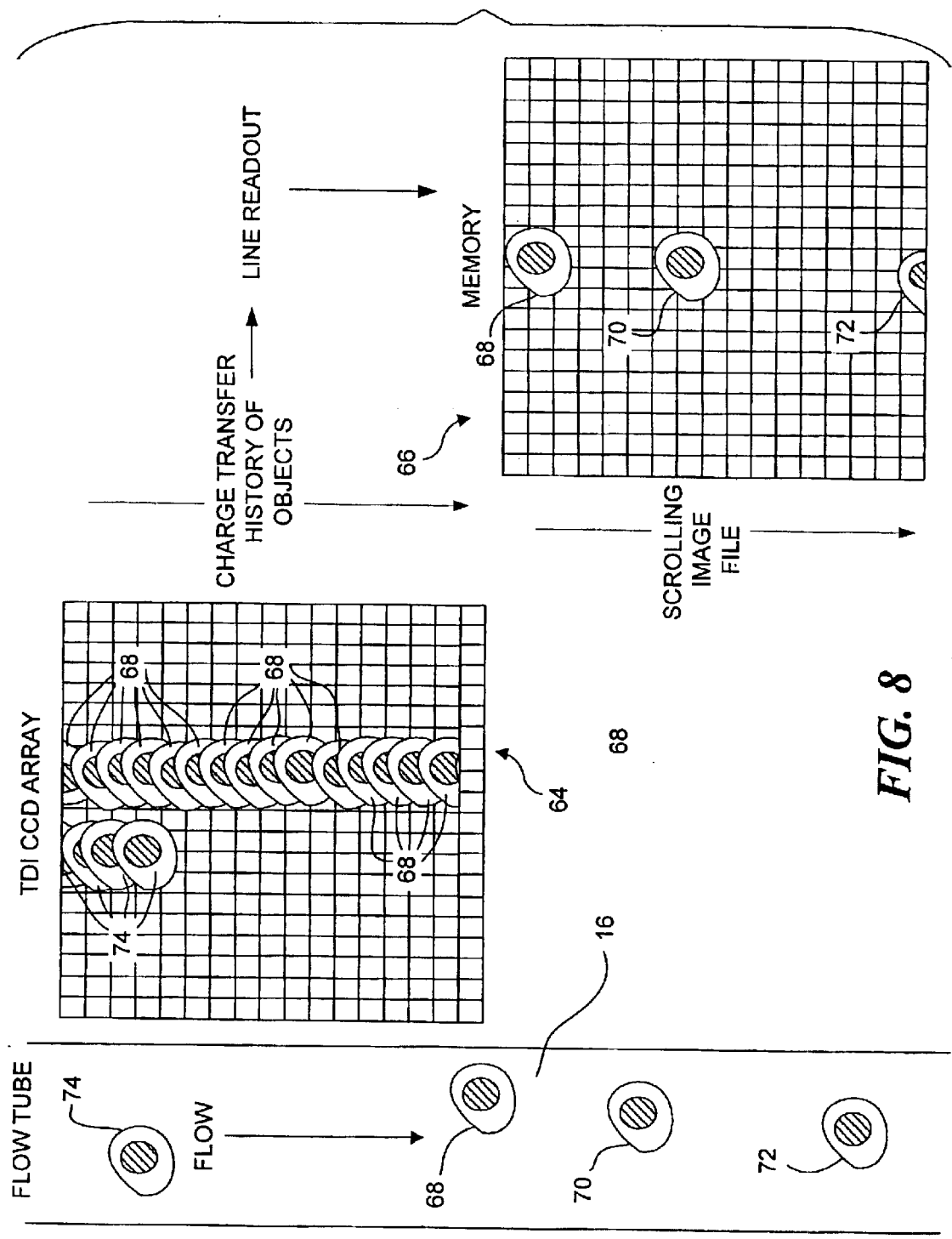
FIG. 8 is a schematic representation illustrating the operation of a TDI detector.

The theory of operation of a TDI detector, such as those employed in the above-noted patent references is shown in FIG. 8. As objects travel through flow tube 16 and pass through the volume imaged by the TDI detector, their images travel across the face of the TDI detector. The TDI detector comprises a charge coupled device (CCD) array 64, which is specially designed to allow charge to be transferred on each clock cycle in a row-by-row format, so that a given line of charge remains locked to or synchronized with a line in the image. The row of charge is clocked out of the array into a memory 66 when it reaches the bottom of the array. The intensity of each line of the signal produced by the TDI detector corresponding to an image of an object is integrated over time as the image and corresponding signal propagate over the CCD array. This technique greatly improves the SNR of the TDI detector compared to non-integrating type detectors—a feature of great value when responding to images from low-level fluorescence emission of an object, for example.

The operation of the TDI detector can be understood from FIG. 8 by observing the traversal of object 68 across the region imaged by CCD array 64 and the history of the charge produced in response to the image of object 68 by CCD array 64. The charge is transferred from row to row in the array as the image of the object travels down the array. When a row of charge reaches the bottom of the array, it is transferred into scrolling memory 66, where it can be displayed or analyzed. In FIG. 8, objects 70 and 72 traverse flow tube 16 ahead of object 68, while an object 74 traverses flow tube 16 after object 68. Proper operation of the TDI detector requires that the charge signal be clocked down the CCD array in synchronization with the rate at which the image of the object moves across the CCD array. An accurate clock signal to facilitate this synchronization can be provided if the velocity of the object is known, and the present invention provides an accurate estimate of the objects velocity, and thus, the velocity of the image over the CCD array of the TDI detector.

Figure 9:
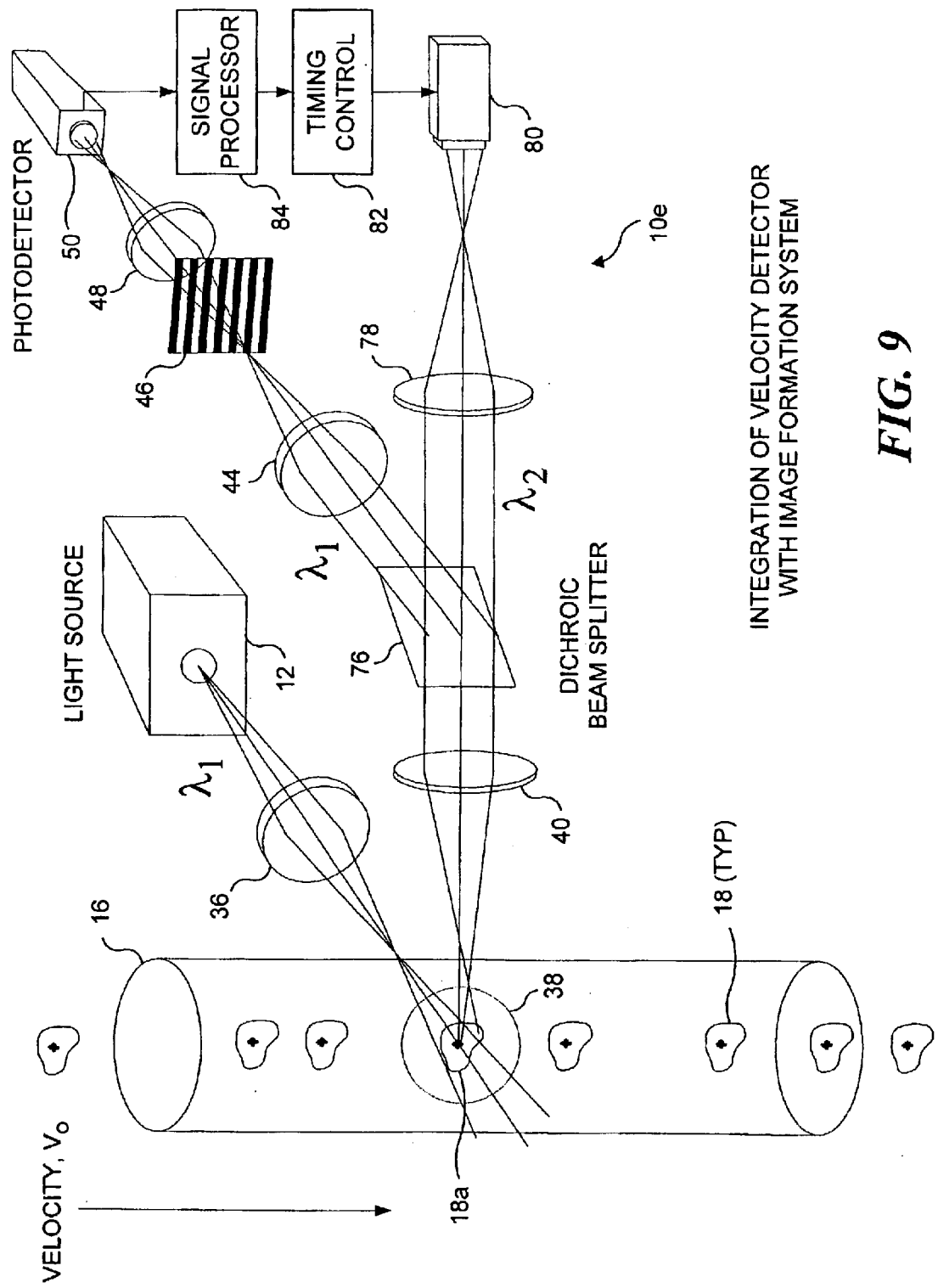
FIG. 9 is a schematic diagram of a flow imaging system including a flow velocity measurement system delivering timing to the TDI detector.

FIG. 9 shows the integration of the velocity detector into a TDI-based object imaging system 10e. The signal from photodetector 50 is processed by a signal processor 84, and may optionally carry out functions such as amplification and filtering. Additional details of the signal processing are provided below. Preferably, signal processor 84 comprises a programmable computing device, but an ASIC chip or digital oscilloscopes can also be used for this purpose. The frequency of the photodetector signal is measured and the velocity of object 18a is computed as a function of that frequency. The velocity is periodically delivered to a TDI detector timing control 82 to adjust the clock rate of a TDI detector 80. The TDI detector clock rate must match the velocity of the image of the object over the TDI detector to within a small tolerance to minimize longitudinal image smearing in the output signal of the TDI detector. The velocity update rate must occur frequently enough to keep the clock frequency within the tolerance band as flow (object) velocity varies. Note that a dichroic beam splitter 76 has been employed to divert a portion of light from object 18a to photodetector 50, and a portion of light from object 18a to TDI detector 80. An imaging lens 78 focuses an image of object 18a onto TDI detector 80.

Figure 10:
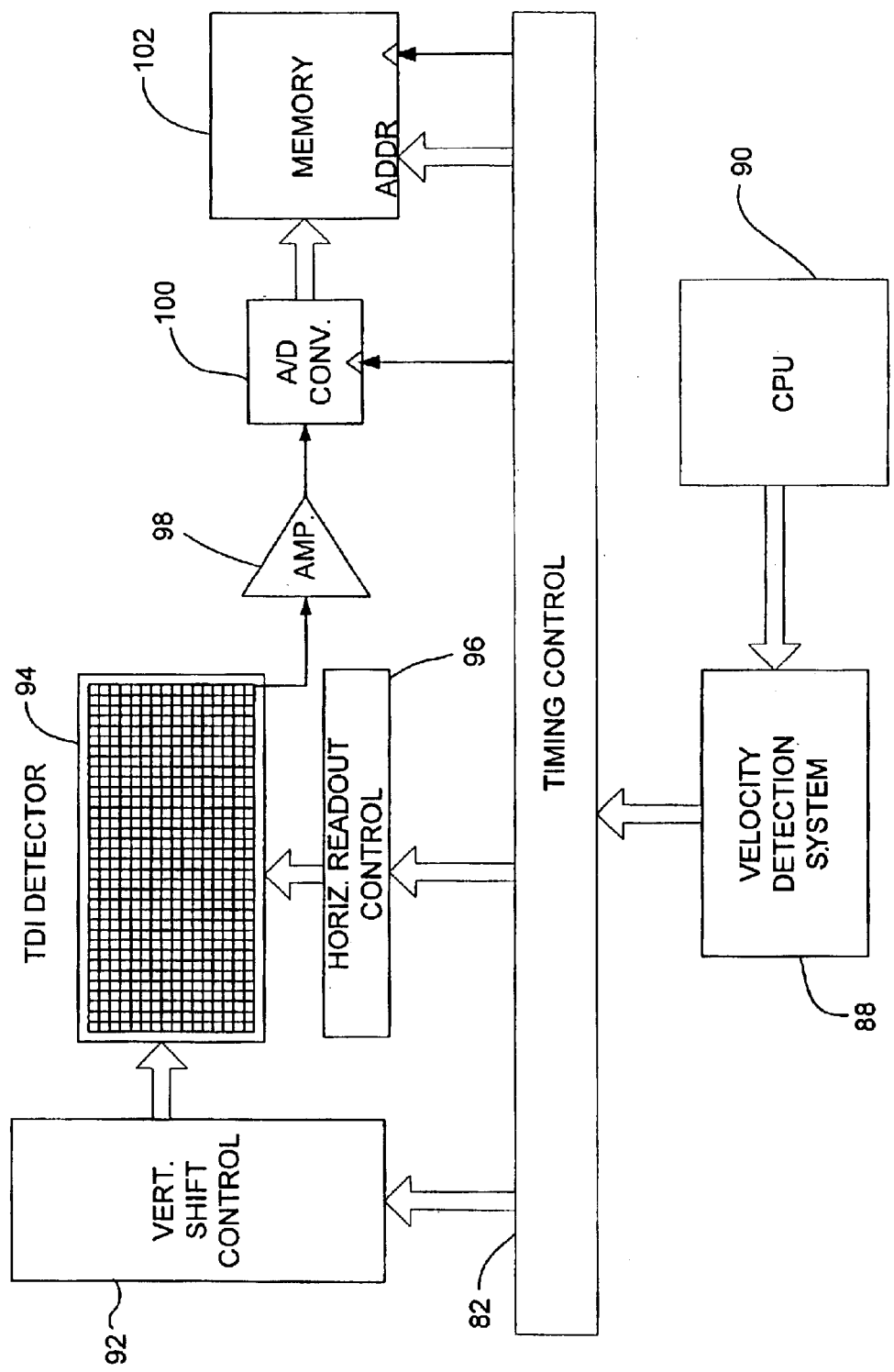
FIG. 10 is a block diagram of the structure of a TDI detector and the associated subsystems of the flow imaging system.

FIG. 10 shows how a velocity detection system 88 is preferably employed by TDI detector timing control 82 (shown in FIG. 9). Note that velocity detection system 88 can be configured as shown in FIG. 9, or provided in other configurations (such as shown in FIG. 5). Velocity detection system 88 provides a clocking signal indicative of the velocity of a flow or of objects in a flow for synchronizing the movement of images of the objects over a TDI detector with the movement of charge responsive to the images. The TDI detector is preferably included in a flow cytometry system, although other applications of the present invention are contemplated. Preferably, the velocity detection system is controlled by a CPU 90, which executes a velocity detection supervisor program defined by machine instructions that are stored in memory (not separately shown). Note that CPU 90 can also be employed to carry out the signal processing function of velocity detection system 88. The clocking of the charge through a TDI detector 94 is accomplished by a vertical shift controller 92 and a horizontal readout controller 96, both of which are driven by a TDI detector timing control system 82. The velocity detection system 88 passes a clock frequency command to TDI detector timing control system 86 to set a rate at which rows of charge are shifted down the TDI detector array. Detector timing control system 86 synchronizes horizontal readout controller 96 with vertical shift controller 92.

The image information leaves TDI detector 94 as an analog signal, which is then amplified with an amplifier 98 and digitized by an ADC 100. The ADC output is stored in a memory 102 under the control of timing control system 86, where it can be accessed for display and analysis.

Figure 11:
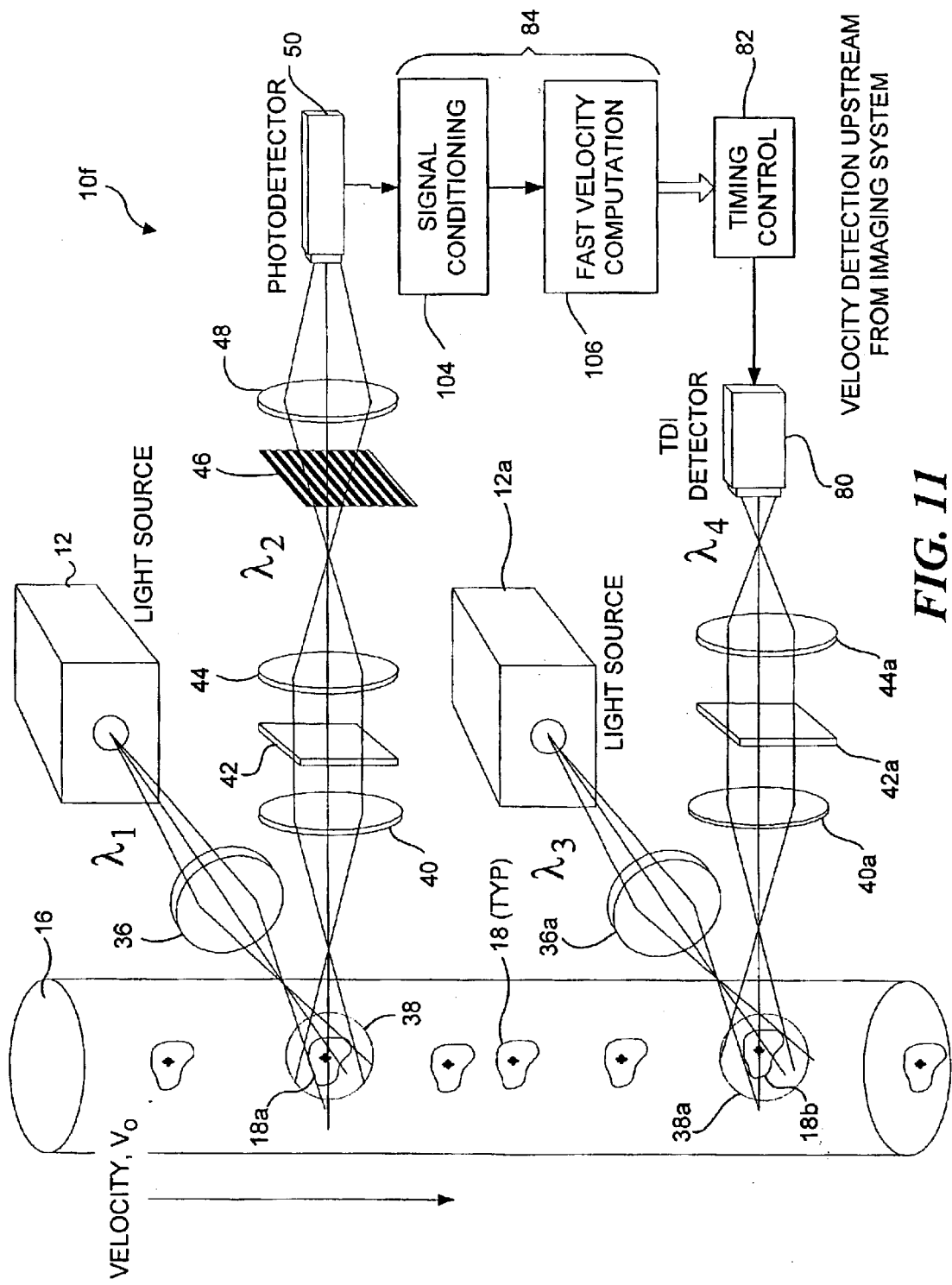
FIG. 11 is a schematic diagram of a flow imaging system in which object velocity measurement is performed upstream from image acquisition.

Another embodiment of a TDI-based flow imaging system 10e is shown in FIG. 11. This embodiment is intended to address the problem of synchronizing the TDI detector to individual objects traveling at different velocities, as may be the case in systems with poor hydrodynamic focusing. In TDI-based flow imaging system 10f, the velocity measurement is performed upstream of the point where image capture occurs. Velocity measurements are updated sufficiently rapidly to be passed forward to the TDI detector timing controller in time for the TDI detector clock (not separately shown) to be set to match the velocity of an image of a particular object moving across the TDI detector. The configuration of flow imaging system 10f is similar to that shown in FIG. 5, except that FOV 38 for velocity detection is separate from a FOV 38a used for TDI image acquisition. Imaging system 10f uses a separate light source 12a, separate lenses 36a, 40a, 44a and a separate filter 42a disposed in the collection path for light from the objects that is directed to TDI detector 80. The photodetector signal is processed using a signal conditioning component 104 and a FFT based fast velocity calculator 105 that is sufficiently fast to deliver new velocity estimates for objects to timing controller 82 in less time than required for the objects to travel from velocity measuring FOV 38 to imaging FOV 38a. Note that in imaging system 10f, signal processing block 84 of FIG. 10 is separated into signal conditioning component 104 and fast velocity calculator 106.

Accurate cell velocity measurements can also be employed to increase sort purity in droplet-based flow sorters. Such systems are typically PMT-based flow cytometers equipped to sort cells by their light scattering characteristics or fluorescence emission. In such systems, the characterization of a cell is performed just as the liquid carrying the cell leaves the droplet-forming nozzle. Based on an optical measurement, the unbroken part of the stream is either charged or not charged before the droplet containing the cell breaks free from the stream. An electrostatic field is used to deflect the charged droplets into a container separate from the container catching the uncharged droplets.

Figure 12:
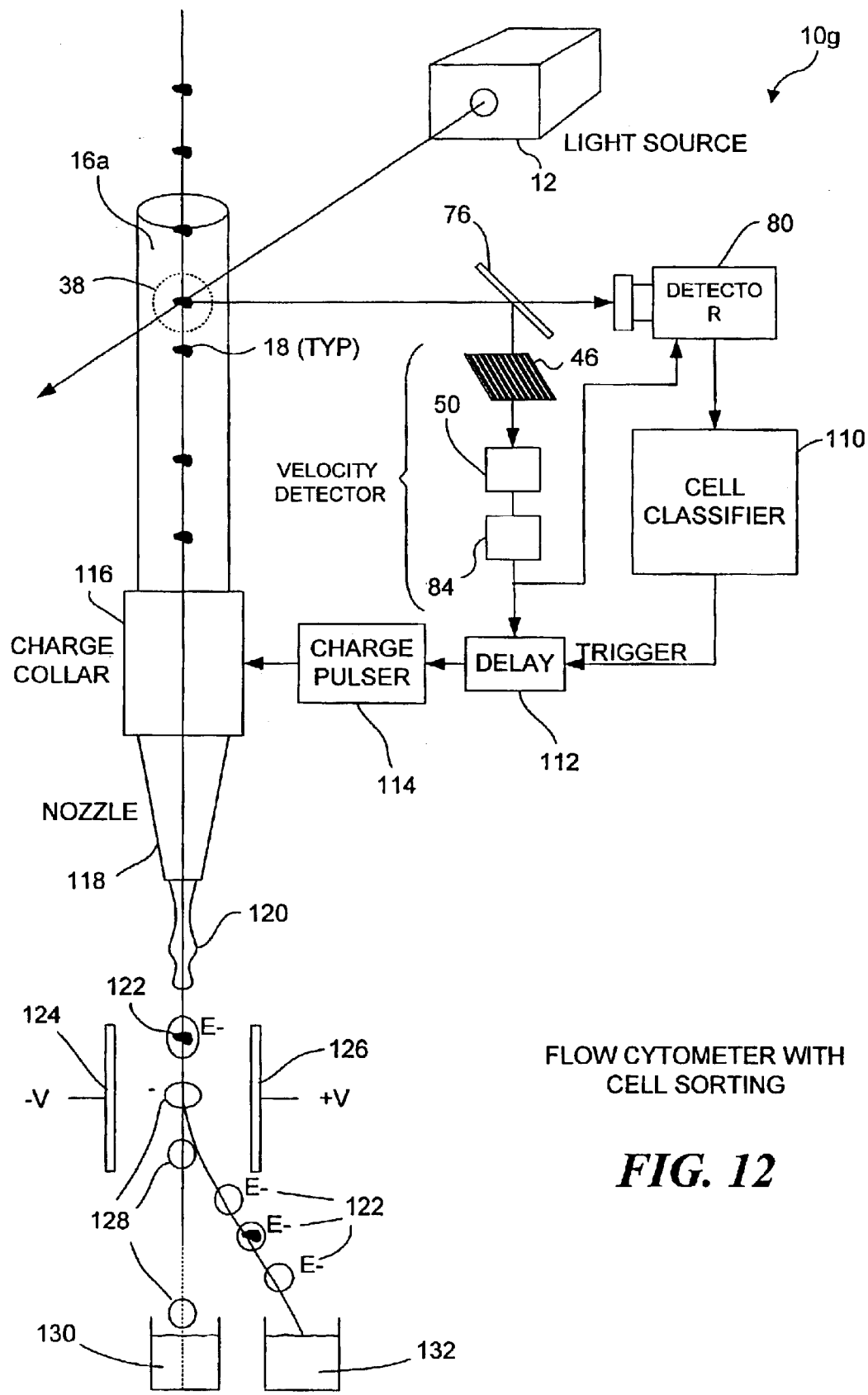
FIG. 12 is a schematic diagram of a cell sorting apparatus including the elements of a velocity measurement system controlling a droplet charging system.

FIG. 12 illustrates an instrument in which the optical grating-based velocity detection system of the present invention is used both to synchronize a TDI detector for capturing images and for timing the droplet charging system. In system 10g, both velocity detection and image capture are accomplished in common FOV 38. Images from TDI detector 80 are delivered to a high-speed cell classifier 110. The classifier searches the images for objects of interest. Once such an object has been found, the classifier automatically decides on the basis of the characteristics of that object whether the object should be sorted into a container 130 or a container 132. If the decision is made to place an object into container 132, the classifier triggers the charging system, which comprises a time delay operator 112, a charge pulser 114, and a charge collar 116. The time delay used by time delay operator 112 is set to match a transit time of an object from FOV 38 to an attached droplet 120, according to the velocity measurement performed in signal processing block 84 of the velocity detector. Note that as described above, the velocity detector includes optical grating 46, photodetector 50, and signal processing block 84. Charged droplets 122 are deflected into container 132 by the static electric field between electrodes 124 and 126. The distance between the optical sensing region and the charge collar is made long enough to provide sufficient time for image-based object classification to reach completion. In this way, a larger and more complex set of features can be used in the sorting decision than would be the case in conventional cell-sorting flow cytometers.

FDVM of Velocity of Objects on a Support

The first and second embodiments are directed to FDVM methods that convert light from cells or other objects into an amplitude modulated (AM) signal with a characteristic frequency that is proportional to velocity. Any number of cells traveling at the same velocity, e.g., in a fluid flow, can be in the sensitive region simultaneously, and the modulated light produced in response to the motion of each will have the same fundamental frequency, differing only in phase. Unlike the prior art time-domain methodology, the FDVM method requires no synchronization and is highly tolerant of variability in the fine structure of the time-based waveform generated by the cells.

In the FDVM method, moving luminescent or illuminated cells are imaged onto a ruling of transparent and opaque bars to generate an amplitude modulated light signal. The optical magnification and ruling pitch are chosen such that the bars are approximately the size (e.g., diameter) of the cell. The pitch of the ruling used in the optical grating is uniform. Therefore, the light collected from cells is alternately blocked and transmitted through the ruling as the cell traverses the sensitive region. The modulated light is directed toward a detector, producing an analog output signal with a fundamental frequency proportional to the cell velocity. The analog signal is converted to digital samples. An FFT algorithm decomposes the resulting digital signal into spectral peaks in the frequency domain, which are processed to determine the velocity. A first FDVM embodiment is directed to a method in which objects are deposited upon a support, and the support is moved through the FOV. A second FDVM embodiment is directed to a method in which objects are entrained in a fluid that is caused to flow through the FOV.

Figure 13:
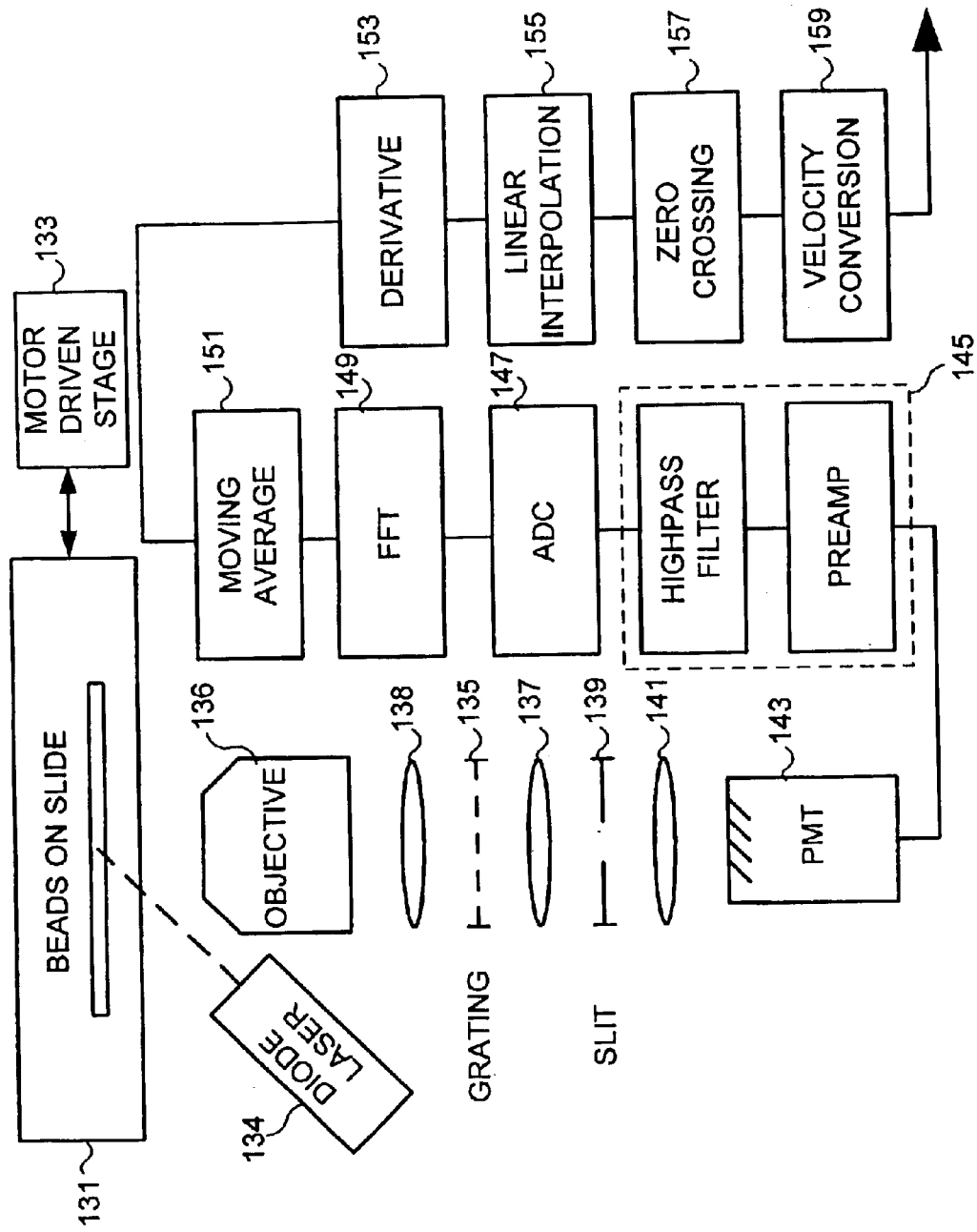
FIG. 13 is a block diagram illustrating a first embodiment of a frequency domain velocity measurement system in which objects are moved through a FOV on a support.

A block diagram of the first FDVM embodiment of a velocity detection system is shown in FIG. 13. Beads are deposited on a slide 131 that is driven through the FOV. For an initial feasibility study, the objects employed comprised 7.9 μm diameter beads (purchased from Bangs Corporation) fixed to a moving microscope slide. Movement of the slide through the FOV was produced by mounting the slide on a closed-loop DC servo stage 133 (available from Newport Corporation), and the sample speed was monitored using a one micron resolution linear encoder included in the stage. The stage had a maximum velocity of 100 mm/s, controlled using a proportional-integral-derivative (PID) control system (available from National Instruments Corporation). The linear encoder independently monitored the movement of the slide (and hence, the movement of the beads on the slide) to provide comparative data available to confirm the accuracy and precision of the FDVM velocity detection system. While it is expected that determining the velocity of objects entrained in a fluid will have widespread application, it is also anticipated that the moving support (slide) embodiment will also be useful, particularly for objects that cannot be easily or stably entrained or suspended in a fluid.

The sample beads were illuminated with light from a diode laser 134 (from Thor Labs, Inc.) so that light striking the beads was scattered into the optical collection system. The moving sample image was projected at approximately 5× magnification by an objective 136 and a lens 138, onto an optical grating 135 having a ruling of 50 micron bars (available from Gage Technologies), oriented at right angles to the motion of the sample. The ruling and sample were then imaged together on an adjustable slit 139 by an imaging lens 137, disposed to simulate the field of view of a flow-based instrument. The light passing through the slit was then collected by a lens 141 and directed onto a PMT 148 (Hamamatsu Corp., Model 5783-01) such that the aperture of the optical system was imaged onto the PMT (143). In this manner, there was no movement of the signal across the PMT as the bead images traversed the ruling.

The signal processing portion of this embodiment of a velocity detection system is also depicted in FIG. 13. The signal from the PMT was amplified and high-pass filtered through an amplifier/filter 150 (Stanford Research, Model SR570). The filtered signal was then digitized using an analog-to-digital converter 147, and the digitized signal was processed using an FFT processor 149 to produce a frequency spectrum with a well-defined peak at the frequency corresponding to the velocity of beads. The FFT spectrum was smoothed using a moving average filter 151 and the zero crossing of the derivative of the smoothed FFT spectrum was determined in processing blocks 153, 155, and 157. All signal processing was performed on a digital storage oscilloscope (from LeCroy Corp.). The velocity of the objects on the slide was then calculated by taking the product of frequency defined by the zero crossing, the ruling spacing, and the inverse of the magnification in a velocity conversion block 159. The precision of the measurement was enhanced by linearly interpolating between the derivative data points to better define the zero crossing frequency.

Figure 14A:
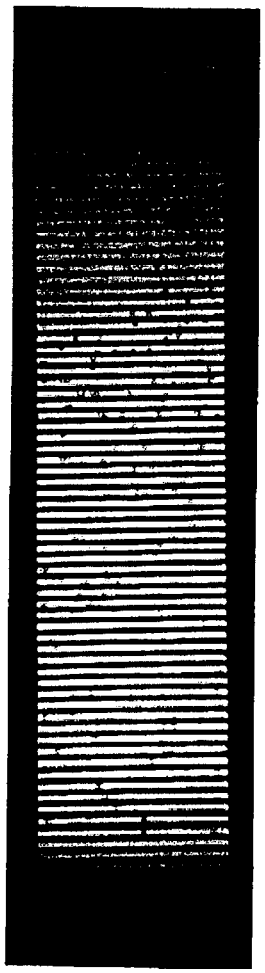
FIG. 14A is an image of beads, ruling, and an adjustable slit acquired by inserting a beam splitter, lens, and detector after the ruling, placing a light source behind the slide, and opening the slit for clarity.
Figure 14B:
FIG. 14B is a scattered light image with the slit of FIG. 2A closed down to 200 microns (40 microns in object space) and with the beads moving across the field of view at 20 mm/s, while data was acquired for approximately one second.

FIG. 14A shows an image of the beads, ruling, and adjustable slit. The image was acquired by inserting a beam splitter, lens and detector after the ruling, placing a light source behind the slide, and opening the slit for clarity. The beads were magnified 4.92× before being imaged on the ruling, which had a line width of 50.8 $\mu$m (9.842 lp/mm). FIG. 14B is a scattered light image in which dark field illumination was employed, and the slit closed down to 200 microns (40 microns in object space), as it was during data acquisition. In operation, the motorized stage moved the beads across the field of view at 20 mm/s (left to right in the illustrated example), while data was acquired for approximately one second.

Figure 15:
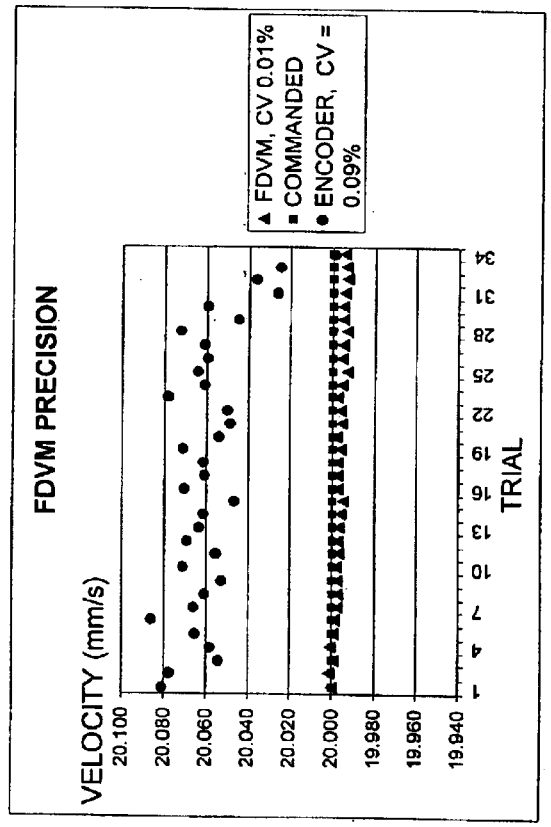
FIG. 15 is a graph illustrating experimental results for a closed-loop DC servo driven stage that drives 7.9 microns beads affixed to a microscope slide at 20 mm/s.
Figure 16:
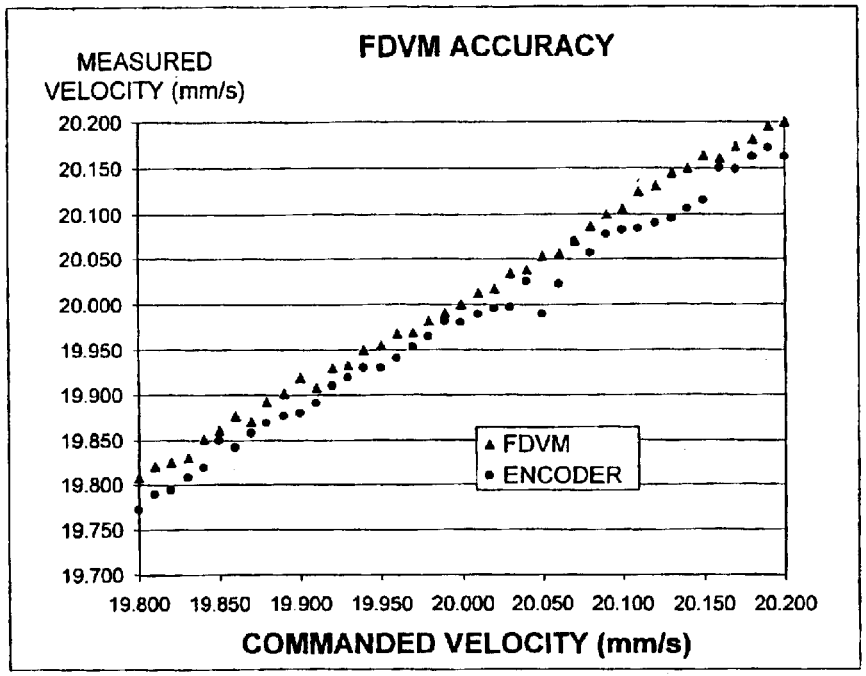
FIG. 16 is a graph of showing experimental results comparing commanded velocity to measured velocity, for the FDVM and encoder.
Figure 17:
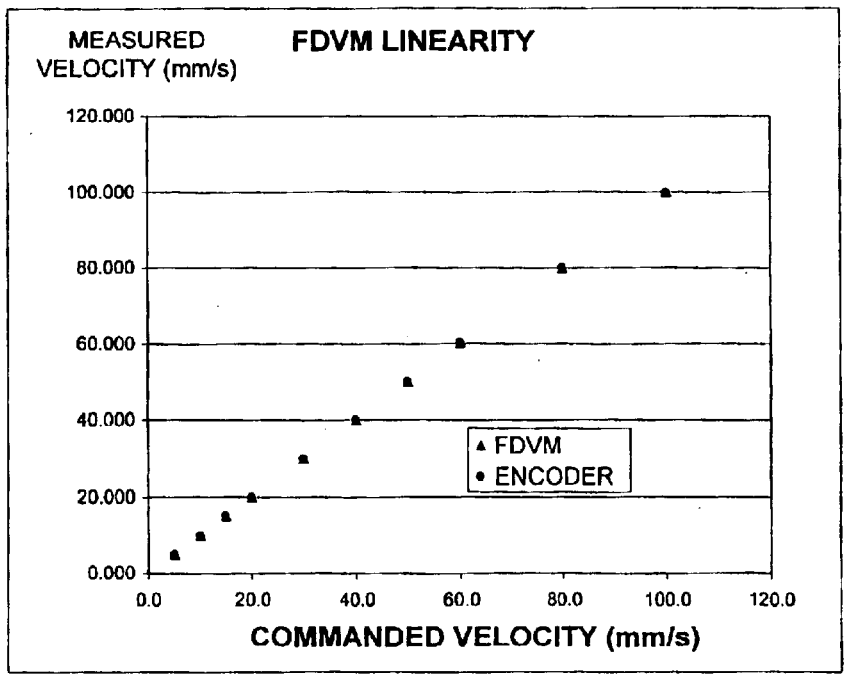
FIG. 17 is a graph of experimental results showing the linearity of the commanded velocity and measured velocity, for the FDVM and encoder.

Using the methods and apparatus discussed above, data were taken in three experiments to determine the precision and accuracy of the this technique. FIGS. 15, 16, and 17 summarize the results of these experiments. In the results of the precision experiment shown in FIG. 15, the stage was commanded to move at 20 mm/s in 34 separate runs. The velocities measured by the encoder on the stage and by the FDVM method of the present invention were both recorded and plotted. To calibrate the FDVM method, a correction constant was determined by taking the quotient of the first commanded velocity and the frequency peak produced by the FDVM method. Each subsequent measurement was multiplied by this value. The precision of the FDVM method was determined by calculating a coefficient of variation (CV) for 34 separate runs. By this measure, the precision of the encoder method is 0.09% and the precision of the FDVM method of the present invention is 0.01%, as shown in FIG. 16. This experiment demonstrates that the precision of the FDVM method exceeds targeted performance requirements by a factor of fifty.

It should be noted that the poorer apparent performance of the encoder method is likely the result of the servo feedback system's internal velocity calculation. Rather than making one velocity measurement per run using all 20,000 counts, the servo system makes a velocity measurement every 60 counts for the purposes of real-time motion control. The stage feedback system supplied a function to average the individual velocity measurements within a run. Each point in the encoder precision plot is therefore the average of 333 individual velocity measurements.

The results of the linearity experiment are shown in FIG. 17. The stage was commanded to move over a velocity range from 5 mm/s to 100 mm/s as specified in the performance requirements. Velocity measurements were taken using the FDVM method and the stage encoder. Over this range both measurements produced highly correlated $R^2$ values of unity with slopes of 1.0002 and 1.0007 for the FDVM method and stage encoder, respectively. These results demonstrate that the FDVM method of the present invention has good linearity over a range of velocity measurements exceeding an order of magnitude.

Figure 18:
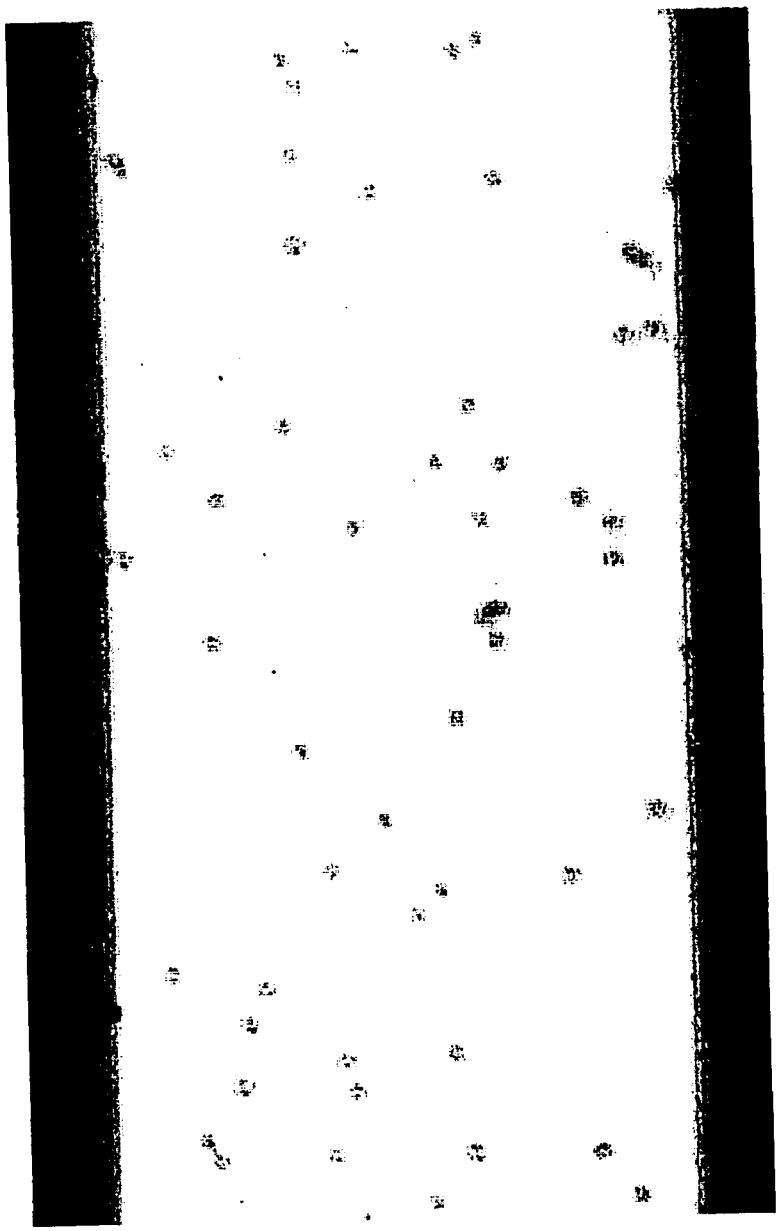
FIG. 18 is a TDI image captured using frequency-domain velocity feedback.

FIG. 18 is an image captured using a TDI detector configured to view the sample slide, as in FIG. 2. The TDI detector or detector captures unblurred imaged of objects, which move at the same rate as the charge that is clocked across the chip during imaging. Because the TDI detector is located behind the stationary ruling, the ruling has blurred across the entire field of view. The ruling is responsible for some image degradation as each bead image traverses the entire ruling during the imaging process. The TDI detector's pixel clock was generated using the velocity determined by the FDVM method of the present invention. Although a comprehensive analysis of the image has not been performed, it is apparent that the velocity accuracy is sufficient to prevent image elongation in the horizontal axis of motion of the TDI detector.

The goals of the feasibility study employing beads on a slide were to develop a velocity detection system with high precision, high accuracy, good linearity and tolerance of wide variations in sample density. These goals were exceeded and the system was successfully used to capture images using a TDI detector. The 0.5% feasibility requirements were set to ensure less than one pixel blur when using the velocity detection system in concert with a 100 stage TDI detector. In fact, the feasibility system demonstrated precision, accuracy, and linearity better than 0.05% and therefore can be used with a 1000 stage TDI detector. In the context of the cell analysis system being developed in which the present invention will be included, more stages enable the image to be collected over a larger field of view, thereby increasing the integration time and the sensitivity of the instrument. Conversely, if the field of view is held constant, the pixel size can be reduced, increasing the spatial resolution of the instrument. Accurate velocity detection is also beneficial for cell sorting, where knowledge of the stream velocity can be used to actively adjust drop delays to compensate for drift over the course of an experiment.

Supervisory Control of Velocity Measurement Systems

In all embodiments, the present invention entails the steps of (1) formation of images of the objects of interest focused in the plane of the optical grating, (2) delivery of the modulated light transmitted by the optical grating to the surface of a photosensitive detector, (3) conversion of the modulated light signal to an electronic signal, (4) signal acquisition and processing, and (5) velocity determination.

Preferably, one or more of these operations will be brought under the control of supervisory software by interfacing the velocity measurement system with a general purpose computer or other computing device.

Figure 19:
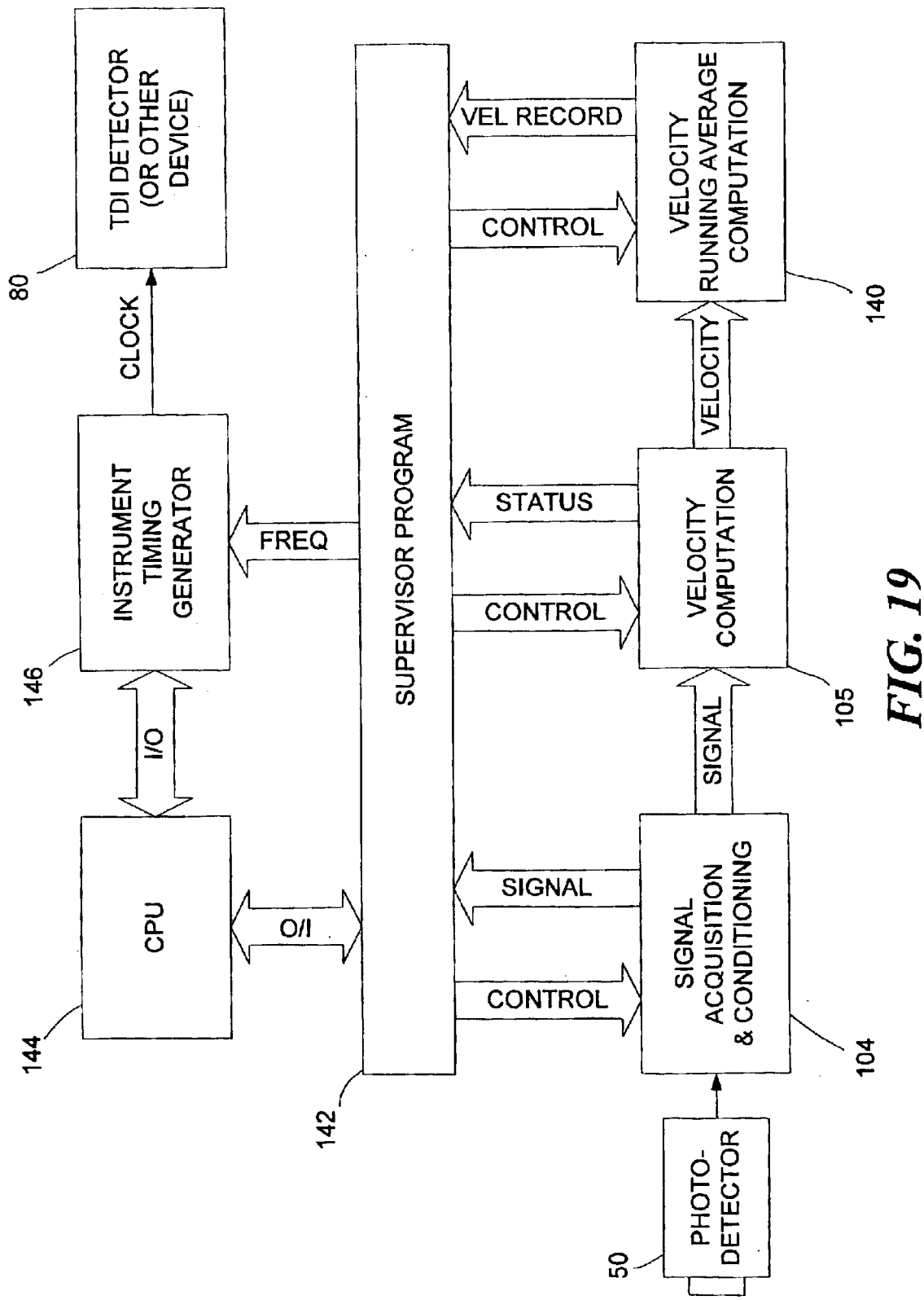
FIG. 19 is a block diagram of common components of flow velocity measurement systems, in accord with the present invention that are under the control of a system controller.

FIG. 19 is a functional block diagram of a signal acquisition and analysis system controlled by a supervisor program 142, preferably executed by a CPU 144 of a programmable computer. Alternatively, supervisor program 142 can be executed by a corresponding CPU in a digital oscilloscope, or by an ASIC chip. A signal from photodetector 50 is processed via signal acquisition and conditioning process block 104, velocity computation process block 105 (note that fast velocity computation process block 106 of FIG. 11 employs FFT processing, while, velocity computation process block 105 is more generalized, and can employ other types of signal processing, as opposed to just FFT signal processing), and a velocity running average computation block 140. Based on the velocity of an object that was determined, supervisor program 142 provides a clocking signal to a timing generator 146 that controls TDI detector 80. Note that the TDI detector is only one device exemplary device that can employ the present invention. It is expected that other types of devices can be provided a timing signal in this manner.

FDVM of Objects in Flow

Figure 20:
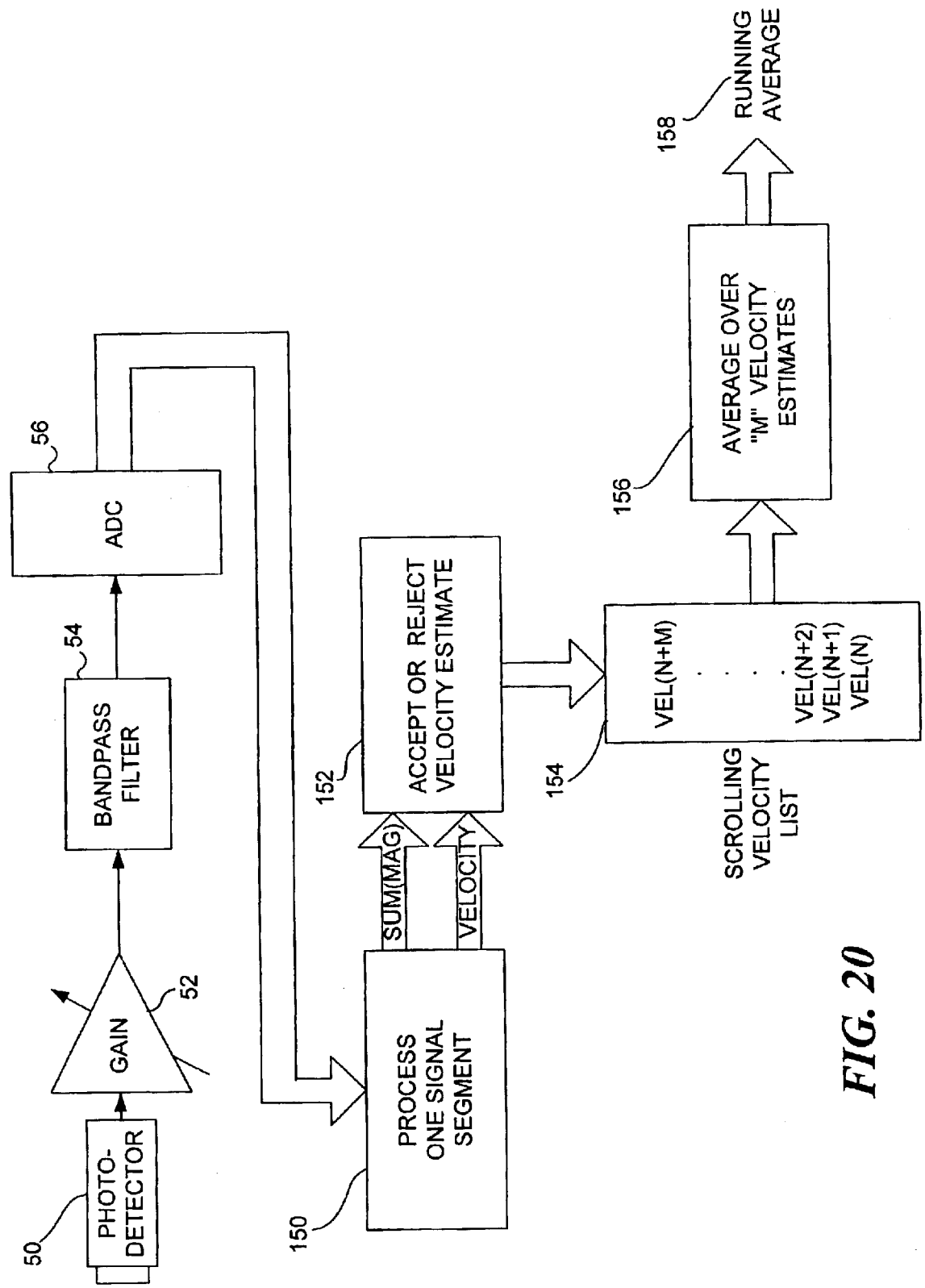
FIG. 20 is a block diagram illustrating the steps of the signal processing and velocity computation for a second preferred embodiment of the present invention.
Figure 21:
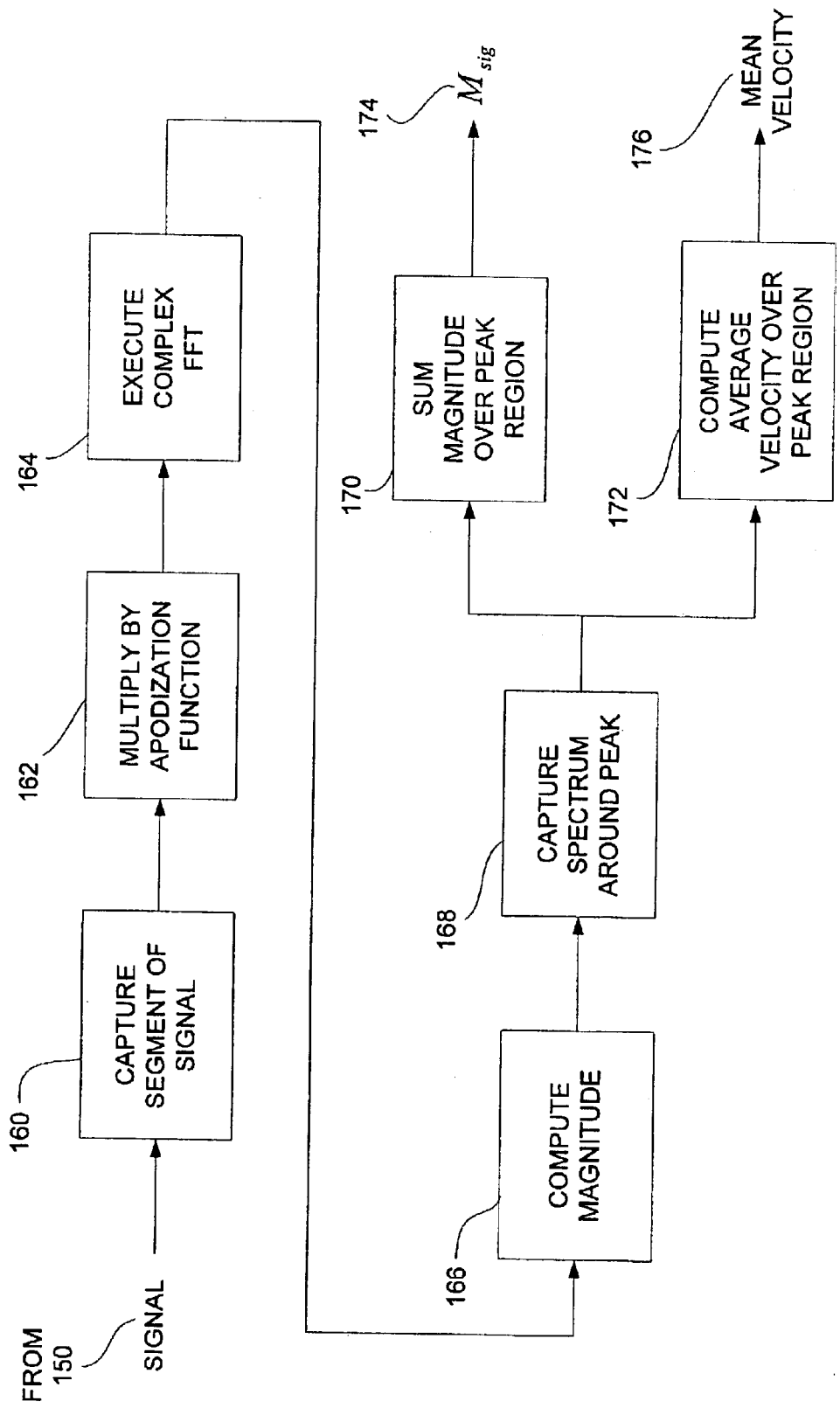
FIG. 21 is a block diagram illustrating the steps comprising the signal processing for the embodiment of FIG. 20.

In the second preferred embodiment of the present invention, the light from the objects is modulated by the optical grating, and the modulated light is sensed by the photodetector shown in FIG. 5. The functional blocks used to capture, process, and analyze the photodetector signal are shown in FIG. 20. Details of a multistage digital signal processing operation 150 for processing the incoming signal are illustrated in FIG. 21. The entire system, shown in FIG. 20, operates as a pipeline processor in which blocks of signal samples, and farther down the pipeline, parameters calculated from the blocks of samples are passed from one operation to the next in an uninterrupted sequence.

As explained above in connection with FIG. 6, the signal produced by photodetector 50 is input to variable gain amplifier 52. The output of variable gain amplifier 52 is filtered by bandpass filter 54 to remove the DC bias caused by stray light and by bias voltage of variable gain amplifier 52 and to eliminate frequencies above the Nyquist limit of ADC 56, this limit being equal to one-half of the sample frequency, $f_{samp}$. After bandpass filtering, the signal swings in both the positive and the negative direction around a mean value of zero.

ADC 56 samples the signal at frequency $f_{samp}$ and encodes the signal into a series of digital samples representing the signal amplitude at each sequential sample time. The converter must retain the bipolar nature of the signal by encoding the signal into a number system such as the 2's complement format, which accommodates both positive and negative numbers.

As an alternative, ADC 56 could be placed immediately after variable gain amplifier 52 and bandpass filter 54 could be implemented as a digital instead of an analog type filter. The signal applied to the ADC would then be unipolar, and the signal would be encoded into a simple binary number for processing.

In a multistage digital signal processing block 150, one signal segment is processed. Referring now to FIG. 21, in block 150, a sequential series of signal samples of predetermined length, N_segment, is analyzed to extract the mean frequency of the photodetector signal and to convert that frequency to an estimate of the object velocity. The first step 160 of this operation is to capture the desired number of samples for the segment from the incoming signal.

Optionally, the next signal processing step 162 applies an amplitude windowing or apodization function to the signal segment that was just captured. Without this apodization step, the abrupt truncation of the signal at the ends of the segment would spread the frequency components in the signal over a collection of sidebands, the frequency and amplitude of which conform to the Fourier Transform of a rectangular window, a sine function in frequency space. Those skilled in the art will recognize that apodization by a function such as the Hamming, Hanning, or raised cosine functions, for example, will substitute a smoother sideband structure of lower amplitude in place of the sine function. The reduced sideband amplitude improves the accuracy of estimating the mean frequency of the photodetector signal, especially in the presence of velocity dispersion. Alternatively, apodization can be performed optically by illuminating the FOV using a smooth-shouldered intensity profile, thereby eliminating the abrupt truncation of the signal at the edges of the FOV. In still another method of apodization, the ruling may be superimposed on a varying transmission gradient filter, which smoothly attenuates the optical signal at the edges of the FOV.

The optional apodization operation in step 162 is followed by execution of a complex FFT function in a block 164. The complex FFT algorithm is utilized by applying the signal as the real input to the FFT and applying an array of length N_segment with all values set to zero as the imaginary input to the FFT. Alternatives exist for utilizing the FFT algorithm more efficiently for real-number transforms, but those methods involve packing the input arrays in special patterns and unpacking the output arrays. Such methods can be used, however, to save processing time.

The resulting complex-number spectrum is then applied to an operator in a block 166 that converts the real and imaginary parts of the spectrum to the magnitude of the spectrum using the following relation:

$$M_j = \sqrt{\text{Re}_j^2 + \text{Im}_j^2}$$

where:
$M_j$=magnitude at sample j
$\text{Re}_j$=real part of sample j
$\text{Im}_j$=imaginary part of sample j.

Typically, this operation will be implemented using a lookup table or fast approximation algorithm to speed execution.

Typically, the velocity of the objects to be imaged with a TDI detector will deviate very little from the mean velocity. Consequently, the power in the spectrum of the signal from the photodetector will be concentrated in a narrow band around a mean frequency, and the spectrum outside this band can be ignored in the computation of mean frequency.

Figure 22:
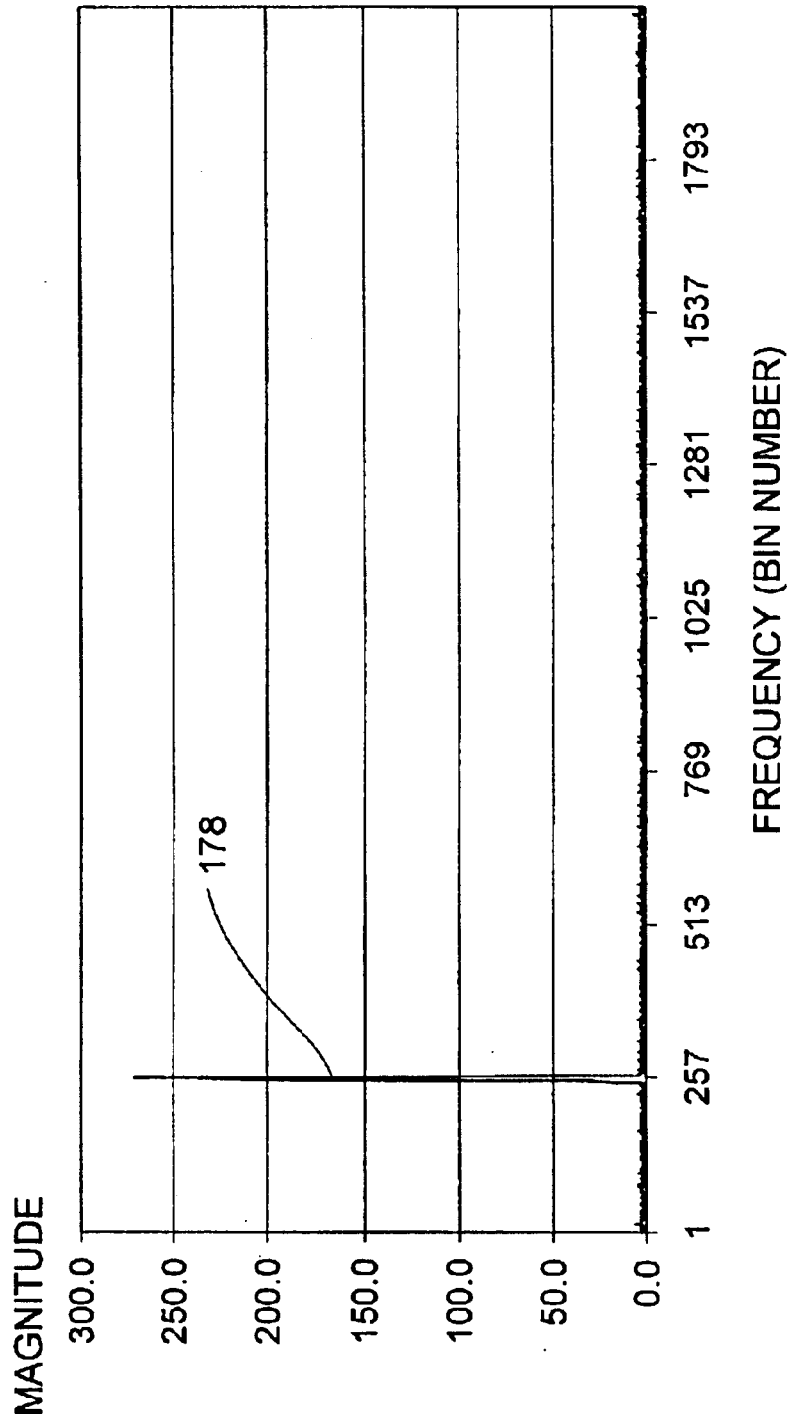
FIG. 22 is a graph of an exemplary spectrum of an unmodulated photosensor signal for a single object.
Figure 23:
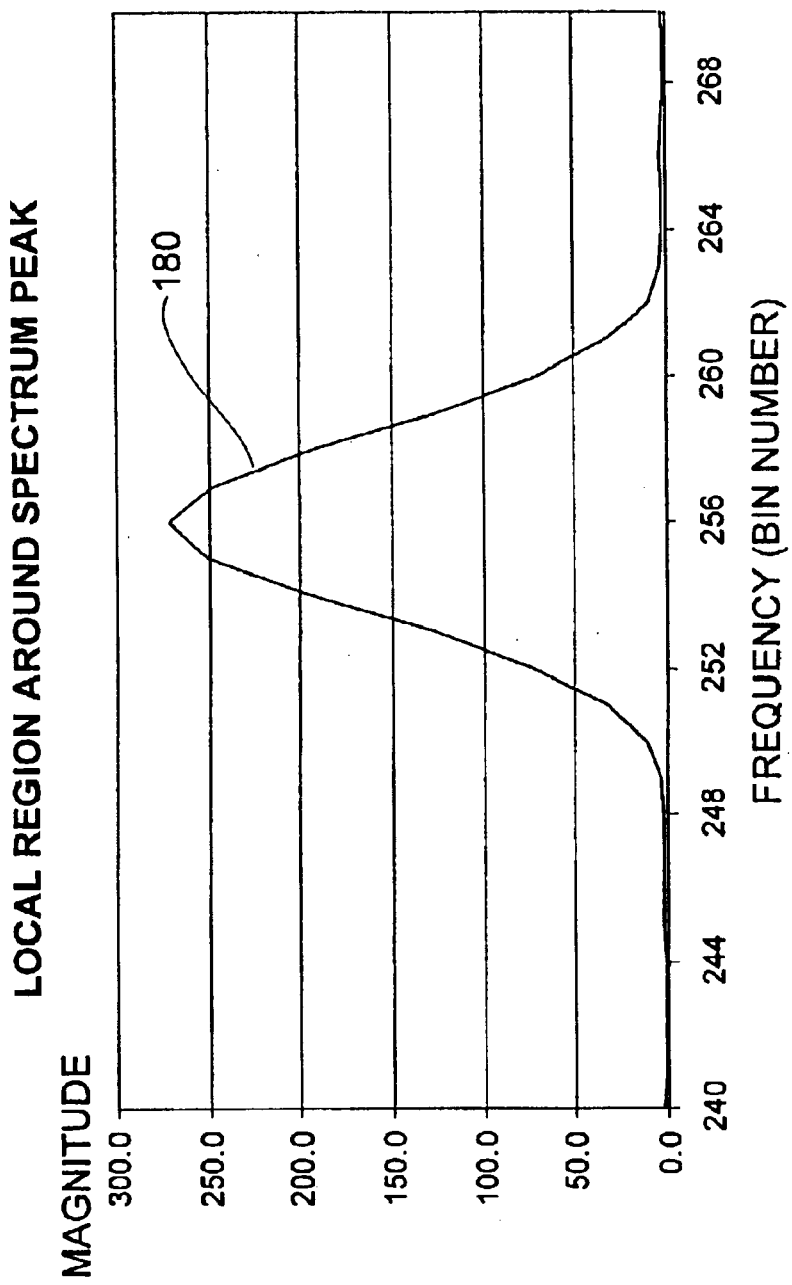
FIG. 23 is an enlarged view of the graph of FIG. 22, illustrating the signal peak.

FIG. 22 is the spectrum produced by a sinusoidal burst with center frequency 2500 Hz and a Gaussian-shaped envelope. A single object passing through the flow cell of a flow imaging system such as that illustrated in FIG. 9 might produce such a signal. A simple peak detector is applied to the spectrum in FIG. 22 in a block 168 of FIG. 21, to localize a region 178 of the spectrum of interest for analysis. FIG. 23 shows a segment 180 of the spectrum centered on the peak of the spectrum of the signal burst. This segment contains nearly all of the power in the spectrum and can be utilized for computing the mean velocity.

In a block 172 of FIG. 21, the mean velocity is determined by finding the mean frequency on the scale of FFT bins from the signal segment of FIG. 17. The following relation describes this calculation:

$$\bar{n} = \frac{\sum_{n=a}^{b} nS(n)}{\sum_{n=a}^{b} S(n)}$$

where:
a, b=endpoints of sample in window
S=magnitude of spectrum
n̄=mean FFT bin (floating point).

The mean frequency in Hz is computed from the mean FFT bin number as follows:

$$\bar{f}\ (\text{Hz}) = 2 \cdot \bar{n} \cdot f_{Nyq}/N$$

where:
$f_{Nyq}$=Nyquist frequency
N=FFT length
$\bar{f}$=mean frequency.

Finally, a mean velocity 176 is found by multiplying the mean frequency by the optical grating pitch:

$$\bar{v} = \bar{f} \cdot s$$

where:
s=grating pitch (microns)
v̄=velocity (microns/sec).

The velocity detection system must accommodate the possibility that very little or no signal was captured in the signal segment being processed. In the present embodiment of the invention, the magnitude of the spectrum integrated over the local region around the peak of the spectrum is computed in a block 170, as follows:

$$M_{sig} = \sum_{n=a}^{b} S(n)$$

where:
$M_{sig}$=integrated magnitude, this segment
S=magnitude of spectrum
a=first bin of local region around peak
b=last bin of local region around peak.

As will be appreciated from the description of the supervisor program for the velocity detection system that follows, a running record of the mean velocity will be maintained by the supervisor and used to establish the boundaries, a and b, of the local region for computing the mean frequency and an integrated magnitude 174.

Referring back to FIG. 20, the mean velocity and integrated signal magnitude from operation 150 are applied to a decision step 152. The decision step 152 yields two possible outcomes: (1) the SNR of the segment being processed is adequate for computing the velocity, so that the new velocity value is added to a velocity list 154, or (2) the SNR is inadequate (below a predefined value) for computing the velocity, and the velocity list remains unchanged. If a new velocity value is added to the velocity list, the oldest value on the list is deleted (once the list is full). Velocity list 154 and a running average calculation in a step 156 deliver a new velocity estimate every time a new signal segment is processed. The running average velocity is the average over a predetermined number of velocity values, m. The number of values, m, used in the running average can be increased to improve the accuracy of the running average or decreased to improve the responsiveness of the velocity detector to rapid changes in velocity.

Figure 24:
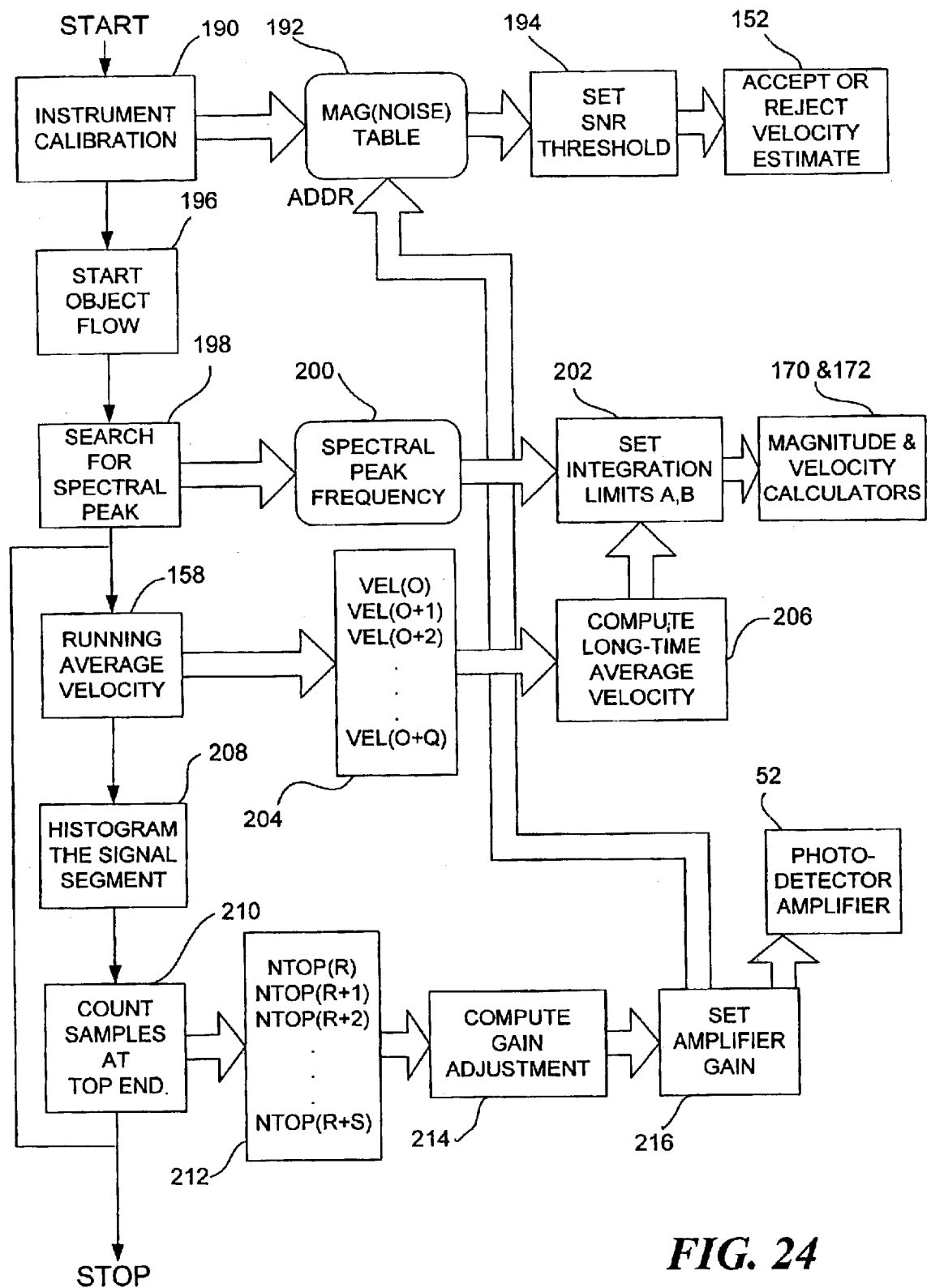
FIG. 24 is a block diagram illustrating the steps employed by the supervisory program for controlling the second embodiment of the present invention.

The velocity detector must adapt to variations in flow velocity and photodetector SNR in order to produce accurate and reliable velocity estimates. Supervisor program 142, shown in FIG. 19, is used to control the velocity detector and to coordinate the operations of the velocity detector with those of the rest of the imaging system. FIG. 24 is a flowchart showing the steps implemented by the supervisor program for the second embodiment of the present invention. The program's three principal outputs, the SNR decision threshold, the spectrum integration limits, and the photodetector amplifier gain, are fed back to the velocity measurement system to optimize its performance.

Operation of the velocity detection system is initiated with an instrument calibration step 190, in which the noise from the photodetector channel is determined and analyzed in the absence of an optical signal. This can be accomplished by turning off the light sources in the system or stopping the flow of objects through the flow cell. The purpose of the noise measurement is to establish a reference against which the information-bearing signal will be compared for setting a threshold for accepting or rejecting velocity measurements.

The calibration operation measures the noise level at a plurality of amplifier gain settings and stores these measurements in a table 192 of noise level vs. gain. Table 192 is used to select an initial gain setting for amplifier 52. As the amplifier gain is varied to regulate the signal strength during normal operation, the correct noise level for setting the decision threshold is read from table 192 and applied to threshold calculator 194. Once the calibration operation has been completed, the light source or sources are turned on, and objects are introduced into the flow stream for image acquisition, as shown in a step 196.

The next task of the supervisor program is to search for the peak in the spectrum in a step 198 and set the upper and lower boundaries of the spectral region to be analyzed. In the absence of any a priori knowledge of the flow speed, this initial search must span the entire range of frequencies in the spectrum, and may entail capturing a number of signal segments until a strong peak representing a spectral peak frequency 200 is found. The location of that peak will be used to set the local region boundaries, using knowledge of the expected width of the spectrum. This width is a function of the beam profile of the illumination field, the shape of the apodization function, and the predicted variance of object velocities. This information will be understood from the design of the instrument.

With the photodetector amplifier gain set to a starting value and the decision threshold and integration limits established, pipeline processing of signal segments commences. Each time a segment is processed, running average velocity value 158 is added to a list 204 and the oldest value in the list is deleted. The velocity values in list 204 are then averaged in a step 206. This long-time average of the velocity is used in a step 202 in which the boundaries of the local spectral region to be analyzed are set. The process of regulating the integration limits constitutes a feedback control loop in the supervisor program. The response time of this loop can be modified by adjusting the number of samples maintained in list 204 and averaged in step 206.

The gain of the photodetector amplifier is regulated during system operation as well, in order to optimize the SNR of the velocity detector as specimen characteristics change. The amplifier gain regulation system of the supervisor program in a step 208 provides for creating the histogram of each signal segment, counting the number of samples occupying a predetermined number of levels near the top of the analog-to-digital converter output scale in a step 210, maintaining a list of the most recent count results in table in a step 212, and analyzing that table to generate a gain adjustment in a step 214.

The time of arrival of objects in the FOV of the velocity measurement system is a random variable. If the specimen contains a high concentration of objects, the probability that an object will pass through the FOV in a given time interval is high, and the count table of step 212 will contain many samples useful in setting the amplifier gain. However, if the specimen contains a very low concentration of objects, many of the signal segments processed by the velocity detection system will be devoid of signal, and the count values stored in the count table of step 212 for those segments will be zero. Those skilled in the art of automatic gain control systems will recognize this problem as similar to that of regulating the gain in radio receivers or studio microphone amplifiers, in which the signal being processed may vary widely in amplitude and be interrupted. The common practice in such cases is to use a "fast attack," "slow recovery" feedback control system. In such a system, the sudden arrival of a high-amplitude signal will be met with a fast reduction of amplifier gain to prevent saturation. On the other hand, a prolonged interruption of the signal is met with a slow increase in gain, on the premise that a large signal is likely to arrive soon, but a persistent loss of amplitude, requiring higher gain may have occurred. The gain adjustment determined in step 214 will use a "fast attack," "slow recovery" algorithm to regulate the photodetector amplifier gain. Determination of running average 158, and steps 208 and 210, and their associated feedback control mechanisms will sustain sequential processing of signal segments until terminated by the supervisor program.

The new gain setting is set in a step 216 for variable gain amplifier 52 in regard to noise calibration table 192. The response time of the gain control feedback loop can be modified by adjusting the number of samples maintained in table 212 and analyzed in step 214.

TDVM of Objects Using a Single Uniform Pitch Optical Grating

In the third preferred embodiment of the present invention, the light collected for velocity measurement is modulated by an optical grating having a substantially uniform pitch and sensed by the photodetector shown in FIG. 5, just as in the second embodiment. The analysis of the photodetector signal, however, is performed in the baseband domain. Baseband demodulation is frequently used in communications and other signal processing applications for receiver tuning and carrier rejection. The fundamental architecture of a baseband demodulator with the additional capability of splitting the signal into upper and lower sidebands, is shown in FIG. 25 and is referred to herein as "the double-sideband receiver."

Figure 25:
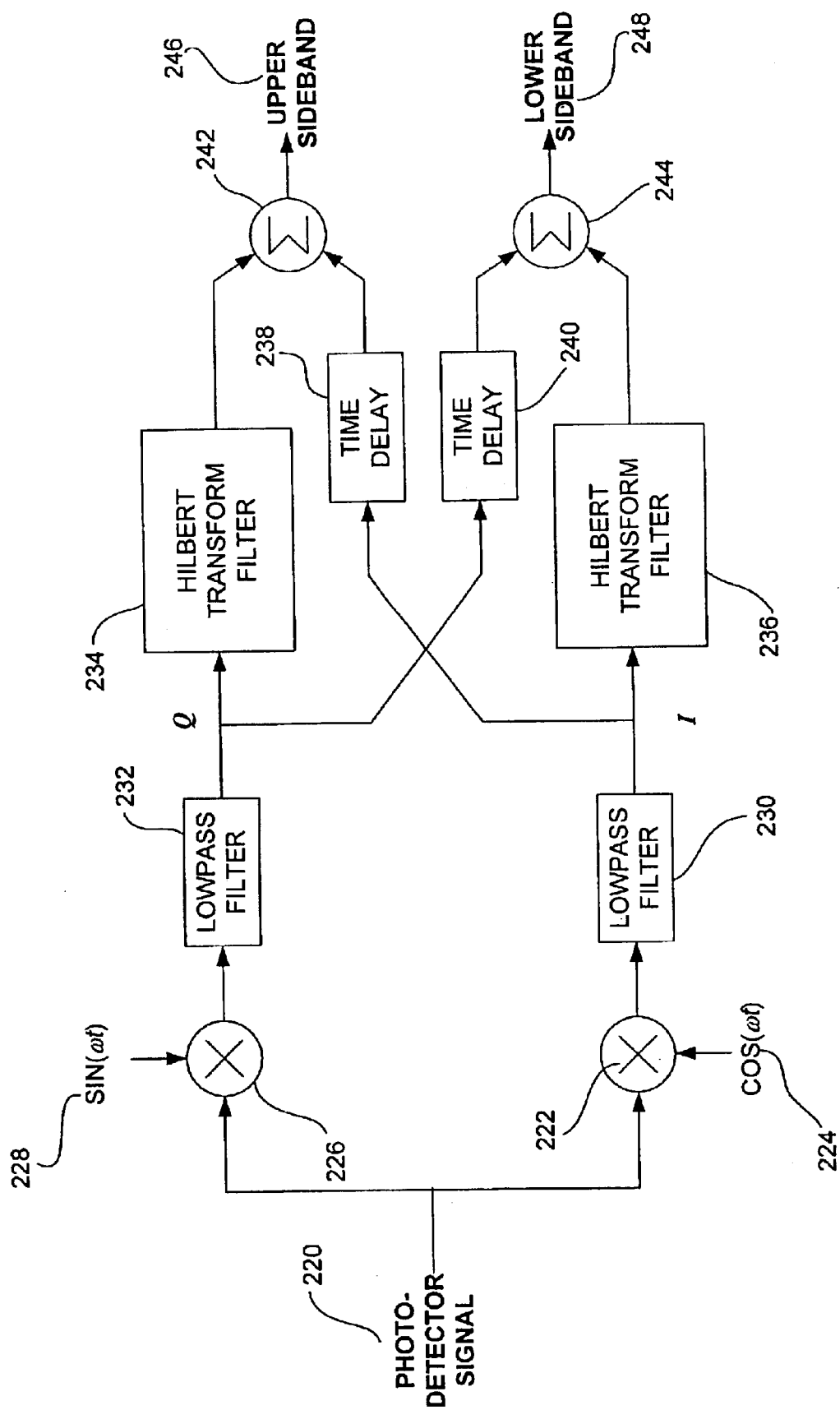
FIG. 25 is a block diagram of a double sideband receiver for use in a third embodiment of the present invention.

As shown in FIG. 25, an incoming signal from the photodetector is applied to multipliers (or mixers) 222 and 226, which multiply the signal by two continuous sinusoidal wave functions, called local oscillator signals. The two local oscillator signals are at the same frequency, but shifted in phase ninety degrees relative to one another. That is, a first local oscillator signal 224, which is the in-phase local oscillator signal, is a cosine function, while a second first local oscillator signal 228, which is the quadrature-phase local oscillator signal, is a sine function. The mixers are followed by lowpass filters 230 and 232, which complete the baseband demodulation.

The effect of multiplying the signal from the photodetector by a sinusoid of frequency fLO is to offset the spectrum of the incoming signal upward by fLO, to create sum frequencies, and downward by -fLO, to create difference frequencies. In FIG. 26, a sinusoidal burst with the spectrum shown in a graph 250 at a center frequency of 1500 Hz is applied to mixers 252 and 256, driven by local oscillator signals 254 and 258, set to 2000 Hz. At the output of the mixers, the center frequencies in the spectrum are the difference frequency, 500 Hz, and the sum frequency, 3500 Hz, as shown in graph 264. Low-pass filters 260 and 262 suppress the sum frequencies, leaving only the difference frequencies in the I(t 268 and Q(t) 266 signals, as shown in a graph 270.

The lowpass filter outputs are the I and Q signals, i.e., the in-phase and quadrature-phase signals. FIG. 27 shows how signals entering and leaving the baseband demodulator might look on an oscilloscope. Each time-sample is a complex number representation of the input signal 272, with the I channel 268 representing the real part of the complex signal, and the Q channel 266 representing the imaginary part of the complex signal. Graph 276 shows the in-phase output signal, while graph 274 shows the quadrature-phase output signal. The I,Q pair conveys both the magnitude of the signal and the phase of the input signal 272 relative to the local oscillators. A time series of I,Q pairs can represent both positive and negative frequencies, which derive from frequencies above the local oscillator frequency and below the local oscillator frequency, respectively. The time series of I,Q pairs is often referred to as the "analytical signal."

The magnitude and the phase of the input signal can be calculated from the analytical signal using the vector operations shown in FIG. 28. The magnitude of a signal 282 is computed in a step 278. I(t) and Q(t) are the Cartesian projections of the vector M(t), therefore M(t) is just the length of the hypotenuse of a right triangle with the other two sides being I(t) and Q(t). The equation for calculating M(t), then, is:

$$M(t) = \sqrt{(I(t))^2 + (Q(t))^2}.$$

Accordingly, the angle between the real, I(t), axis and the hypotenuse, M(t), is the inverse tangent of Q(t)/I(t), or:

$\Phi(t) = \arctan[Q(t)/I(t)]$.

The analytical signal offers a versatile method for tracking the photodetector signal frequency in the velocity detector. The frequency at every sample time is found by taking the time derivative of the phase of the analytical signal in a step 280. However, as seen in a graph 284 of $\Phi(t)$, the phase is a periodic function. The values $\pi$ and $-\pi$ define the same angle, where the abrupt transitions occur in graph 284.

In order to calculate a phase derivative for each time sample, the periodic $\Phi(t)$ function must be converted to a continuous function. FIG. 29 illustrates the unwrapping of the phase of a constant-frequency signal. The function $\Phi(t)$ is shown in a graph 288. A polar plot 286 shows a rotating vector representation of a constant amplitude, constant frequency signal. It can be seen from plot 286 that the phase will make an abrupt transition from $\pi$ to $-\pi$ once per period. A phase unwrapping algorithm 290 senses these transitions and corrects for them to produce a monotonically increasing function of phase, as shown in a graph 292.

FIG. 30 describes the phase unwrapping algorithm. In a first step 294, the change of phase from one time sample to the next is computed without regard to the values of $\Phi(n)$ and Φ((n−1). In the next two stages, steps 296 and 298, the presence of a transition across the π,−π boundary is sensed and the phase derivative is corrected. The first part of both steps 296 and 298 is to detect that the phase has moved from one half-plane to the other half-plane. If Φ(n−1) was zero or positive, then the transition was from the upper half-plane to the lower half-plane, and the step 296 is executed. If Φ(n−1) is negative, then the transition was from the lower half-plane to the upper half-plane, and the step 298 is performed. In step 296, a further test is performed to determine if Φ(t) has changed in the negative direction by more than π. If so, then the transition between half-planes was at the π,−π boundary. In this case, an offset of +2π is applied to ΔΦ, which eliminates the impact of the boundary transition. In a similar manner, if step 298 detects that the phase has rotated across π,−π boundary in the clockwise direction, it subtracts 2π from ΔΦ to eliminate the impact of the boundary transition. Application of the unwrap algorithm to the phase signal from the baseband demodulator is used to generate a smooth phase plot, $\Phi_m(t)$, as shown in graph 292 of FIG. 29. The slope of this plot is the radial frequency, ω(t).

Any signal generated by a physical system will contain some random noise. Because ω(t) is computed using a difference operator, and true random noise is uncorrelated from sample to sample, the accuracy of the ω(t) calculation will degrade rapidly with decreasing SNR. For this reason, time samples of ω(t) are accepted into the velocity computation only if the magnitude of the signal is above a predefined threshold. This concept is illustrated by FIGS. 31A and 31B. In a graph 302 of FIG. 31A, a threshold of 0.1 is applied to the magnitude, M(t). The baseband frequency is computed only for those samples exceeding the threshold, yielding a result like that seen in a graph 308 of FIG. 31B. The term "fractional frequency" 310 used in graph 308 means the frequency expressed as a fraction of the Nyquist limit in baseband. The fractional frequency can have a value in the range from 0.0 to 1.0.

FIG. 32 shows the signal processing and data pathways for the third embodiment. The signal from photodetector 50 is applied to variable-gain amplifier 52, the gain of which is regulated by the supervisor program to optimize SNR. The amplified signal is applied to bandpass filter 54 to remove DC offset and to limit the signal bandwidth to prevent aliasing. The filtered signal is converted to a sequence of digital sample by ADC 56. Mixers 222 and 226 and lowpass filters 230 and 232 (FIG. 25) are implemented in the baseband conversion of a step 311. The baseband signal pair I(n), Q(n) is used for two steps. The first is the generation of the upper sideband and lower sideband signals 314 and 322 in a step 312. The second is the measurement of the velocity of objects passing through the flow cell.

FIG. 33 illustrates the generation of the upper and lower sideband signals from the I,Q signal pair. An I(n) signal 326 and a Q(n) signal 328 are each processed by the Hilbert Transform operator, applied in steps 234 and 236. Those skilled in the art will recognize that this operator delays the input signal by π/2 radians (90 degrees). Note that the phase rotation is not a time delay, because the rotation is π/2, independent of the frequency of the incoming signal, over a broad range of frequencies. However, a time delay is inherent in the Hilbert Transform algorithm, and must be matched by time delays 238 and 240. The final stage of the sideband separation is that of summing at node 242 the rotated Q(n) signal with the un-rotated I(n) signal to generate an upper sideband signal, USB(n) 330, and of summing at node 244 the rotated I(n) signal with the unrotated Q(n) signal to generate a lower sideband signal, LSB(n) 332. Summation at node 242 cancels signal vectors rotating counterclockwise in I,Q plane 286 (see FIG. 29) and reinforces those rotating clockwise in the I,Q plane. Summation at node 244 cancels signal vectors rotating clockwise in I,Q plane 286 and reinforces those rotating counterclockwise in the I,Q plane. The upper- and lower-sideband signals are used by the supervisor program during system start-up to search for the photodetector frequency and to set the local oscillator frequency for the baseband demodulator.

The I,Q complex signal is also applied to the pipeline process in a block 316 (see FIG. 32), which detects and segments signals from individual objects in the flow stream, tests these signals against predetermined acceptance criteria, and computes the object velocity from the accepted signals. The details of the steps implemented in block 316 are shown in FIG. 34.

The signal threshold concept illustrated in graph 302 (FIG. 31A) is used to segment the signal stream into sample packets, each of which represents an object or an aggregate of objects in the flow stream. The most accurate velocity measurements are those derived from the signals from isolated single objects. Signals from aggregate objects, i.e., signals from multiple objects coexisting in the FOV of the velocity detector, carry phase errors caused by the interference among the signals from the individual objects. The segmentation then accepts only those signals with an envelope width close to that predicted for a single object passing through the FOV at the current expected velocity. Because the envelope width is inversely proportional to velocity, the supervisor program tracks the known velocity and corrects the width limits as the velocity changes.

Referring to FIG. 34, each base pair of the I,Q complex signal is analyzed starting in a block 334. Segmentation of a packet begins when the magnitude of the signal crosses a threshold 371 while rising, detected in an step 336, and ends with the magnitude falls back across threshold 371, detected in a step 342. The sample count, n, and the unwrapped phase, $\Phi_m(n)$, are set to zero in a step 338 when the rising edge of the packet is detected. The unwrapped phase is computed in a step 344 for each sample following the rising edge, and the sample count is incremented each time a new sample is acquired in a step 340. Once the falling edge of the packet is detected, the sample count, n, is taken as a width 364 of the packet. The phase samples $\Phi_m(0)$ through $\Phi_m(n)$ are used in the computation of the average frequency of the signal packet, and, subsequently, the velocity of the object.

However, each packet must meet two criteria before being accepted as a useful signal. First, the packet width is compared to upper and lower width limits 366 in a step 346. The packet is rejected if the width falls outside those limits. The radial fractional frequency, ω(n), is computed for each sample within the packet in a step 348. The unwrapping algorithm cannot deliver values outside of the range from −π to π, since the Nyquist limits are −π and π radians/sample. Division by π in operation 348 expresses ω(n) as the dimensionless fraction of the Nyquist limit. The variance is computed for the ensemble of values ω(1) through ω(n) in a step 350 and compared with a maximum limit 373 in a step 360. This limit is a constant determined empirically for delivery of the required accuracy in the velocity measurements while limiting the number of rejected objects.

If the wave packet is accepted as representing a single object and as having an acceptably low frequency variance, an object velocity 368 is computed in a step 362 as follows:

$$\overline{f}_{bb} = \frac{\sum_{i=1}^{n} \omega(i)}{n} \cdot f_{Nyq}$$

and $$v_o(\text{mm/sec}) = (\overline{f}_{bb} + f_{LO}) \cdot s$$

where:
  $\omega(i)$=fractional frequency for sample i
  $f_{Nyq}$=Nyquist frequency for baseband
  $\overline{f}_{bb}$=mean baseband frequency (Hz)
  $f_{LO}$=local oscillator frequency (Hz)
  s=grating pitch (mm)
  $v_o$=particle velocity (mm/sec).

In FIG. 35A, a graph 370 represents a plot of the baseband frequency versus time for the magnitude signal shown in graph 302 (FIG. 31A), but with only the qualified signals retained. A graph 372 in FIG. 35B shows the series of object velocities computed in operation 362 (see FIG. 34) from the baseband frequency data shown in graph 370.

For each accepted object, a velocity, $v_o$, is delivered to a scrolling object velocity list 318 of FIG. 32. Every time a new velocity value is added to the scrolling list, the oldest value is removed from the list. A running average computation in a step 320 constantly determines a running average 324 of the values in the scrolling velocity list at a repetition rate determined by the supervisor program.

FIG. 36 shows the structure of the supervisor program for the third embodiment of the present invention. Operation of the velocity detection system is initiated with the instrument calibration in a step 374, in which the noise from the photodetector channel is determined and analyzed in the absence of an optical signal. This step can be accomplished by turning off the light sources in the system or stopping the flow of objects through the flow tube. The purpose of the noise measurement is to establish a reference against which the information-bearing signal will be compared for setting a threshold for accepting or rejecting phase samples.

The calibration operation measures the noise level at a plurality of amplifier gain settings and stores these measurements in a table 376 of noise level vs. gain. Table 376 will be used to select an initial gain setting for variable gain amplifier 52. As the amplifier gain is varied to regulate the signal strength during normal operation, the correct noise level for setting the decision threshold will be read from table 376 and applied to a threshold calculation in a step 378. Once the calibration operation has been completed, the light source or sources are turned on, and objects are introduced into the flow stream for image acquisition, as shown in a step 380.

The next task of the supervisor program shown in a step 382, is to search the spectrum for the photodetector signal. In the absence of any a priori knowledge of the flow speed, this initial search must span the entire range of frequencies in the spectrum, and may entail sweeping the spectrum a number of times until a strong signal is found. Step 382 sweeps the frequency of the local oscillator and captures a short time segment of upper sideband 330 and lower sideband 332 signals (see FIG. 33). As the local oscillator is swept across the actual frequency of the photodetector signal, the lower sideband amplitude will increase and then drop. Then the upper sideband amplitude will increase and then drop. For the broad sweep to locate the approximate photodetector frequency, the local oscillator is varied in large increments to speed the search, and the search in step 382 measures the root mean square (rms) sum of the sidebands as follows:

$$P_{usb} = \sum_{i=1}^{N} U^2[i]$$

$$P_{lsb} = \sum_{i=1}^{N} L^2[i]$$

$$P_{sum} = \sqrt{P_{usb}^2 + P_{lsb}^2}$$

where:
  U[i]=upper sideband amplitude of ith sample
  L[i]=lower sideband amplitude of ith sample
  N=number of time samples in tested signal segment
  $P_{sum}$=integrated sideband power for signal segment.

FIG. 37 is a graph 406 of the integrated sideband power versus the local oscillator frequency for the broad search sweep. The width of a power envelope 408 is two times the bandwidth of lowpass filters 230 and 232 (see FIG. 25) in the baseband demodulator. The desired local oscillator frequency is located at a dip 410 between the two peaks in the power envelope. However, this frequency is poorly resolved because of the large steps used in search sweep 382.

Referring back to FIG. 36, a more accurate estimate of the desired local oscillator frequency is made in a step 384 by varying the local oscillator frequency over a narrow range covering the power envelope. This narrow sweep is illustrated by a graph 414 in FIG. 38, which is an overlay of an upper sideband power 416, called $P_{usb}$, and a lower sideband power 418, called $P_{lsb}$, as a function of local oscillator frequency. The search in step 384 of FIG. 36 finds a frequency 420 in FIG. 38 at which the upper sideband and lower sideband are of equal power. As will be evident in FIG. 38, this frequency is approximately 2500 Hz. Under this condition, the local oscillator frequency is approximately equal to the photodetector signal center frequency, and the baseband demodulation system can be used to measure the exact photodetector signal frequency.

With the magnitude threshold and the local oscillator frequency set, object processing can commence. During object processing, the supervisor program continuously monitors the sideband signals in a step 388 (FIG. 36) using sample locations accepted by signal processing step 316 (see FIG. 32). The selected sideband samples are used to monitor the balance between the power in the upper sideband signal and that in the lower sideband signal. Imbalance between the two sideband signals indicates that the photodetector frequency has shifted and that the local oscillator frequency should be adjusted. The sideband balance will be repeatedly computed in a step 388, the balance values stored in a table 390, adjustments to the local oscillator will be computed in a step 394, and applied in a step 386. The number of values maintained in table 390 can be modified to adjust the response time and stability of the local oscillator feedback loop.

The sideband signal levels are checked to determine if they have been lost in a step 392. If both the upper sideband and lower sideband signals are lost, the supervisor program interrupts signal processing and returns to search routine 382 to tune the system back to the photodetector signal frequency, if possible. The supervisor program will remain in the search mode until a signal is acquired or the velocity detection system is turned off.

The gain of the variable gain amplifier is regulated during system operation as well, in order to optimize the SNR of the velocity detector as specimen characteristics change. The amplifier gain regulation system of the supervisor program implemented in a step 396 creates the histogram of the peak magnitudes of the accepted signal packets. A step 398 provides for counting a number of samples occupying a pre-determined number of levels near the top of the analog-to-digital converter output scale, and maintains a list of the most recent count results in a table 400. That table is analyzed to determine a gain adjustment in a step 402. The gain adjustment implemented in step 402 will use a "fast attack," "slow recovery" algorithm, as described above, to regulate the gain of the variable gain amplifier.

The new gain setting is set in a step 404 and is provided to a noise calibration table 376. The response time and stability of the gain control feedback loop can be modified by adjusting the number of samples maintained in table 400 and analyzed in step 402.

TDVM of Objects Using Paired Nonuniform Optical Gratings

In the fourth preferred embodiment of the present invention, the light collected for velocity measurement is modulated by two optical gratings and sensed by two photodetectors, as shown in FIG. 43. The velocity is measured by cross-correlating the signal from the first photodetector with that from the second photodetector, yielding a time-of-flight value that is converted into a velocity of the object.

The cross-correlation of two signals is carried out by convolving the two signals and extracting information from the output of the convolution operation, which is called the correlogram. The convolution in the time domain is defined by the following equation:

$$f_1(t) * f_2(t) = \int_{-\infty}^{\infty} f_1(\lambda) f_2(t-\lambda) d\lambda.$$

The value of the convolution for every time sample, t, is the sum over infinity of the product of the two functions, but with the second function offset by time t. The utility of the convolution operator lies in the fact that it is equivalent to multiplication in the frequency domain:

Given the general notation:

$F(e^{j\omega})$=the Fourier Transform of $f(t)$ if $f_3(t)=f_1(t)*f_2(t)$ then $F_3(e^{j\omega})=F_1(e^{j\omega}) \cdot F_2(e^{j\omega})$.

A filter with a desired frequency response H(ejω) can be implemented as a time-domain operation, for example, by applying its inverse Fourier Transform, h(t), in the convolution integral. In the present invention, however, the utility of the convolution operator is in the measurement of the time delay between two signals. In the simplest case, the two signals are identical to one another, except that the second signal is delayed by time t0. As shown in the following equations, applying time delay to a signal is equivalent to convolving that signal by the delayed impulse function, δ(t−t0):

$f_2(t)=f_1(t-t_0)$ then $f_2(t)=f_1(t)*\delta(t-t_0)$.

Because convolution is associative, the problem of convolving the first signal $f_1(t)$ with the second signal, $f_2(t)$, can be solved by convolving $f_1(t)$ with itself and time delaying the result. Thus, $f_1(t)*f_2(t)=f_1(t)*f_1(t)*\delta(t-t_0)$ if $f_3(t)=f_1(t)*f_1(t)$ then $f_1(t)*f_2(t)=f_3(t-t_0)$.

Conversely, it is possible to measure the time delay between two signals by convolving one with the other and detecting the amount of time delay in the result.

FIG. 39 illustrates the convolution of two similar signals 422 and 424, which are the inputs of a convolution operator 426 arriving at different times. A correlogram 428 is a plot of the amplitude of the integrated product of signals 422 and 424. The horizontal axis of the correlogram represents the time delay applied to signal 422 relative to signal 424 using the convolution operation, scaled in units of time samples. A delay of around 400 samples is required to align signal 422 with signal 424, which is evident from the peak value of the correlogram amplitude. Note that the correlogram is broader than either of the two signals. This condition can be understood from the recognition that convolving a signal with itself is equivalent to squaring the spectrum of the signal, a step that compresses the spectral distribution. Narrowing the bandwidth of a signal broadens the signal in the time domain.

In the velocity detection system, the signals 422 and 424 might have been generated by two objects traversing an optical grating 432, as shown in FIG. 40. A graph 430 represents the Gaussian illumination profile applied to the field of optical grating 432. An object traversing the illumination profile will generate a signal with a Gaussian envelope and an oscillation frequency directly proportional to the velocity of the object and inversely proportional to the optical grating pitch.

Detecting the peak of correlogram 428 might be accomplished using a simple peak detector. The correlogram is broad, however, and the peak of the envelope might not coincide with the peak of an oscillation cycle. More elaborate detection schemes might improve the accuracy, but it is also useful to generate a narrower correlogram with a more clearly defined peak. This objective is accomplished by using an optical grating 436 shown in FIG. 41. Optical grating 436 has a nonuniform pitch, with line width (opaque and transparent bar width) decreasing linearly from the left end of the optical grating to the right end of the optical grating. The optical grating is aligned with a beam profile 434. Graphs 438 and 440 in FIG. 42 represent signals that could be generated by photodetectors in response to the light from two objects passing through optical grating 436. A resulting correlogram 442 is more compact than correlogram 428, suggesting that the time delay value might be extracted more easily from correlogram 442 than from correlogram 428.

The preferred embodiment of the correlation-based signal generation system uses a detection system that takes advantage of the nonuniform optical grating pitch. FIG. 43 illustrates the components used in the preferred embodiment. Light source 12 and lens 36 illuminate the FOV of flow tube 16 for the purpose of velocity measurement. The optical system comprising lenses 40,44, and 78 and beam splitter 76 form images of the objects passing through the FOVs on two optical gratings 444 and 446 having nonuniform but identical patterns of opaque and transparent bars.

As shown in FIG. 44, images 450 and 452 of optical gratings 444 and 446 are aligned end-to-end along the axis of flow. The boundary between the two images is aligned with the midpoint of an illumination profile 454. Light scattered or emitted by objects in the flow stream is modulated by optical gratings 444 and 446 and the modulated light is delivered to photodetectors 50 and 50*a* by lens 48 and a lens 448, respectively (see FIG. 43).

FIG. 45 illustrates the performance of the correlation operation for signals generated using the optical grating geometry shown in FIG. 44. A signal 456, produced in response to light modulated by optical grating 444 at the upstream side of the illumination field, grows in amplitude and increases in frequency with time, and terminates when the object moves into the field of downstream side of the illumination field. A signal 458, produced in response to light modulated by optical grating 446 at the downstream side of the illumination field, starts at high amplitude and low frequency. The amplitude decays with time as the frequency increases. A correlogram 460 shows a very distinct peak at the exact delay value that brings the two signals into alignment.

FIG. 46 shows an expanded view 462 of correlogram 460. For this view, the delay limits of the cross-correlation operation 426 were expanded to show that as the delay of signal 458 approaches the delay for optimal alignment, it first passes through a region 466 in which the correlogram appears very noisy. This region is where the high-amplitude part of signal 456 is aligned with the high-amplitude part of signal 458. However, the particular optical grating configuration shown in FIG. 44 provides the benefit that a primary peak 464 of correlogram 460 is bordered on both sides by very low-level signals 468. The noisy region of the expanded correlogram is avoided by using only those delay values close to the actual time of flight of the objects from a location on the upstream grating to the corresponding location on the downstream grating. A feedback loop in the supervisor program is used to regulate the convolution time delay limits to maintain this condition.

FIG. 47 shows the functional processing blocks used for the signal acquisition and processing for this embodiment of the present invention. The signals from photodetectors 50 and 50*a* are applied to variable-gain amplifiers 52 and 52*a*, respectively. The outputs of the amplifiers are applied to bandpass filters 54 and 54*a* to eliminate DC bias and to prevent aliasing when the signals are sampled by ADCs 56 and 56*a*. The digital outputs of the ADCs are delivered to a signal processing stage 470, which accepts a signal segment of a predetermined length and delivers an estimate of the object velocity to a scrolling velocity list 472, if acceptable signals from objects traversing the flow cell are present in that segment. If a new velocity value is delivered by the signal processing operation, it is added to list 472 and the oldest value on the list is deleted. A step 474 delivers the average of the velocity values in list 472 at the rate at which signal segments are captured in the signal processor to facilitate computation of a running average 476.

FIG. 48 shows the detailed architecture of the signal processing operation. For every cycle interval of the signal processor, concurrent segments of the digitized signals from photodetectors 50 and 50*a* are captured in steps 478*a* and 478*b*. The captured segments are simultaneously applied to magnitude calculators 480*a* and 480*b*, and to a step 482, which provides for determining a cross-correlation. Each magnitude calculator uses the following algorithm for computing the signal level:

$$M_j = \sum_{i=1}^{N} |A[i]|$$

where:
  N=length of the signal segment
  A[i]=value of the ith sample of the segment
  $M_j$=magnitude of the jth signal segment.

The magnitude values are sent to supervisor program 486 to be used to regulate the photodetector amplifier gain.

The convolution (or cross-correlation) carried out in step 482 generates the correlogram using the following algorithm:

for (k=Min_Delay; k<=Max_Delay; k++)

```
{
    m = k - Min_Delay;
    for (i = 0; i <= Correlation_Length; i++
    {
        j = k + i;
        C[m] += Signal 1[i]* Signal 2[j];
    }
}
```

FIG. 49 illustrates the results of the correlation algorithm. A signal segment 496 from the first photodetector is convolved with a signal segment 498 from the second photodetector through a series of multiply-and-accumulate operations to generate a correlogram 508. For each value in correlogram 508, the first P samples, where P=Correlation Length, of signal 496 are multiplied by the corresponding samples of signal 498 from sample Q, where Q=Delay, to sample R, where R=Delay+Correlation Length. The products of the sample-by-sample multiplication are summed to produce the values of the correlogram. The Delay value begins at a Min_Delay 504 and advances one sample for every sample in correlogram 508 until it reaches a Max_Delay 506.

The location of the peak of the correlogram is found in a step 484 (see FIG. 48) using a simple peak-detection algorithm, as follows:

$C_{pk}=0$ for (d=1⇒d=N)
if $(C[d]>C_{pk})$ then $[(C_{pk}=C[d])$ and $(N_d=d)]$ where:
  C[d]=value of correlogram at delay d
  $N_d$=location of correlogram peak
  $C_{pk}$=peak amplitude of correlogram.

In a step 488, the peak amplitude of the correlogram is compared to a threshold. This threshold is a fixed value accessible to a supervisor program 486. Regulation of the photodetector signal level using variable-gain amplifiers 52 and 52*a* enable the use of a fixed threshold.

If the peak amplitude of the correlogram exceeds the threshold, the peak location from step 484 is accepted and passed to a step 490 in which the velocity is calculated. The velocity calculated in step 490 then replaces the oldest velocity value in scrolling velocity list 472 (see FIG. 47). If the amplitude of the correlogram is less than or equal to the threshold, the signal processor returns a NULL value 494, and scrolling velocity list 472 remains unchanged.

For a valid correlogram, a velocity 492 is computed from the correlogram peak location using the following relation:

$$t_t = N_d \cdot t_{samp}$$

and $$v = s/t_t$$

where:
t_t=transit time, grating-to-grating (sec)
t_{samp}=signal sample time
s=grating-to-grating distance (mm)
v=velocity (mm/sec).

The running average velocity estimate is acquired by the supervisor program and translated into a frequency signal used by Instrument Timing Generator 146, as shown in FIG. 19.

FIG. 50 shows the structure of the supervisor program for the fourth embodiment of the present invention. System operation is initiated in a start block 510 when the gain of the variable gain amplifier is set to nominal values, and objects are introduced into the flow stream for image acquisition.

In a step 512, the supervisor program performs a cross-correlation between segments of the two photodetector signals using a wide span of correlation delays. The delay value yielding the largest peak in the correlogram is used in a step 514 to compute the initial velocity. The cross-correlation delay limits are set in a step 516 to bracket this initial delay value.

With the cross-correlation delay limits set, object velocity processing commences. During this processing, the supervisor program continuously measures the velocity using the cross correlation method and adjusts the correlation delay limits to maintain execution of a short-span cross-correlation in the neighborhood of the delay required for the current flow velocity. Use of the short-span cross correlation reduces computation time.

A step 478a provides for capturing the photodetector signal segments; a step 482, computes the short-delay-span cross-correlation; a step 490 computes the velocity and tabulates the results in a scrolling velocity list 472 to provide the information for adjusting the correlation limits. The limits are determined in a step 518 from the average of the values in velocity table 472. This average velocity is converted to an expected correlation time delay value, and the limits are placed symmetrically around this expected delay. The offset from the expected value to the minimum delay and the offset from the expected value to the maximum delay are empirically determined and stored in a look-up table to be used in the limit calculation step 518. In a step 516, the correlation offset limits are set and stored in locations accessible to the cross-correlation determination in step 482 for use in processing the next segment of the photodetector signals.

The supervisor program also continuously optimizes the gain of the variable gain amplifiers to maximize SNR as specimen characteristics change, without causing saturation at the ADC. The process of regulating the gains of the amplifiers is initiated in steps 480a and 480b, which compute the integrated magnitudes of the signal segments. The magnitudes are delivered to tables 520 and 526, which contain a set of the most recent magnitudes. Adjustments to the gains are computed by steps 522 and 528 from the maximum magnitudes in tables 520 and 526 and the new setting to variable gain amplifiers 52 and 52a are made in steps 524 and 530. The gain adjustment in steps 524 and 530 uses a "fast attack," "slow recovery" algorithm as described above, to regulate the gain of the variable gain amplifiers.

It should be noted that the method described above for processing the electrical signals produced by the photodetector(s) in the third and fourth embodiments using the TDVMs can also be applied to determining the velocity of objects disposed on a substrate (and the velocity of the substrate) that is caused to move through the FOV. Generally, either the TDVM or the FDVM approach can be used for determining the velocity of any configuration of objects moving through the FOV.

The Use of Calibration Beads in Flow Imaging Systems

The above descriptions of the velocity detection apparatus and methods for detecting velocity of objects in flow have assumed that the object upon which the velocity measurement is performed is representative of the objects of primary interest to be imaged. Under certain conditions, it is beneficial to introduce into, or spike, the sample containing the particles of imaging interest with different types of particles, specifically to facilitate velocity measurement.

In the description below, and the claims that follow, particles introduced into a flow of fluid in an imaging apparatus for the purpose of establishing a velocity are referred to as "calibration beads". In the examples presented herein such calibration beads are preferably polymer micro spheres, but it should be understood that substantially any object capable of being suspended in a fluid, and whose dimensions are compatible with the imaging system being employed, can be utilized as a calibration bead. With respect to the dimensions, such calibration beads must be small enough to pass through the flow cell of the imaging system without obstruction, and yet large enough to be readily detectable by the imaging systems optics and sensors. An optimal size calibration bead for a first imaging system may not represent an optimal size for a second imaging system. Examples of particles that can be beneficially employed as calibration beads include cells, cell clusters, labeled and unlabelled micro spheres (polymer, copolymer, tetra polymer and silica beads).

As described in detail above, flow imaging instruments employing TDI detectors require accurate velocity information for the objects entrained in the flow. Calibration beads can facilitate such velocity measurements. The use of such calibration beads is particularly helpful when the fluid flow contains only a small number of objects, when only a small volume of sample fluid is available, when only limited amounts of light from target cells are available, when a distribution of target cells in a sample is uneven, and to facilitate diagnostic and calibration procedures. Such uses are described in more detail below.

Small Cell Concentration: It is preferable to continuously monitor the speed of the objects in the flow cell, allowing for continuously synchronized TDI detector with flow speed. Samples having low concentration of objects, such as cells, present difficulties with continuous TDI detector/flow speed synchronization, because there is generally a relatively large time duration between different cells passing through the field of view. Adding a high concentration of calibration beads enables the continuous detection of flow speed velocity, thereby facilitating substantially continuous TDI detector/flow speed synchronization.

As noted above, the specifications of an imaging system will enable a preferred range of dimensions to be determined for calibration beads. Similarly, the specifications of an imaging system will also help determine a preferred concentration of calibration beads, the preferred concentration being selected to ensure that sufficient calibration beads are provided so that the velocity of the fluid in the flow cell is continually monitored. Useful specifications, as will be described in more detail below, include information about the TDI detector and the flow cell.

With respect to flow cells, it should be recognized that flow cells employed in flow imaging systems have a sheath diameter, representing the diameter of the fluid path in the flow cell. Preferably, that diameter is sufficiently large to allow particulate laden fluids to pass through the flow cell without blockage. A sheath fluid, which does not include the objects of interest (or the calibration beads) is introduced into the flow cell. A core fluid, containing the objects of interest as well as any calibration beads, is also introduced into the flow cell, such that the core fluid generally passes through the flow cell along a central axis, and such that the sheath fluid generally surrounds the core fluid. The focal point of the imaging system is aligned with the core fluid, so that objects of interest can be imaged.

Understanding the definitions of specific terms employed in the following description will be helpful. In the context of the present invention, the terms object space and image space are employed to differentiate between the actual object (object space) and the projected image of the object onto the TDI camera (image space). A preferred flow imaging system employs a 36× optical magnification and a TDI camera whose pixels are 18 microns square. Therefore, in the image space, the system's resolution, as determined by the pixilated camera, is 18 microns. This resolution (given a 36× magnification) allows for a resolution in object space of 0.5 microns; therefore, cellular images will have 0.5 micron resolution. Note that in certain applications, it may be desirable to increase the magnification (for example, using the same TDI camera, 72× magnification would result in a resolution of 0.25 microns in object space). It should be understood that as magnification is increased, the field of view is decreased; thus the need for enhanced magnification must be balanced with a desired field of view.

The phrase "pixel dimension in object space" indicates that the 0.5 or 0.25 micron dimension of the object (depending on the magnification) coincides with a single camera pixel (18 microns in image space). By using beads with sizes of 500 to 200 nanometers, the image of such beads should be confined to a single camera pixel. However, any distortion/aberrations with the optical path will contribute to dispersion and defocusing of light, causing light to fall on more than a single camera pixel in object space. This spreading of the light is referred to as the point spread function.

An update cycle refers to the velocity feedback loop of the TDI camera employed in a preferred flow imaging system. As discussed in detail above with respect to the methods for determining velocity, it is desirable to determine accurate velocity information to enable the TDI camera to be synchronized to the flow of fluid. Assuming that a preferred TDI camera has a feedback loop of 5 Hz, and assuming a flow of 2 nanoliters of sample flowing per second, a preferred sample flow (during each 5 Hz cycle) is 0.4 nanoliters (2 nanoliters/sec divided by 5 Hz).

For a particular imaging system, assume a TDI camera of the imaging system has a maximum line read out rate frequency of 50 kHz, and a pixel height in image space of 0.5 microns. Such a system yields a maximum flow speed of 25 mm per second. Further assume that the diameter of the core fluid flowing through the flow cell of the imaging system is 10 microns in diameter, yielding a flow rate of approximately 2 nanoliters per second. Given that the velocity/TDI camera feedback loop bandwidth is approximately 5 Hz, this allows approximately 0.4 nanoliters of fluid to pass per update cycle, as described above. In a preferred embodiment, an optimal situation would be to provide one particle in flow cell per update cycle, that volume, which corresponds to 1 particle per 0.4 nanoliters of fluid. This in turn corresponds to a preferred calibration bead concentration of $2.5 \times 10^6$ particles/ml, for the described imaging system. Of course, performing the above calculations for imaging systems having different specifications would result in a different preferred concentration.

Often the concentration of objects of interest in a sample will be far below the preferred concentration calculated above. Sufficient calibration beads can be employed such that a preferred concentration of objects that can be used to determine velocity are present in the flow cell during the use of the imaging instrument.

Small Sample Volume: Another circumstance in which the use of calibration beads can facilitate accurate velocity measurements is when the sample volume is small. Certain samples are limited in their available volumes. Therefore, it is advantageous to design analytical techniques that use the least amount of sample as possible. It should be understood that it often takes a significant volume of sample to initialize a system, i.e. dead volume, and to establish a stable hydrodynamically focused core with respect to the core/sheath structure in a hydrodynamically focused flow cell. Particularly when the volume of sample is limited, it is preferred to employ a substitute core/sample fluid during this initialization process. Rather than using the sample as a core fluid during such initialization, a fluid including only calibration beads (and no sample) is preferably employed until the system is stabilized. The calibration beads in such a calibration core fluid will enable the TDI Camera/Velocity synchronization to be established. When the hydrodynamically focused core stream is stable and the system is initialized, the sample containing the objects of imaging interest can be introduced into the core stream for analysis of the sample objects. Further description of the fluidic system and modes of operations can be found in the section entitled "Description of a Preferred Fluidic System".

Limited Light from Certain Cells: Yet another situation in which the use of calibration beads can facilitate the establishment of TDI Camera/Velocity synchronization is when the amount of light from an object of interest is relatively small, or at least smaller than an amount of light that would be provided by a calibration bead. The velocity detection measurement described in detail above employs an optical grating to modulate light from cells or other objects. As noted earlier, this modulated light can be a result of scattered light from the object, a stimulated emission from the object, an un-stimulated emission from the object, or light transmitted through the object. The signal strength of the light from the objects can be proportional the size of the object. In the case where velocity detection is determined by light scatter from the object, a larger light intensity allows for an increased signal to noise ratio, enabling increased precision in the velocity measurement. Particles of interest which are quite small (i.e. submicron in size) will scatter relatively small amounts of light, resulting in a reduced velocity detection resolution. By using relatively large calibration beads (preferably one to ten microns in diameter), one can increase light scatter and therefore increase velocity detection resolution.

Non-Uniform Cell Scatter: Still another situation in which the use of calibration beads can facilitate the establishment of TDI Camera/Velocity synchronization is when the imaging system will be used with a variety of different samples or with a single sample that includes a plurality of different objects of interest, each of which produces a different image. Use of calibration beads will allow for a more uniform and precise velocity detection, particularly if the majority of the objects passing through the flow cell are calibration beads. Given that imaging systems such as those described in detail above can be used for a vast array of different samples, having a consistent particle (i.e. calibration beads) to perform velocity detection allows for consistency in the operation of the assays.

Optical Self-Diagnostics, Calibration and Quality Metrics: The use of calibration beads in a flow imaging instrument provides a known data source that can be employed in various self-diagnostic, calibration and quality metric applications for the optical system of the instrument. Imagery collected from calibration beads can be used to determine point spread functions associated with an imaging system, to determine a sensitivity of an imaging system, and to determine a focal point of the imaging system. Each of these applications is described in additional detail below.

Point Spread Function: By using the imagery collected from small calibration beads (bead sizes equal to or smaller than the pixel dimension in object space) one can determine the point spread function by comparing the known calibration bead size with the image. As the pixel size in an anticipated embodiment of an imaging system might be 0.5 or 0.25 microns in objects space, this would require utilizing calibration beads of 200 to 500 nm in size. However, such small beads do not provide much scattered light, and it would be preferable to employ larger calibration beads to provide a greater velocity detection resolution. To achieve such enhanced velocity detection resolution it would be preferable to employ calibration beads having a size of from about 1–10 microns.

One solution that would provide both an acceptable velocity detection resolution and facilitate the determination of the point spread function described above is to provide a set of calibration beads that includes a known distribution or grouping of different sized calibration beads, in order to achieve both the goal of determining point spread function and providing the desired velocity detection resolution.

With respect to determining the point spread function, it is advantageous to use fluorescent labeled beads in such a set, as the imagery collected in the fluorescent image channels will not be distorted by refractive index differences between the bead and core material, which does affect both the bright field and dark field channel imagery data. Therefore, in addition to having a distribution of different sized calibration beads, it is advantageous to have plurality of different types of calibration beads (i.e. differently labeled calibration beads) within the calibration bead set.

Sensitivity Calibration: By utilizing a calibration bead set with some distribution of calibration beads having known fluorescent label concentrations, the measured fluorescent image can be compared to the known MESF (molecules of equivalent soluble fluorochrome) to allow for calibration, to insure that the imaging system is providing reproducible results.

Focus: By comparing the size and shape of the collected images against known images of the calibration beads, one can determine if the particle is in focus and diagnose the overall performance of the imaging optics.

Flow Cell Self-Diagnostics, Calibration and Quality Metrics: The known data source provided by the calibration beads can not only be used for self-diagnostic, calibration and quality metric applications for the optical system of the imagining system, but also for the flow cell of the imaging system. Imagery collected from calibration beads can be used to determine core size and stability and TDI/flow speed synchronization. Again, each of these applications is described in additional detail below.

Core Size and Stability: Using known and highly concentrated calibration beads one can image these beads to determine if the hydrodynamically focused core is stable, as well as determine the core size. Specifically, a histogram of the lateral position of the imaged beads will produce a normal distribution defining the core diameter. The use of calibration beads in a relatively high concentration (such that at least one calibration bead is imaged during each update cycle, as was calculated above) enables continuous monitoring of the core size.

System Check for Camera/Flow Speed Synchronization: By comparing the collected images of calibration beads to the known circular cross section of the calibration bead, one can determine if the flow speed is synchronized to the TDI camera. Collected images that are elongated in height, or shortened in height, are indicative of poor synchronization.

Preferred Materials and Properties of Calibration Beads: The calibration beads are preferably polymeric beads of any of the following types: polystyrene, styrene/divinylbenzene copolymer (S/DVB), polymethylmethacrylate (PMMA), polyvinyltoluene (PVT), styrene/butadiene (S/B), styrene/vinyltoluene (S/VT). Mixtures of different types of calibration beads may be used. Preferable calibration beads will have densities in the range of 0.9–2.3 grams per cubic centimeter, and diameters that range from 20 nanometers to 50 microns.

Calibration beads may incorporate surface functional groups enabling the covalent coupling of ligands. Such surface functional groups preferably include: sulfate based groups ($—SO_4$), aldehyde based groups (—CHO), aliphatic amine based groups ($—CH_2—NH_2$), amide based groups ($—CONH_2$), aromatic amine based groups ($—NH_2$), carboxylic acid based groups (—COOH), chloromethyl based groups ($—CH_2—Cl$), hydrazide based groups ($CONH—NH_2$), hydroxyl based groups (—OH), and sulfonate based groups ($—SO_3$).

Calibration beads can be beneficially incorporate a coating of protein A or streptavidin. Further, calibration beads can include dyed microspheres of different colors, fluorescent labeled microspheres, magnetic microspheres, and molecularly imprinted micro spheres.

It should be understood that while the above noted materials and properties are preferred, such materials and properties are merely exemplary, and should not be considered to limit the invention. Calibration beads of other materials and properties are anticipated, so long as such materials and properties combine to achieve calibration beads that 1) can be entrained in a fluid; 2) are of a size that is sufficiently small so as to be able to readily pass through the flow cell of an imaging system without obstruction; and 3) are of a size that is sufficiently large so as to facilitate the desired velocity detection resolution in a particular imaging system.

FIG. 51 illustrates continuously segmented multispectral image data set of a population of fluorescent calibration polymer beads generated by the ImageStream™ prototype system. The bead population consisted of 4 micron diameter unlabelled beads, 4 micron FITC (fluoresceinisothiocyanate) labeled beads, and 4 micron PE (phycoerythrin) labeled beads. The system is configured for brightfield imagery (600–650 nm), PE fluorescence imagery, FITC fluorescence imagery and dark field imagery (488 nm). Images of each bead appear in the bright field and dark field channels, along with a fluorescence image in the channel corresponding to the dye present on each of the 4 micron fluorescent calibration beads. The imagery was gathered at a magnification of 20×, corresponding to the pixel size of approximately 0.65 microns at the object. The dark field imagery shows the lensing effect of each bead due to its large index of refraction relative to the buffer solution.

FIG. 52 illustrates continuously segmented data from ten unlabeled beads, each 350 nm in diameter. The orthogonal scattered light images were collected using 488, 532, 670 and 2780 nm laser excitation. This data was collected with an early prototype imaging system employing chromatically uncorrected optics optimized at 670 nm. As a result, the 670 nm scattered light data is most in focus, and in some cases the scattered light is represented by a single or few pixels of the detector. These 350 nm calibration particles can be used to determine the point spread function.

FIG. 53 illustrates the fluidics of a preferred imaging system. The system has three fluidic pumps. The first pump is a sample syringe pump 600, which holds a ten microliter glass syringe. A preferred syringe pump is disclosed in a commonly assigned copending U.S. Provisional patent application entitled "CELL SUSPENSION ROTATING FLUIDIC PUMP", which is herein specifically incorporated by reference. Sample syringe pump 600 allows rotation of the cylindrical barrel along its barrel axis, in order to uniformly suspend particulates contained in the sample (e.g. beads, cells, or other objects of interest), as well as a motorized control of the piston plunger for low pulsatility and low volume injection capabilities. Syringe pump 600 aspirates or loads fluidic sample from a sample holding pipette 674. Prior to loading the sample into syringe pump 600, a sample valve controller stepper motor 620 actuates a sample valve 660 to connect the 25 micron diameter fluidic line between sample syringe pump 600 and sample holding pipette 674.

The second pump is a bead syringe pump 602, which holds a ten micro liter glass syringe. Preferably, the calibration beads discussed above are introduced into a flow imaging system via bead syringe pump 602. A preferred embodiment of syringe pump 602 is similarly disclosed in the above noted copending U.S. Provisional patent application, and allows for rotation of the cylindrical barrel along its barrel axis in order to uniformly suspend particulates contained in the sample (e.g. beads, cells, or other objects of interest) as well as a motorized control of the piston plunger for low pulsatility and low volume injection capabilities. Syringe pump 602 aspirates or loads fluidic suspension of beads from a bead holding pipette 676. Prior to loading the bead suspension into bead syringe pump 602, a sample valve controller stepper motor 621 actuates a bead valve 661 to connect the 25 micron diameter fluidic line between bead syringe pump 602 and bead holding pipette 676.

The third pump is a sheath syringe pump 604, which holds a 20 milliliter glass syringe. Again, a preferred sheath syringe pump 604 is disclosed in the above noted copending U.S. provisional patent application, allows for motorized control of the piston plunger for low pulsatility and low volume injection capabilities. Sheath syringe pump 604 aspirates or loads sheath fluid from a sheath reservoir 651. This reservoir is vented to ambient atmosphere using a vent line 636 and a 0.2 micron filter 680. Prior to loading the sheath fluid into sheath syringe pump 604 a sheath valve controller stepper motor 622 actuates a sheath valve 662 to connect a 50 micron diameter fluidic line 635 between sheath syringe pump 604 and sheath reservoir 651.

Both sample syringe pump 600 and bead syringe pump 602 independently rotate the syringe barrels using rotation stepper motors 625 and 626, respectively. These two syringe pumps and sheath syringe pump 606 use stepper motors 610, 611, 612 to drive the syringe plungers in order to control the dispensing rate. Additionally, stepper motors 615, 616 and 617 allow for the transmission of all three syringe pumps from low speed injection/aspiration to high speed injection/aspiration. This transmission mechanism is explained in detail in the above referenced provisional patent application.

Initialization of the Fluidic System with Bead Suspension Fluid and Sheath Fluid During the initialization phase of the system, assuming all syringes are loaded with their respective fluids, sheath valve 662 is actuated using sheath valve stepper motor 622, to couple sheath syringe pump 604 to an input sheath pressure tank 672, via a 50 micron diameter fluidic line 634. Sheath pressure tank 672 serves to decrease the inherent pulsatility in sheath syringe pump 604 by having input fluidic line 634 and output fluidic line 633 partially filled with sheath fluid so as to allow for air dampening of the pulsatility. Sheath pressure tank 672 has a vent line 641, which is connected to a pressure relief valve 670, a waste tank line 640 and a waste tank 650 vented to atmospheric pressure via a 0.2 micron air filter 681. The sheath fluid in output fluidic line 633 enters a hydrodynamically focused flow cell 678, thereby achieving the outer sheath fluid flow in the flow cell.

Bead valve 661 is actuated using bead valve stepper motor 621 to connect bead syringe pump 602 to the sample input of hydrodynamically focused flow cell 678 via a 25 micron diameter bead injection fluidic line 630, and a 25 micron sample and bead union injection fluidic line 632. The solution of calibration beads enters hydrodynamically focused designed flow cell 678, thereby producing the core fluid in the flow cell.

Sample Analysis

Once the imaging system determines that the core/sheath fluid flow in the hydrodynamically focused flow cell is stable, a sample fluid containing the objects of interest can be injected into the core stream of the flow cell. Sample valve 660 is actuated using sample valve stepper motor 620, to couple the sample input of hydrodynamically focused flow cell 678 to bead injection fluidic line 630 and sample and bead union injection fluidic line 632. Note that up until this point the calibration bead fluid from bead syringe pump 602 has been the been the sole component of the core fluid in the flow cell. Several options can be employed to introduce a sample fluid into the core fluid at this point.

A first option is to introduce the sample fluid (using sample syringe pump 600) at a given flow rate, and to reduce the flow rate of the calibration bead solution (using bead syringe pump 602) so as to preserve the same overall flow rate of the core fluid flowing in sample and bead union injection fluidic line 632. This option will preserve the stability of the core/sheath fluid flow in the flow cell.

A second option is to introduce the sample fluid (using sample syringe pump 600) at a given flow rate without adjusting the calibration bead solution flow rate, thereby increasing the overall core fluid flow rate.

A third option is to introduce the sample fluid (using sample syringe pump 600) at a given flow rate, and to terminate the flowing of the bead solution.

Post Analysis

Note that FIG. 3.0 depicts the core and sheath fluids exiting flow cell 678 via a 50 micron diameter fluidic line 638, which is coupled to a 50 micron diameter fluidic line 639 that flows into a waste tank 650. A valve 663 could be used to direct the core and sheath fluids in fluidic line 638 to a destination (not shown) other than waste tank 650. For example, the core and sheath fluids from fluidic line 638 could be recirculated back into flow cell 678, or could be directed to a fluid inlet of an additional analytical device for further analysis.

Maintenance of Fluidic Pathways

Valves 663 and 664 preferably can be actuated by stepper motors 623 and 624 to allow for back flushing of the fluidic lines, and the flow cell, to remove obstructions. Additionally, such valves can be used to purge fluidic lines of fluid, as well as to fill fluidic lines with cleaning/sterilization agents such as alcohol.

Alternative Embodiments

Single Syringe Pump for both Sample and Calibration Beads: One anticipated embodiment of a simplified fluidic system utilizes only two fluidic pumps, one for providing the sheath fluid and a second pump for the combined delivery of sample fluid and calibration bead fluid. In such an embodiment, the sample and calibration beads are premixed and simultaneously present in the combined second syringe pump. Additionally, it would be possible to operate such an analysis instrument without the use of a sheath fluid, thus an even simpler embodiment could employ only a single fluid pump.

FIG. 54 shows the overall steps for employing calibration beads to enhance the performance of a flow imaging system. In a block 700 specific calibration beads are selected, based on the parameters of the flow imaging system. As noted above, the size of calibration beads must be matched the imaging system that is being used, to ensure that the calibration beads can pass through the fluidic system. It is also desirable to select calibration beads that are expected to provide a consistent data signal, either based on empirical experience or based on theoretical considerations. For certain imaging systems, desirable calibration beads might include a label (such as a fluorescent dye) that is readily detected by the flow imaging system. Including such a label would be particularly effective if it was known that the sample (the objects of interest that will be imaged by the flow imaging system once the flow imaging system is stable) does not include the same label(s).

In an optional block 702, a desired concentration can be calculated. As discussed above, based on the characteristics of the detector and the flow rate, it is possible to determine a concentration of calibration beads that is expected to provide a substantially continuous data signal. While this step is preferred, it has been indicated as an optional step, because it is anticipated that highly concentrated calibration fluids (i.e. fluids containing in excess of $1 \times 10^8$ calibration beads per milliliter of fluid) will likely be sufficiently concentrated to provide a consistent data signal.

In a block 704 the calibration beads are introduced into flow imaging system, preferably employing one of the fluidic pump systems described above. Calibration bead fluid is provided on an ongoing basis at a predetermined flow rate (based on design parameters of the imaging system) until the flow imaging system stabilizes. While such stabilization might simply mean that a desired sheath flow and core flow is established, an optional block 706 indicates that in at least some embodiments the establishment of TDI synchronization is desirable. The relationship between the acquisition of reliable velocity data and the ability of the flow imaging system to synchronize the TDI detector to the fluid flow has been discussed in detail above.

In an optional block 708, selected diagnostic and calibration procedures can be performed. Such procedures, discussed in greater detail above, include the determination of the point spread function, sensitivity calibration, and optical system focus.

In a block 710, the sample fluid is introduced into the flow imaging system. As noted above, while the sample fluid is introduced into the flow cell of the flow imaging system (specifically to the core flow of the flow cell), the calibration fluid can be maintained at a constant flow rate, reduced proportional to the amount of sample fluid introduced, or eliminated entirely.

In a block 712, the flow imaging system collects sample data based on the images of the sample objects.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for using an engineered sample of calibration objects to enhance the performance of a flow imaging system configured to obtain images of sample objects entrained in a flow of fluid passing through the flow imaging system, using a time-delay-integration (TDI) detector, comprising the steps of:

(a) providing an engineered sample of calibration objects that enables a reliable data signal to be obtained during each update cycle of the flow imaging system, each calibration object being sufficiently small so as to readily pass through the fluidics of the flow imaging system;

(b) introducing the engineered sample of calibration objects into the flow of fluid passing through the flow imaging system;

(c) using the flow imaging system to collect data corresponding to the engineered sample of calibration objects, the data enabling the flow imaging system to reach and maintain a stable state, the data including velocity data that are used to synchronize the TDI detector to the flow of fluid passing through the flow imaging system, the data further including diagnostic data indicating whether the flow imaging system is functioning as desired; and (d) introducing sample objects into the flow of fluid passing through the flow imaging system, whereby synchronization of the TDI detector to the flow of fluid passing through the flow imaging system that is facilitated by the engineered sample of calibration objects enhances the ability of the flow imaging system to collect data corresponding to the sample objects.

2. A method for using calibration objects to enhance the performance of a flow imaging system configured to obtain images of sample objects entrained within a flow of fluid passing through the flow imaging system using a time-delay-integration (TDI) detector, comprising the steps of:

(a) introducing a plurality of calibration objects entrained in a flow of fluid into the flow imaging system;

(b) modulating light from the plurality of calibration objects using an optical grating to produce modulated light having a modulation frequency that varies as a function of the velocity of the flow of fluid;

(c) using the modulated light to determine the velocity of the fluid;

(d) using the velocity to synchronize the TDI detector to the flow of fluid passing through the flow imaging system; and (e) using data collected by the flow imaging system corresponding to the calibration objects to perform a diagnostic check on the flow imaging system.

3. The method of claim 2, wherein the diagnostic check is performed under at least one of the following conditions:

(a) before sample objects are introduced in the flow of fluid;

(b) while sample objects are introduced in the flow of fluid; and (c) after sample objects have been introduced in the flow of fluid.

4. The method of claim 2, wherein:

(a) at least some of the calibration objects are fluorescently labeled; and (b) the step of using data collected by the flow imaging system corresponding to the calibration objects to perform a diagnostic check on the flow imaging system comprises the step of using spectral data collected from the calibration objects to calibrate the flow imaging system.

5. The method of claim 2, wherein the step of using data collected by the flow imaging system corresponding to the calibration objects to perform a diagnostic check on the flow imaging system comprises at least two of the following steps:

(a) determining a point spread function associated with optical components of the flow imaging system;

(b) determining if the flow imaging system is properly focused;

(c) determining if an axis of the flow of fluid is properly aligned relative to the flow imaging system; and (d) determining if the TDI detector is synchronized to the flow of fluid.

6. The method of claim 2, wherein the step of introducing a plurality of calibration objects entrained in a flow of fluid into the flow imaging system comprises the step of introducing calibration objects that range from about 1 micron in diameter to about 10 microns in diameter.

7. The method of claim 2, wherein the step of introducing a plurality of calibration objects entrained in a flow of fluid into the flow imaging system comprises the step of introducing at least one of the following calibration object sets:

(a) a first calibration object set comprising:

(i) a plurality of calibration objects of relatively smaller size, the relatively smaller size having been selected to enhance the determination of the point spread function; and (ii) a plurality of calibration objects of relatively larger size, the relatively larger size having been selected to enhance the determination of the velocity of the flow of fluid; and (b) a second calibration object set comprising:

(i) a plurality of calibration objects of that have been fluorescently labeled, the fluorescent labels having been selected to facilitate calibration of the flow imaging system; and (ii) a plurality of calibration objects having a specified size, the specified size having been selected to enhance the determination of the velocity of the flow of fluid.

8. A method for using calibration objects to enhance the performance of a flow imaging system configured to obtain images of sample objects entrained within a flow of fluid passing through the flow imaging system using a time-delay-integration (TDI) detector, comprising the steps of:

(a) introducing a plurality of calibration objects entrained in a flow of fluid into the flow imaging system;

(b) using data collected by the flow imaging system corresponding to the calibration objects to determine a velocity of the flow of fluid;

(c) using the velocity to synchronize the TDI detector to the flow of fluid; and (d) using data collected by the flow imaging system corresponding to the calibration objects to perform a diagnostic check on the flow imaging system.

9. The method of claim 8, wherein the diagnostic check is performed before sample objects are introduced in the flow of fluid.

10. The method of claim 8, wherein the diagnostic check is performed while sample objects are introduced in the flow of fluid.

11. The method of claim 8, wherein the diagnostic check is performed after sample objects have been introduced in the flow of fluid.

12. The method of claim 8, wherein the step of using data collected by the flow imaging system corresponding to the calibration objects to perform a diagnostic check on the flow imaging system comprises the step of determining a point spread function associated with optical components of the flow imaging system.

13. The method of claim 12, further comprising the step of adjusting the optical components of the flow imaging system to achieve a desired point spread function.

14. The method of claim 8, wherein:

(a) at least some of the calibration objects are fluorescently labeled; and (b) the step of using data collected by the flow imaging system corresponding to the calibration objects to perform a diagnostic check on the flow imaging system comprises the step of using spectral data collected from the calibration objects to calibrate the flow imaging system.

15. The method of claim 8, wherein the step of using data collected by the flow imaging system corresponding to the calibration objects to perform a diagnostic check on the flow imaging system comprises at least one of the following steps:

(a) determining if the flow imaging system is properly focused;

(b) determining whether the flow of fluid is aligned with the desired axis within the flow imaging system; and (c) determining if the TDI detector is synchronized to the flow of fluid.

16. The method of claim 15, wherein the step determining whether the flow of fluid is aligned with the desired axis within the flow imaging system comprises the step of comparing the lateral positions of a plurality of images of different calibration objects obtained by the TDI detector.

17. The method of claim 15, wherein the step determining whether the TDI detector is synchronized to the flow of fluid comprises the step of analyzing a plurality of images of different calibration objects obtained by the TDI detector, elongated and shortened images being indicative of insufficient synchronization.

18. The method of claim 8, wherein the step of introducing a plurality of calibration objects entrained in a flow of fluid into the flow imaging system comprises the step of introducing calibration objects that range from about 1 micron in diameter to about 10 microns in diameter.

19. The method of claim 8, wherein the step of introducing a plurality of calibration objects entrained in a flow of fluid into the flow imaging system comprises the step of introducing:
(a) a plurality of calibration objects of that have been fluorescently labeled, the fluorescent labels having been selected to facilitate calibration of the flow imaging system; and
(b) a plurality of calibration objects having a specified size, the specified size having been selected to enhance the determination of the velocity of the flow of fluid.

20. The method of claim 8, wherein the step of introducing a plurality of calibration objects entrained in a flow of fluid into the flow imaging system comprises the step of introducing:
(a) a plurality of calibration objects of relatively smaller size, the relatively smaller size having been selected to enhance the determination of the point spread function; and
(b) a plurality of calibration objects of relatively larger size, the relatively larger size having been selected to enhance the determination of the velocity of the flow of fluid.

21. The method of claim 20, wherein the relatively smaller size calibration objects have been selected as a function of optical characteristics of the flow imaging system and a pixel size of the TDI detector, such that images of individual calibration objects of the relatively smaller size collected by the TDI detector are substantially confined to a single pixel.

22. The method of claim 20, wherein the relatively larger size calibration objects have been selected to fall within a range of about 1 micron to about 10 microns in diameter, and the relatively smaller size calibration objects have been selected to fall within a range of about 200 nanometers to about 500 nanometers in diameter.

23. The method of claim 8, wherein the step of introducing a plurality of calibration objects entrained in a flow of fluid into the flow imaging system comprises the step of introducing at least some calibration objects having a first size range that is selected as a function of optical characteristics of the flow imaging system and a pixel size of the TDI detector, such that images of individual calibration objects of the first size range collected by the TDI detector are substantially confined to a single pixel.

24. The method of claim 8, wherein the step of introducing a plurality of calibration objects entrained in a flow of fluid into the flow imaging system comprises the steps of:
(a) determining a flow rate of calibration objects required to ensure at least one calibration object is imaged by the TDI detector per update cycle; and
(b) substantially providing the flow rate of calibration objects so determined.

25. The method of claim 8, wherein:
(a) the step of introducing a plurality of calibration objects entrained in a flow of fluid into the flow imaging system comprises the steps of:
(i) establishing a flow of a sheath fluid through the flow imaging system; and
(ii) establishing a flow of a core fluid through the flow imaging system, the calibration objects being entrained within the core fluid; and
(b) the step of the step of using data collected by the flow imaging system corresponding to the calibration objects to perform a diagnostic check on the flow imaging system comprises the step determining whether the core fluid is hydrodynamically focused by the sheath fluid.

26. The method of claim 8, wherein the step of introducing a plurality of calibration objects entrained in a flow of fluid into the flow imaging system comprises the step of selecting a desired size of the calibration objects as a function of a size of sample objects to be analyzed, such that the desired size of each calibration object is relatively larger than the size of the sample objects, and as a consequence, while the sample objects are being analyzed by the flow imaging system, the relatively larger size calibration objects enable the velocity of the flow of fluid to be determined, ensuring that the TDI detector remains synchronized to the flow of fluid passing through the flow imaging system.

27. The method of claim 8, further comprising the step of introducing a plurality of sample objects entrained in a flow of fluid into the flow imaging system, such that images of the sample objects incident on the TDI detector are enhanced due to the synchronization of the TDI detector to the flow of fluid passing through the flow imaging system.

28. The method of claim 27, wherein the step of introducing a plurality of sample objects entrained in a flow of fluid into the flow imaging system is performed after the step of introducing a plurality of calibration objects entrained in a flow of fluid into the flow imaging system, such that the plurality of calibration objects facilitate the synchronization of the TDI detector to the flow of fluid before the sample objects are introduced.

29. The method of claim 28, wherein the introduction of the plurality of calibration objects is terminated when the plurality of sample objects are introduced.

30. The method of claim 28, wherein the plurality of sample objects are entrained in a sample fluid, and the plurality of calibration objects are entrained in a calibration fluid, and the step of introducing a plurality of sample objects entrained in a flow of fluid into the flow imaging system comprises the step of maintaining a total volumetric flow of fluid through the flow imaging system constant, such that any increase in volumetric fluid flow attributable to introduction of the sample fluid is offset by a corresponding reduction in a volumetric fluid flow of the calibration fluid.

31. The method of claim 27, wherein the step of introducing a plurality of sample objects entrained in a flow of fluid into the flow imaging system is performed concurrently with the introduction of the plurality of calibration objects.

32. The method of claim 31, wherein the plurality of sample objects and the plurality of calibration objects are entrained in the same flow of fluid.

33. A method for using calibration beads to enhance the performance of a flow imaging system configured to obtain images of sample objects entrained within a flow of fluid passing through the flow imaging system using a time-delay-integration (TDI) detector, comprising the steps of:
(a) establishing a flow of sheath fluid within the flow imaging system;
(b) establishing a flow of core fluid within the flow imaging system, the flow of core fluid including a plurality of calibration beads, said flow of core fluid being surrounded by the flow of sheath fluid;
(c) using data collected by the flow imaging system corresponding to the calibration beads to determine a velocity of the flow of core fluid;
(d) using the velocity to synchronize the TDI detector to the flow of core fluid within the flow imaging system; and (e) using data collected by the flow imaging system corresponding to the calibration beads to perform a diagnostic check on the flow imaging system.

34. The method of claim 33, wherein the diagnostic check is performed under at least one of the following conditions:
(a) before sample objects are introduced in the flow of core fluid;
(b) while sample objects are introduced in the flow of core fluid; and
(c) after sample objects have been introduced in the flow of core fluid.

35. The method of claim 33, wherein the step of using data collected by the flow imaging system corresponding to the calibration beads to perform a diagnostic check on the flow imaging system comprises at least two of the following steps:
(a) determining a point spread function associated with optical components of the flow imaging system;
(b) determining if the flow imaging system is properly focused;
(c) determining if an axis of the flow of core fluid is properly aligned relative to the flow imaging system;
(d) determining if the TDI detector is synchronized to the flow of fluid; and
(e) when at least some of the calibration beads are fluorescently labeled, using spectral data collected from the calibration beads to calibrate the flow imaging system.

36. A flow imaging system adapted to determine an indication of a velocity and at least one additional characteristic of a plurality of objects, from images of the plurality of objects, while there is relative movement between the plurality of objects and the flow imaging system, comprising:
(a) a fluidic subsystem configured to selectively introduce a fluid in which the plurality of objects are entrained into a field of view, the plurality of objects including at least one of a plurality of calibration objects and a plurality of sample objects;
(b) an optical subsystem configured to convey light from the plurality of objects passing through the field of view;
(c) a velocity measurement subsystem configured to receive the light conveyed by the optical subsystem, and to manipulate said light to determine an indication of the velocity of the relative movement between the plurality of objects and the flow imaging system;
(d) a time-delay-integration (TDI) detector configured to receive the light obtained by the optical subsystem, said TDI detector being coupled to said velocity measurement subsystem, said TDI detector employing a timing signal produced by the velocity measurement subsystem to produce an output signal that is indicative of said at least one additional characteristic of the plurality of objects; and
(e) a control circuit logically coupled with the TDI detector, the control circuit configured to implement a plurality of functions, including using data collected by the flow imaging system corresponding to the plurality of calibration objects to perform at least one diagnostic check on the flow imaging system.

37. The flow imaging system of claim 36, wherein said control circuit is further configured to implement the function of performing the at least one diagnostic check under at least one of the following conditions:

(a) before sample objects are introduced in the flow of fluid;
(b) while sample objects are introduced in the flow of fluid; and
(c) after sample objects have been introduced in the flow of fluid.

38. The flow imaging system of claim 36, wherein the at least one diagnostic check the control circuit is configured to implement comprises at least two of the following diagnostic checks:
(a) determining a point spread function associated with optical components of the flow imaging system;
(b) determining if the flow imaging system is properly focused;
(c) determining if an axis of the flow of fluid is properly aligned relative to the flow imaging system;
(d) determining if the TDI detector is synchronized to the flow of fluid; and
(e) when at least some of the plurality of calibration objects are fluorescently labeled, using spectral data collected from the plurality of calibration objects to calibrate the flow imaging system.

39. The flow imaging system of claim 36, wherein said fluidic subsystem comprises a syringe pump coupled with a fluid supply including a fluid into which a plurality of sample objects and a plurality of calibration objects are entrained.

40. The flow imaging system of claim 36, wherein said fluidic subsystem comprises:
(a) a first syringe pump coupled to a sample fluid supply volume configured to provide a supply of a sample fluid into which a plurality of the sample objects are entrained; and
(b) a second syringe pump coupled a calibration fluid supply volume configured to provide a supply of a calibration fluid into which a plurality of the calibration objects are entrained.

41. The flow imaging system of claim 40, wherein said control circuit is controllably coupled to the fluidic subsystem and is further configured to implement the functions of:
(a) activating the fluidic subsystem so that a flow of calibration fluid is established within the field of view, thus enabling the velocity measurement subsystem to provide the timing signal to the TN detector; and
(b) activating the fluidic subsystem so that a flow of sample fluid is established within the field of view if the diagnostic check indicates that the flow imaging system is ready to analyze the sample objects.

42. The flow imaging system of claim 40, wherein:
(a) the fluidic subsystem further comprises a sheath fluid supply volume configured to provide a supply of a sheath fluid;
(b) the control circuit is further configured to activate the fluidic subsystem so that a flow of sheath fluid is established within the field of view before the calibration fluid is introduced into the field of view; and
(c) the diagnostic check implemented by the control circuit compares a plurality of images of calibration objects incident upon the TDI detector to determine if the relative lateral positions of the plurality of images of the calibration objects indicate that the flow of calibration fluid in the field of view is properly hydrodynamically focused by the sheath fluid.

43. The flow imaging system of claim 40, wherein the control circuit maintains the flow of fluid through the field of view at a constant volumetric flow rate, such that any increase in the volumetric flow rate attributable to introduction of the sample fluid into the field of view is offset by a corresponding reduction in a volumetric flow rate of the calibration fluid into the field of view.

44. The flow imaging system of claim 36, wherein said velocity measurement subsystem comprises:
(a) an optical grating disposed to receive the light conveyed by the optical subsystem, said optical grating modulating the light, producing modulated light that has a modulation frequency corresponding to a velocity of the relative movement between the plurality of objects and the flow imaging system;
(b) a light sensitive detector disposed to receive the modulated light, said light sensitive detector producing an electrical signal in response to the modulated light; and
(c) means coupled to the light sensitive detector to receive the electrical signal, for determining an indication of the velocity of the relative movement between the object and the flow imaging system as a function of the electrical signal and for producing a timing signal as a function of said indication of the velocity.

45. The flow imaging system of claim 36, wherein the control circuit comprises at least one of:
(a) processor coupled to a memory, said memory storing machine instructions that are executed by the processor to implement the plurality of functions; and
(b) an application specific integrated circuit.

46. A flow imaging system adapted to determine an indication of a velocity and at least one additional characteristic of a plurality of objects, from images of the plurality of objects, while there is relative movement between the plurality of objects and the flow imaging system, comprising:
(a) a fluidic subsystem configured to selectively introduce a fluid into which the plurality of objects are entrained into a field of view, the plurality of objects including at least one of calibration objects and sample objects;
(b) an optical subsystem configured to convey light from the plurality of objects passing through the field of view;
(c) a velocity measurement subsystem configured to receive the light conveyed by the optical subsystem and to produce a signal indicative of the velocity of the relative movement between the plurality of objects and the flow imaging system;
(d) a time-delay-integration (TDI) detector configured to receive the light conveyed by the optical subsystem, said TDI detector producing an output signal that is indicative of said at least one additional characteristic of the object; and
(e) a control circuit logically coupled with the velocity measurement subsystem and the TDI detector, the control circuit implementing a plurality of functions, including:
(i) using the signal indicative of the velocity to synchronize the TDI detector to the flow of fluid passing through the flow imaging system; and
(ii) using the output signal to perform at least one diagnostic check on the flow imaging system.

47. The flow imaging system of claim 46, wherein said control circuit is further configured to use the output signal to perform at least one diagnostic check on the flow imaging system under at least one of the following conditions:

(a) before sample objects are introduced in the flow of fluid;
(b) while sample objects are introduced in the flow of fluid; and
(c) after sample objects have been introduced in the flow of fluid.

48. The flow imaging system of claim 46, wherein the at least one diagnostic check the control circuit is configured to implement comprises at least two of the following diagnostic checks:
(a) determining a point spread function associated with optical components of the flow imaging system;
(b) determining if the flow imaging system is properly focused;
(c) determining if an axis of the flow of fluid is properly aligned relative to the flow imaging system;
(d) determining if the TDI detector is synchronized to the flow of fluid; and
(e) when at least some of the calibration beads are fluorescently labeled, using spectral data collected from the calibration beads to calibrate the flow imaging system.

49. A flow imaging system adapted to determine an indication of a velocity and at least one additional characteristic of an object, from images of the object, while there is relative movement between the object and the imaging system, comprising:
(a) a fluidic subsystem configured to selectively introduce a fluid into which at least one type of object is entrained into a field of view, the fluid system comprising:
(i) a sample fluid supply volume configured to provide a supply of a sample fluid in which a plurality of sample objects are entrained;
(ii) a calibration fluid supply volume configured to provide a supply of a calibration fluid in which a plurality of calibration objects are entrained;
(b) an optical subsystem configured to convey light from an object passing through the field of view;
(c) a velocity measurement subsystem configured to receive the light conveyed by the optical subsystem, and to manipulate said light to determine the indication of the velocity of the relative movement between the object and the flow imaging system;
(d) a time-delay-integration (TDI) detector configured to receive the light conveyed by the optical subsystem, said TDI detector producing an output signal that is indicative of said at least one additional characteristic of the object; and
(e) a control circuit controllably coupled with the fluidic subsystem and logically coupled with the TDI detector, the control circuit implementing a plurality of functions, including:
(i) activating the fluidic subsystem so that a flow of the calibration fluid is established within the field of view, thus enabling the velocity measurement subsystem to continuously determine the indication of velocity;
(ii) using data collected by the flow imaging system corresponding to the calibration beads to perform at least one diagnostic check on the flow imaging system; and
(iii) activating the fluidic subsystem so that a flow of sample fluid is established within the field of view, such that images of the sample objects incident on the TDI detector are enhanced due to a synchronization of the TDI detector to the flow of fluid passing through the flow imaging system enabled by the indication of velocity.

50. The flow imaging system of claim 49, wherein the control circuit is logically coupled with the velocity measurement subsystem, and the control circuit is further configured to implement the function of using the indication of velocity determined by the velocity measurement subsystem to continuously synchronize the TDI detector to the flow of fluid passing through the flow imaging system.

51. The flow imaging system of claim 49, wherein the TDI detector is logically coupled to the velocity measurement subsystem, and is configured to use the indication of velocity determined by the velocity measurement subsystem to continuously synchronize the TDI detector to the flow of fluid passing through the flow imaging system.

52. The flow imaging system of claim 49, wherein the control circuit is further configured to activate the fluidic subsystem so that a flow of sample fluid is established within the field of view only after the at least one diagnostic check on the flow imaging system indicates that the flow imaging system is ready to analyze sample objects.

53. The flow imaging system of claim 49, wherein said control circuit is further configured to perform the at least one diagnostic check on the flow imaging system under at least one of the following conditions:
 (a) before sample objects are introduced in the flow of fluid;
 (b) while sample objects are introduced in the flow of fluid; and
 (c) after sample objects have been introduced in the flow of fluid.

54. The flow imaging system of claim 49, wherein the at least on diagnostic check implemented by the control circuit comprises at least one of:
 (a) determining a point spread function associated with optical components of the flow imaging system;
 (b) determining if the flow imaging system is properly focused;
 (c) determining if an axis of the flow of calibration fluid is properly aligned relative to the flow imaging system;
 (d) determining the TDI detector is synchronized to the flow of calibration fluid; and
 (e) when at least some of the calibration beads are fluorescently labeled, using spectral data collected from the calibration beads to calibrate the flow imaging system.

55. The flow imaging system of claim 49, wherein the control circuit is further configured to implement the function of maintaining the flow of fluid through the field of view at a substantially constant volumetric flow rate, such that any increase in the volumetric flow rate attributable to the introduction of the sample fluid into the field of view is offset by a corresponding reduction in a volumetric flow rate of the calibration fluid into the field of view.

56. The method for using calibration objects to enhance the performance of a flow imaging system configured to obtain images of sample objects entrained within a flow of fluid passing through the flow imaging system using a time-delay-integration (TDI) detector, comprising the steps of:
 (a) introducing a plurality of calibration objects entrained in a flow of fluid into the flow imaging system, such that the calibrations objects are larger in size than objects of interest to be imaged by the flow imaging system;
 (b) modulating light from the plurality of calibration objects using an optical grating to produce modulated light having a modulation frequency that varies as a function of the velocity of the flow of fluid;
 (c) using the modulated light to determine the velocity of the fluid;
 (d) using the velocity to synchronize the TDI detector to the flow of fluid passing through the flow imaging system; and
 (e) using data collected by the flow imaging system corresponding to the calibration objects to perform a diagnostic check on the flow imaging system, such that a size difference between the calibrations objects and the objects of interest enable data corresponding to the calibration objects to be easily discriminated from data corresponding to an object of interest.

57. A method for using calibration objects to enhance the performance of a flow imaging system configured to obtain images of sample objects entrained within a flow of fluid passing through the flow imaging system using a time-delay-integration (TDI) detector, comprising the steps of:
 (a) introducing a plurality of calibration objects entrained in a flow of fluid into the flow imaging system, such that the calibrations objects are larger in size than objects of interest to be imaged by the flow imaging system;
 (b) introducing a plurality of objects of interest entrained in a flow of a fluid into the flow imaging system;
 (c) modulating light from the plurality of calibration objects using an optical grating to produce modulated light having a modulation frequency that varies as a function of a velocity of the fluid;
 (d) using the modulated light to determine the velocity of the fluid;
 (e) using the velocity to synchronize the TDI detector to the flow of fluid passing through the flow imaging system;
 (f) using the flow imaging system to collect data corresponding to the plurality of calibration objects and the plurality of objects of interest; and
 (g) separating data collected by the flow imaging system corresponding to the plurality of calibration objects from data collected by the flow imaging system corresponding to the plurality of objects of interest, based on a size difference between the calibration objects and the objects of interest.

58. The method of claim 57, further comprising the step of using data collected by the flow imaging system corresponding to the calibration objects to perform a diagnostic check on the flow imaging system.

59. The method of claim 57, wherein the step of using data collected by the flow imaging system corresponding to the calibration objects to perform a diagnostic check on the flow imaging system comprises at least one of the following steps:
 (a) determining a point spread function associated with optical components of the flow imaging system;
 (b) determining if the flow imaging system is properly focused;
 (c) determining if an axis of the flow of fluid is properly aligned relative to the flow imaging system; and
 (d) determining if the TDI detector is synchronized to the flow of fluid.

* * * * *